US009822137B2

(12) United States Patent
Dehaen et al.

(10) Patent No.: US 9,822,137 B2
(45) Date of Patent: Nov. 21, 2017

(54) PHOSPHONUCLEOSIDES USEFUL IN THE TREATMENT OF VIRAL DISORDERS

(71) Applicants: UNIVERSITY COLLEGE CORK, Cork (IE); KATHOLIEKE UNIVERSITEIT LEUVEN, Leuven (BE)

(72) Inventors: Wim Dehaen, Heverlee (BE); Jan Balzarini, Heverlee (BE); Anita Maguire, Cork (IE); Sarah Jane Keane, Cork (IE); Alan Ford, Cork (IE); Nuala Maguire, Cork (IE); Nicholas D. Mullins, Cork (IE)

(73) Assignees: UNIVERSITY COLLEGE CORK, Cork (IE); KATHOLIEKE UNIVERSITEIT LEUVEN, Leuven (BE)

( * ) Notice: Subject to any disclaimer, the term of this patent is extended or adjusted under 35 U.S.C. 154(b) by 0 days.

(21) Appl. No.: 14/442,970

(22) PCT Filed: Nov. 20, 2013

(86) PCT No.: PCT/EP2013/074321
§ 371 (c)(1),
(2) Date: May 14, 2015

(87) PCT Pub. No.: WO2014/079903
PCT Pub. Date: May 30, 2014

(65) Prior Publication Data
US 2015/0291640 A1    Oct. 15, 2015

Related U.S. Application Data

(60) Provisional application No. 61/728,568, filed on Nov. 20, 2012.

(30) Foreign Application Priority Data

Nov. 20, 2012 (GB) .................................. 1220843.5

(51) Int. Cl.
*A61K 45/06* (2006.01)
*A61K 31/675* (2006.01)
*G01N 33/573* (2006.01)
*C07F 9/6561* (2006.01)
*C07F 9/6512* (2006.01)

(52) U.S. Cl.
CPC ........ *C07F 9/65616* (2013.01); *A61K 31/675* (2013.01); *A61K 45/06* (2013.01); *C07F 9/6561* (2013.01); *C07F 9/65121* (2013.01); *C07F 9/65122* (2013.01); *G01N 33/573* (2013.01); *G01N 2333/9128* (2013.01); *G01N 2500/04* (2013.01); *G01N 2500/20* (2013.01)

(58) Field of Classification Search
CPC ..... A61K 45/06; A61K 31/675; G01N 33/573
See application file for complete search history.

(56) References Cited

PUBLICATIONS

Kim et al., caplus an 1999:137673 (1999).*
Nucleobase, 2017,https://en.wikipedia.org/wiki/Nucleobase.*
Payne et al., 2009, caplus n 2009:616448.*
Tapas et al., 2011, caplus an 2011:1132058.*
Mattia et al., 1994, caplus an 1994:323081.*
Balzarini et al.,PNAS, 2015, 112 (11), 3475-3480.*
Sebastien Debarge et al: "Design and Synthesis of [alpha]-Carboxy Phosphononucleosides", The Journal of Organic Chemistry, vol. 76, No. 1, Jan. 7, 2011 (Jan. 7, 2011), pp. 105-126, XP055094802, ISSN: 0022-3263, DOI: 10.1021/jo101738e, compounds 15-18, 56-61.
Isabelle Hladezuk et al: "Development of OH insertion for the attachment of phosphonates to nucleosides; synthesis of -carboxy phosphononucleosides", Tetrahedron, Elsevier Science Publishers, Amsterdam, NL, vol. 68, No. 7, Dec. 29, 2011 (Dec. 29, 2011), pp. 1894-1909, XP028453878, ISSN: 0040-4020, DOI: 10.1016/J.TET. 2011.12.077 [retrieved on Jan. 3, 2012], p. 1900; compounds 42-46.
Boojamra C G et al: "Design, synthesis, and anti-HIV activity of 4'-modified carbocyclic nucleoside phosphonate reverse transcriptase inhibitors", Bioorganic & Medicinal Chemistry, Pergamon, GB, vol. 17, No. 4, Feb. 15, 2009 (Feb. 15, 2009), pp. 1739-1746, XP025949584, ISSN: 0968-0896, DOI: 10.1016/J. MC.2008.12.028 [retrieved on Feb. 15, 2009], cited in the application, p. 1742.
International Search Report of PCT/EP2013/074321, dated Jan. 22, 2014 (Jan. 22, 2014), the whole document.

* cited by examiner

*Primary Examiner* — Sun Jae Yoo
(74) *Attorney, Agent, or Firm* — Steptoe & Johnson LLP

(57) ABSTRACT

A first aspect of the invention relates to a compound of formula (I), or a pharmaceutically acceptable salt or prodrug thereof, wherein the groups are as defined in the claims. Further aspects of the invention relate to pharmaceutical compositions comprising compounds of formula (I), and the use of compounds of formula (I) in the preparation of a medicament for treating a viral disorder.

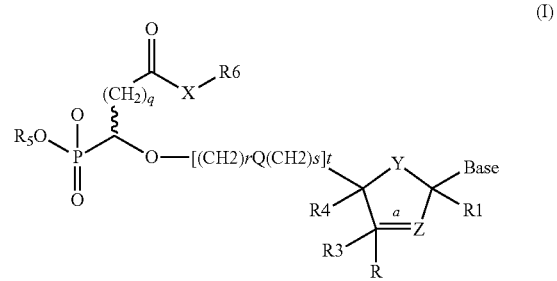

33 Claims, No Drawings

PHOSPHONUCLEOSIDES USEFUL IN THE TREATMENT OF VIRAL DISORDERS

CLAIM FOR PRIORITY

This application claims priority under 35 USC 371 to International Application No. PCT/EP2013/074321, filed Nov. 20, 2013, which claims priority to U.S. Provisional Patent Application No. 61/728,568, filed Nov. 20, 2012, and British Patent Application No. 1220843.5, filed Nov. 20, 2012, each of which is hereby incorporated by reference in its entirety.

The present invention relates to modified phosphonucleosides. More specifically, but not exclusively, the invention relates to modified phosphonucleosides that are capable of treating one or more viral disorders, including DNA and RNA viruses.

BACKGROUND TO THE INVENTION

The human immunodeficiency virus (HIV) was first identified as the causative agent of acquired immunodeficiency syndrome (AIDS) in 1983.[1] At the close of 2010 there were an estimated 34 million people living with the retrovirus worldwide, with approximately 2.7 million people newly infected in 2009 alone.[2] The introduction of the drug regimen HAART (highly active antiretroviral therapy) in 1996 has transformed HIV from a lethal infection to a manageable chronic condition with considerable declines in HIV-associated morbidity and mortality.[3-8] However, as a result of the high genetic variability of the retrovirus, resistance to current drug therapies is a major problem and in addition to HIV there are numerous other chronic viral infections such as hepatitis B and C and human T-lymphotrophic virus 1 (HTLV-1).[7] Approximately 1 in 12 persons worldwide, or some 500 million people, are living with chronic viral hepatitis.[2] In light of this, a vast amount of time and effort has been invested in the design and synthesis of antiviral agents, most notably nucleoside analogues and the discovery of new, more efficient antiviral agents is imperative.

Nucleoside reverse transcriptase inhibitors (NRTIs) were the first class of anti-HIV drugs approved and, despite the discovery of numerous other classes of anti-HIV agents (i.e. nucleotide reverse transcriptase inhibitors, non-nucleoside reverse transcriptase inhibitors, protease inhibitors, integrase inhibitors, cell entry inhibitors and co-receptor inhibitors), they have continued to play a pivotal role in HIV treatment.[8] NRTIs disrupt viral replication through two distinct modes; competitive inhibition of HIV RT with respect to the dNTP substrate, and DNA chain termination.[9,10] However, in order to do this, these compounds must be first converted via a series of host cell kinases to their active triphosphate form.[10-12] The triphosphorylated drug molecules then compete with bona fide nucleotides to be accepted into the growing DNA chain and, if incorporated, chain elongation is terminated since the NRTI lacks the 3'-OH group of endogenous nucleosides.[10] Poor cell membrane permeability coupled with the labile nature of the phosphate bond precludes the direct delivery of the active triphosphorylated form of the drug into the virus-infected cell.[13] This predicament was partially overcome by the use of phosphoramidate, CycloSal or alkoxyalkyl prodrug technology[14-17] and also the discovery of the phosphonate as a stable isostere for the phosphate bond.[18,19]

The discovery of (S)-HPMPA as a broad spectrum antiviral agent swiftly led to the development of a new class of antiviral agents; the nucleotide reverse transcriptase inhibitors (NtRTIs).[19,20] Tenofovir (PMPA) is the only nucleotide reverse transcriptase inhibitor currently approved by the FDA for the treatment of HIV and HBV. It is marketed as the prodrug tenofovir disoproxil fumarate (TDF) which is hydrolysed in vivo to tenofovir.[8,10] The presence of the phosphonate group enables the compound to bypass the initial phosphorylation, which is often the rate-limiting step, and just two phosphorylations are required to furnish the active tenofovir-diphosphate.[8]

Carbocyclic nucleosides are an important subclass of NRTIs where the oxygen of the furanose ring has been replaced by a methylene group.[21-23] This substitution renders these compounds stable to cleavage by intracellular phosphorylases and hydrolases as they lack the labile glycosidic bond of natural nucleosides. Carbocyclic nucleosides also exhibit increased lipophilicity relative to conventional nucleosides leading to increased in vivo half-life, oral efficiency and cell membrane penetration.[22] Naturally-occuring compounds of this type include aristeromycin 1 and neplanocin A 2[24] which possess potent antitumor and antiviral activities. Synthetic carbocyclic derivatives include the antiviral agents abacavir 3[25] and carbocyclic-ddA 4.[26]

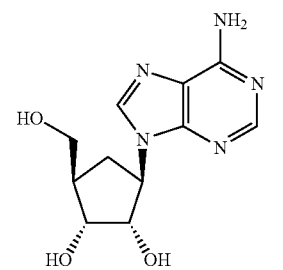

1

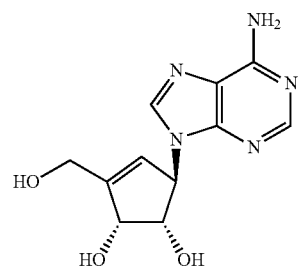

2

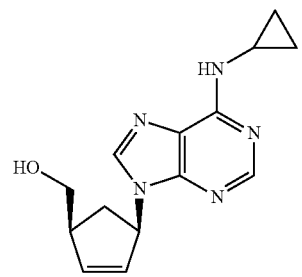

3

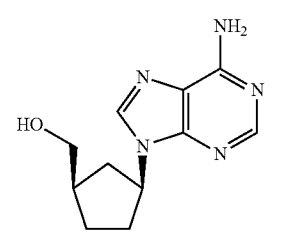

4

The phosphononucleoside 5[27] and the carbocyclic phosphononucleoside 6[28] possess significant anti-HIV activity. The diphosphorylated carbocyclic phosphononucleoside derivative 7 also strongly inhibits HIV-RT.[18] In addition to this, the antiviral properties of phosphonoformic acid (PFA) 8 and phosphonoacetic acid (PAA) 9 were established almost 3 decades ago.[29] McKenna et al. later synthesised a range of halogen- and methyl-substituted derivatives of PAA, a number of which were found to possess potent antiviral activity. Interestingly, the carbonyl derivative 10 was significantly more active than 9.[30]

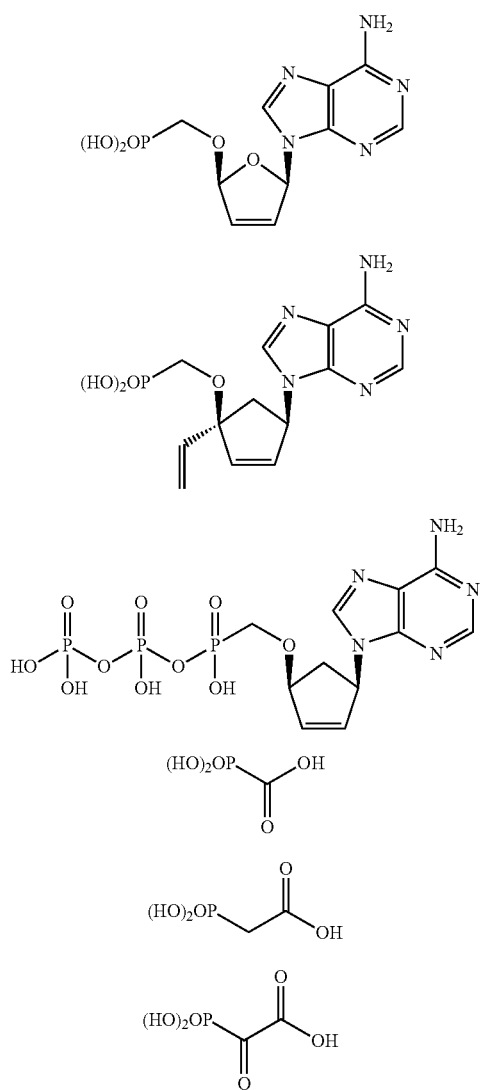

In general, phosphononucleoside research involves compounds bearing a simple $CH_2PO(OH)_2$ substituent; however, there have been some reports of derivatives bearing substituents geminal to the phosphonic acid moiety.[31-36] Gilbert and co-workers described the synthesis of citrate derivatives of nucleosides as potential mimics of nucleoside triphosphates.[37,38] The compounds were found to be inactive, indicating that the citrate moiety is not a good replacement for the phosphate group. Vedras et al. reported the synthesis of nucleoside dicarboxylates as potential nucleoside diphosphate isosteres.[39] Recently Janeba has described acyclic nucleoside phosphonates incorporating an additional remote carboxylic acid function, but these compounds did not exhibit any antiviral activity.[40] The attachment of PAA and PFA by ester and amide linkages to the 5'-O and N-positions of 3TC has been reported previously, but the resulting derivatives were less active against HIV-1 than the parent compound.[41]

The present invention seeks to provide further phosphononucleoside derivatives, particularly those that have therapeutic applications in the treatment of viral disorders, including DNA and RNA viruses such as HIV.

STATEMENT OF INVENTION

A first aspect of the invention relates to a compound of formula (I), or a pharmaceutically acceptable salt or prodrug thereof,

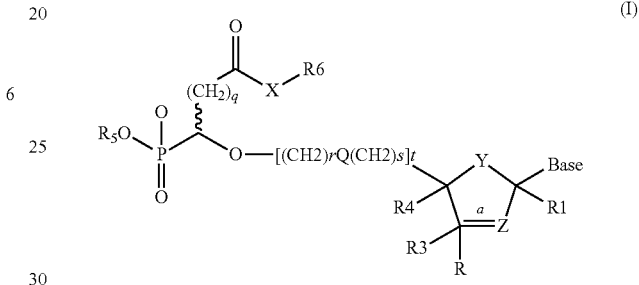

(I)

wherein:
X is selected from O and $NR_9$;
Y is a direct bond, O, S, NH, $NCH_3$, $C=CH_2$ or $(CR_8R_{8'})_n$, where n is 1 or 2;
Z is a direct bond, or $(CR_2R_{2'})_p$, where p is 1, 2, 3 or 4;
Q is selected from O, S, $CH_2$, $CH=CH$ and $C≡C$;
r is 0, 1, 2 or 3;
s is 0, 1, 2 or 3;
t is 0 or 1;
q is 0, 1, 2, 3, 4 or 5;
when p is 1, 2, 3 or 4, 'a' is a single bond, or a double bond (in which case one of $R_2$ and $R_{2'}$ is absent, and one of $R_3$ and $R_{3'}$ is absent);
$R_1$, $R_2$, $R_{2'}$, $R_3$, $R_{3'}$, $R_4$, $R_8$ and $R_{8'}$ are each independently selected from H, $OR_{10}$, halogen, CN, $NR_{11}R_{12}$, $N_3$, $SR_{13}$, $C_{1-6}$-alkyl, $C_{2-6}$-alkenyl, $C_{2-6}$-alkynyl and aryl, or one of $R_2$ and $R_{2'}$ together with one of $R_3$ and $R_{3'}$ form of an epoxide;
$R_5$ is selected from H, $P(=O)(OH)_2$ and $P(=O)(OH)—O—P(=O)(OH)_2$;
$R_6$ is selected from H and $C_{1-6}$-alkyl;
$R_9$-$R_{13}$ are each independently selected from H and $C_{1-6}$-alkyl; and
Base is a natural or non-natural nucleobase.

Synthetic methodology has been developed for the synthesis of a series of novel phosphonate derivatives of carbocylic nucleosides employing transition metal catalysed O—H insertion as the key step. The key novelty of the structures is the incorporation of a carboxylic acid moiety adjacent to the phosphonic acid. Having developed the methodology for the racemic series, extension to both enantiomers was subsequently undertaken through the use of enantioenriched starting materials. Full characterisation of each of the novel compounds has been undertaken, with spectroscopic features which are characteristic due to coupling to $^{31}P$ being particularly useful in the structural assignment. A number of the novel derivatives have displayed pronounced inhibitory activity against HIV-RT, providing exciting new lead compounds in the nucleoside phosphonate field.

A second aspect of the invention relates to a pharmaceutical composition comprising a compound of formula (I) as defined above admixed with a pharmaceutically acceptable diluent, excipient or carrier.

Another aspect of the invention relates to a compound of formula (I) as defined above, or a pharmaceutically acceptable salt or prodrug thereof, for use in medicine.

Another aspect of the invention relates to a compound of formula (I) as defined above, or a pharmaceutically acceptable salt or prodrug thereof, for use in treating a viral disorder.

A further aspect of the invention relate to the use of a compound of formula (I) as defined above, or a pharmaceutically acceptable salt or prodrug thereof, in the preparation of a medicament for treating a viral disorder.

A further aspect of the invention relate to a method of treating a viral disorder, said method comprising administering to a mammal a therapeutically effective amount of a compound according as defined above, or a pharmaceutically acceptable salt or prodrug thereof.

Another aspect of the invention relates to the use of a compound of formula (I) as defined above, or a pharmaceutically acceptable salt or prodrug thereof, in an assay for identifying further candidate compounds capable of inhibiting HIV-RT.

A further aspect of the invention relates to a process for preparing compounds according to the invention.

DETAILED DESCRIPTION

The present invention relates to phosphononucleoside derivatives of formula (I) as defined above, along with therapeutic uses thereof.

As it will be evident from the general formula (I) and the definitions associated therewith, there may be one or several asymmetric carbon atoms present in the presently claimed phosphonucleosides depending on the nature of the substituents. The phosphonucleosides are intended to include all stereoisomers arising from the presence of any and all asymmetric carbon atoms (including substituents on the ring, as well as on side chains thereof), as well as mixtures thereof, including racemic mixtures. When considering 5- or 6-membered rings, it is, however, believed that certain stereochemical configurations will be especially interesting, e.g. compounds of formula (Id) and (Ie) as described below.

As used herein, the term "alkyl" includes both saturated straight chain and branched alkyl groups which may be substituted (mono- or poly-) or unsubstituted. Preferably, the alkyl group is a $C_{1-20}$ alkyl group, more preferably a $C_{1-15}$, more preferably still a $C_{1-12}$ alkyl group, more preferably still, a $C_{1-6}$ alkyl group, more preferably a $C_{1-3}$ alkyl group. Particularly preferred alkyl groups include, for example, methyl, ethyl, propyl, isopropyl, butyl, isobutyl, tert-butyl, pentyl and hexyl. Suitable substituents include one or more groups selected from OH, SH, $NH_2$, $CF_3$, NH-alkyl, N(alkyl)$_2$, alkoxy, halogen, CN, $N_3$, $CO_2$-alkyl, $CO_2H$. Preferably, the alkyl group is unsubstituted.

As used herein, the term "aryl" refers to a $C_{6-12}$ aromatic group which may be substituted (mono- or poly-) or unsubstituted. More preferably, the aryl group is a $C_{6-10}$ aromatic group. Typical examples include phenyl and naphthyl etc. Suitable substituents include one or more groups selected from alkyl, OH, SH, $NH_2$, $CF_3$, NHalkyl, N(alkyl)$_2$, alkoxy, halogen, $N_3$, CN, $CO_2$-alkyl and $CO_2H$.

As used herein, the term "alkenyl" refers to a group containing one or more carbon-carbon double bonds, which may be branched or unbranched, substituted (mono- or poly-) or unsubstituted. Preferably the alkenyl group is a $C_{2-20}$ alkenyl group, more preferably a $C_{2-15}$ alkenyl group, more preferably still a $C_{2-12}$ alkenyl group, or preferably a $C_{2-6}$ alkenyl group, more preferably a $C_{2-3}$ alkenyl group. Suitable substituents include one or more groups selected from alkyl, OH, SH, $NH_2$, $CF_3$, NHalkyl, N(alkyl)$_2$, alkoxy, halogen, $N_3$, CN, $CO_2$-alkyl and $CO_2H$. Preferably, the alkenyl group is unsubstituted.

As used herein, the term "alkynyl" refers to a group containing one or more triple bonds, which may be branched or unbranched, and substituted (mono- or poly-) or unsubstituted. Preferably the alkynyl group is a $C_{2-20}$ alkynyl group, more preferably a $C_{2-15}$ alkynyl group, more preferably still a $C_{2-10}$ alkynyl group, or preferably a $C_{2-6}$ alkynyl group. Suitable substituents include one or more groups selected from alkyl, OH, SH, $NH_2$, $CF_3$, NHalkyl, N(alkyl)$_2$, alkoxy, halogen, $N_3$, CN, $CO_2$-alkyl and $CO_2H$. Preferably, the alkenyl group is unsubstituted.

As used herein, halogen includes chloro, bromo, iodo and fluoro.

In one preferred embodiment, q is 0, 1, 2 or 3, more preferably, 0 or 1. In one highly preferred embodiment, q is 0.

In one preferred embodiment, t is 0, i.e. the compound is of formula (I'), or a pharmaceutically acceptable salt or prodrug thereof,

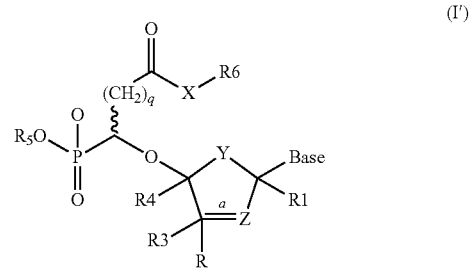

(I')

wherein:
X is selected from O and $NR_9$;
Y is a direct bond, O, S, NH, $NCH_3$, C=CH2 or $(CR_8R_{8'})_n$, where n is 1 or 2;
Z is a direct bond, $(CR_2R_{2'})_p$, where p is 1, 2, 3 or 4;
q is 0, 1, 2, 3, 4 or 5;
when p is 1, 2, 3 or 4 'a' is a single bond, or a double bond (in which case one of $R_2$ and $R_{2'}$ is absent, and one of $R_3$ and $R_{3'}$ is absent);
$R_1$, $R_2$, $R_{2'}$, $R_3$, $R_{3'}$, $R_4$, $R_8$ and $R_{8'}$ are each independently selected from H, $OR_{10}$, halogen, CN, $NR_{11}R_{12}$, $N_3$, $SR_{13}$, $C_{1-6}$-alkyl, $C_{2-6}$-alkenyl, $C_{2-6}$-alkynyl and aryl, or one of $R_2$ and $R_{2'}$ together with one of $R_3$ and $R_{3'}$ form of an epoxide;
$R_5$ is selected from H, P(=O)(OH)$_2$ and P(=O)(OH)—O—P(=O)(OH)$_2$;
$R_6$ is selected from H and $C_{1-6}$-alkyl;
$R_9$-$R_{13}$ are each independently selected from H and $C_{1-6}$-alkyl; and
Base is a natural or non-natural nucleobase.

In one preferred embodiment, the compound is of formula (Ia), or a pharmaceutically acceptable salt or prodrug thereof:

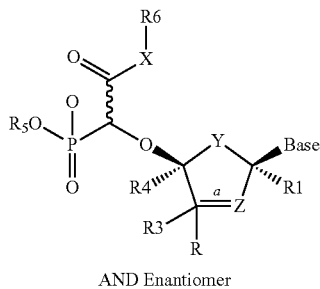

(Ia)

AND Enantiomer

In another preferred embodiment, the compound is of formula (Ib), or a pharmaceutically acceptable salt or prodrug thereof:

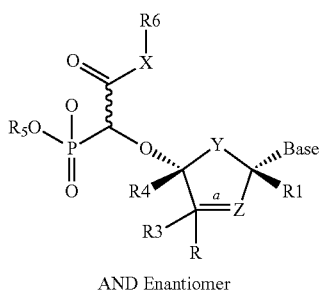

(Ib)

AND Enantiomer

In one preferred embodiment, the compound is a racemic mixture of a compound of formula (Ia) and a compound of formula (Ib).

In one preferred embodiment, the compound is a carbocyclic phosphonucleoside, i.e. a compound wherein Y is $(CR_8R_{8'})_n$. Notably the carbocyclic analogues are envisaged to more closely mimic the natural substrates than our earlier phosphononucleosides[42, 43] as they contain a core structure which is isosteric with the natural nucleoside monophosphate (see below).

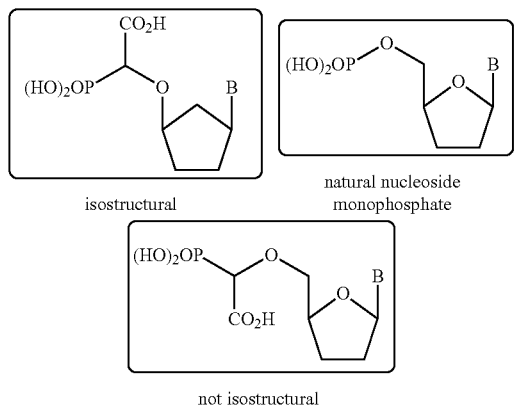

isostructural natural nucleoside monophosphate not isostructural

In one highly preferred embodiment, Y is $(CR_8R_{8'})_n$ and n is 1, i.e. the compound is a carbocyclic compound of formula (Ic), or a pharmaceutically acceptable salt or prodrug thereof,

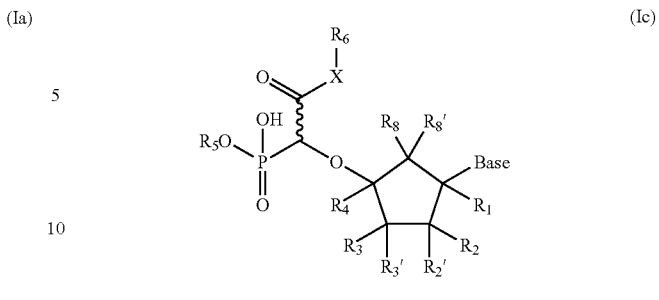

(Ic)

wherein X, $R_1$, $R_2$, $R_{2'}$, $R_3$, $R_{3'}$, $R_4$, $R_8$ and $R_{8'}$, $R_6$, $R_5$, $R_9$-$R_{13}$ and the Base are as defined above.

In one preferred embodiment, $R_8$ and $R_{8'}$ are both H, i.e. Y is $CH_2CH_2$ or $CH_2$. Even more preferably, Y is $CH_2$.

Following earlier work relating to phosphono nucleosides,[42,43] studies by the applicant have shown that a combination of the antiviral properties of 9 (see above) and its derivatives, coupled with the structural features of carbocyclic phosphononucleosides, provides a novel series of compounds 11a-e where the phosphonate bears an α-carboxylic acid substituent, that exhibit antiviral activity. These derivatives are potential monophosphate or diphosphate mimics where the α-carboxylic acid substituent may or may not act as a second phosphate mimic (or triphosphate mimic in case the α-carboxylic acid substituent may act as a γ-phosphate mimic); the monophosphorylated phosphononucleosides (both the free carboxylic acid 12 and the methyl ester 13), are also compounds of interest for evaluation as triphosphate mimics. The diphosphorylated derivatives 14 and 15 are also of interest for evaluation in the instance that the carboxylic moiety simply acts as a substituent rather than mimicking a phosphate group.

Scheme A

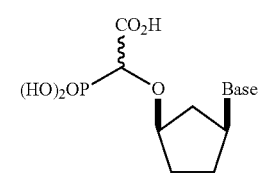

11a Base = thymine
11b Base = uracil
11c Base = cytosine
11d Base = adenine
11e Base = guanine

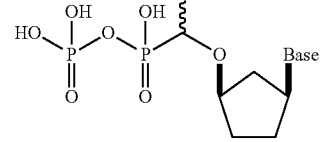

12 R = H
13 R = Me

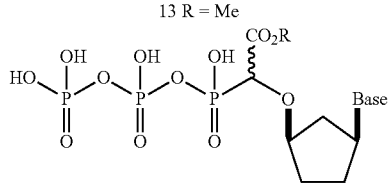

14 R = H
15 R = Me

In one preferred embodiment, the Base is a purine or pyrimidine nucleobase.

In the present context, the terms "nucleobase" covers naturally occurring nucleobases as well as non-naturally occurring nucleobases. It should be clear to the person skilled in the art that various nucleobases which previously have been considered "nonnaturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C_3$-$C_6$)-alkynylcytosine, 5-fluorouracil, 5-bromouracil, pseudoisocytosine, 2-hydroxy-S-methyl-4-triazolopyridine, isocytosine, isoguanine, inosine and the "non-naturally occurring" nucleobases described in Benner et al., U.S. Pat. No. 5,432,272. The term "nucleobase" is intended to cover every and all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

In a more preferred embodiment, the Base is a nucleobase selected from adenine (A), cytosine (C), 5-methylcytosine (MeC), isocytosine, pseudoisocytosine, guanine (G), thymine (T), uracil (U), 5-bromouracil, 5-propynyluracil, 5-fluorouracil, 5-(2-halovinyl)uracil, N-4 substituted cytosine (i.e. hydroxylamine), 5-propynyl-6-fluorouracil, 5-methylthiazole-uracil, 6-aminopurine, 2-aminopurine, inosine, 2,6-diaminopurine, 7-propyne-7-deazaadenine, 7-propyne-7-deazaguanine, 5-thiazolyluracil, 2-thiothymine, 4-thiothymine, 5-propynyl-cytosine, 5-thiazolylcytosine, phenoxazine, G-clamp, $N^2$-aminopropylguanine and 2-chloro-6-aminopurine.

In one especially preferred embodiment, the Base is a nucleobase selected from A, C, MeC, G, T, 5-fluorouracil and U.

In one preferred embodiment, X is O and $R_6$ is H or Me. The methyl ester (where $R_6$ is Me) may be a prodrug of the free carboxylic acid compound. Once in the cell, the methyl may be removed.

In one preferred embodiment p is 2, i.e. Z is $(CR_2R_{2'})_2$. In another more preferred embodiment p is 1, i.e. Z is $CR_2R_{2'}$.

In one preferred embodiment, Y is O or $(CR_8R_{8'})_n$.

In another preferred embodiment, p is 1 and Y is a direct bond.

In another preferred embodiment, Z is a direct bond and Y is O or $(CR_8R_{8'})_n$.

In one highly preferred embodiment, p is 1 and Y is O or $(CR_8R_{8'})_n$.

In another preferred embodiment, p is 1, 'a' is a double bond and $R_{2'}$ and $R_{3'}$ are both absent.

In another preferred embodiment, p is 1, 'a' is a single bond and $R_{2'}$ and $R_{3'}$ are both OH.

In one highly preferred embodiment, p is 1 and 'a' is a single bond.

More preferably, X is O and $R_6$ is H.

In one preferred embodiment, $R_5$ is H.

In one preferred embodiment, $R_1$, $R_2$, $R_{2'}$, $R_3$, $R_{3'}$, $R_4$, $R_8$ and $R_{8'}$ are all H.

In one preferred embodiment, the compound is of formula (Id), or a pharmaceutically acceptable salt or prodrug thereof:

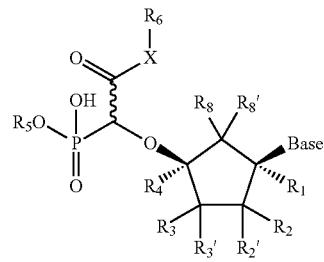

(Id)

In one particularly preferred embodiment, the compound is of formula (Ie), or a pharmaceutically acceptable salt or prodrug thereof:

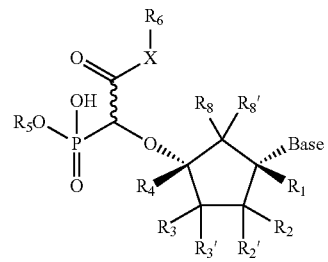

(Ie)

In one preferred embodiment, the compound is a racemic mixture of a compound of formula (Id) and a compound of formula (Ie).

In one particularly preferred embodiment, the compound of the invention is selected from the following:

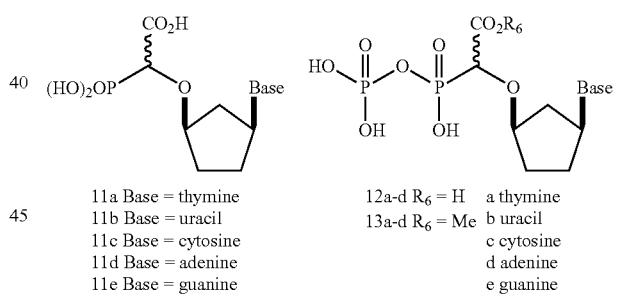

11a Base = thymine
11b Base = uracil
11c Base = cytosine
11d Base = adenine
11e Base = guanine 12a-d $R_6$ = H    a thymine
13a-d $R_6$ = Me   b uracil
                   c cytosine
                   d adenine
                   e guanine and pharmaceutically acceptable salts and prodrugs thereof.

In an even more preferred embodiment, the compound of the invention is selected from the following:

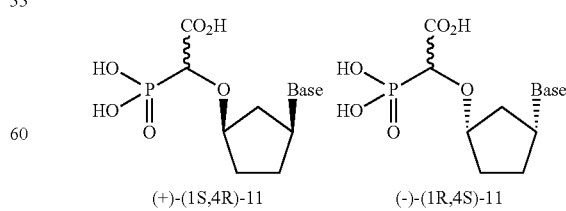

(+)-(1S,4R)-11          (-)-(1R,4S)-11 wherein the Base is selected from thymine, uracil, cytosine, adenine and guanine, and pharmaceutically acceptable salts and prodrugs thereof.

In one highly preferred embodiment, the compound is (−)-(1R,4S)-11.

In one preferred embodiment, the compound of the invention is capable of inhibiting HIV-RT in a cell free HIV-RT assay. More specifically, the compound of the invention is capable of inhibiting the HIV-RT catalysed incorporation of [$^3$H]dNTP into a homopolymeric or heteropolymeric template/primer. Further details of this assay are set forth in the accompanying Examples section. In one particularly preferred embodiment, the compound of the invention exhibits an IC$_{50}$ value in this assay of less than about 100 μg/ml, more preferably, less than about 50 μg/ml, even more preferably, less than about 20 μg/ml, more preferably still, less than about 10 μg/ml, even more preferably, less than about 5 μg/ml or 2 μg/ml. In one highly preferred embodiment, the compound of the invention exhibits an IC$_{50}$ value in this assay of less than about 1 μg/ml, even more preferably, less than about 0.5 μg/ml, more preferably still, less than about 0.1 μg/ml.

In one aspect the compound of formula (I) may have the following

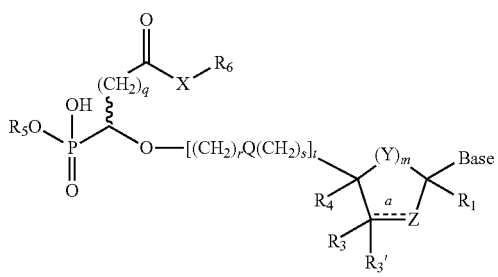

(I)

wherein:
X is selected from O and NR$_9$;
Y is O or (CR$_8$R$_{8'}$)$_n$, where n is 1 or 2;
Z is (CR$_2$R$_{2'}$)$_p$, where p is 0 or 1;
Q is selected from O, S, CH$_2$, CH=CH and C≡C;
m is 0 or 1;
r is 0, 1, 2 or 3;
s is 0, 1, 2 or 3;
t is 0 or 1;
q is 0, 1, 2, 3, 4 or 5;
when p is 1, 'a' is a single bond or a double bond;
R$_1$, R$_2$, R$_{2'}$, R$_3$, R$_{3'}$, R$_4$, R$_8$ and R$_{8'}$ are each independently selected from H, OR$_{10}$, halogen, CN, NR$_{11}$R$_{12}$, N$_3$, SR$_{13}$, C$_{1-6}$-alkyl, C$_{2-6}$-alkenyl, C$_{2-6}$-alkynyl and aryl, or when 'a' is a double bond, one of R$_2$ and R$_{2'}$ is absent, and one of R$_3$ and R$_{3'}$ is absent;
R$_5$ is selected from H, P(=O)(OH)$_2$ and P(=O)(OH)—O—P(=O)(OH)$_2$;
R$_6$ is selected from H and C$_{1-6}$-alkyl;
R$_9$-R$_{13}$ are each independently selected from H and C$_{1-6}$-alkyl; and
Base is a natural or non-natural nucleobase.

Therapeutic Use

The compounds of the invention have been found to inhibit viral enzymes required for virus replication, in particular, reverse transcriptase, and thus have potential therapeutic applications in the treatment of viral disorders.

Thus, one aspect of the invention relates to a compound of formula (I), or a pharmaceutically acceptable salt or prodrug thereof, for use in treating or preventing a viral disorder.

Another aspect of the invention relates to the use of a compound of the invention, or a pharmaceutically acceptable salt thereof, in the preparation of a medicament for treating or preventing a viral disorder.

A further aspect of the invention relates to a method of treating a viral disorder, said method comprising administering to a subject in need thereof, a compound of the invention or a pharmaceutically acceptable salt or prodrug thereof. Preferably, the viral disorder is an RNA- or DNA-dependent viral disorder.

As used herein the phrase "preparation of a medicament" includes the use of one or more of the above described compounds directly as the medicament in addition to its use in a screening programme for further anti-viral agents or in any stage of the manufacture of such a medicament.

One preferred embodiment therefore relates to the use of one or more compounds of the invention in the treatment of a viral disorder. Preferably, the viral disorder is an RNA virus or a DNA virus.

In one preferred embodiment, the viral disorder is an RNA virus.

In one preferred embodiment, the viral disorder is a DNA virus.

In one preferred embodiment, the virus is selected from human cytomegalovirus (HCMV), herpes simplex virus type 1 (HSV-1) and type 2 (HSV-2), human immunodeficiency virus type 1 (HIV-1) and type 2 (HIV-2), HTLV-I or II, varicella-zoster virus (VZV), respiratory viruses such as influenza virus (INF) and respiratory syncytial virus (RSV), flaviviruses (i.e. Dengue virus, hepatitis C virus), hepatitis B virus, coronavirus.

In one especially preferred embodiment, the virus is HIV-1.

As defined herein, an antiviral effect within the scope of the present invention may be demonstrated by the ability to inhibit HIV-RT in a cell-free HIV-RT assay. This assay, including methods for its performance, is described in more detail in the accompanying Examples. Using such assays it may be determined whether a compound is antiviral in the context of the present invention.

In one preferred embodiment, the compound is capable of inhibiting HIV-1-RT-catalysed incorporation of [$^3$H]dTTP in a poly rA/oligo dT template/primer.

In one preferred embodiment, the compound is capable of inhibiting HIV-1-RT-catalysed incorporation of [$^3$H]dCTP in a poly rI/oligi dC template/primer.

In one preferred embodiment, the compound is capable of inhibiting HIV-1-RT-catalysed incorporation of [$^3$H]dATP in a poly rU/oligo dA template/primer.

In one embodiment, the compound of the invention is administered in an amount sufficient to inhibit HIV-1-RT in a cell free HIV-RT assay.

The compounds 11a-d, (+)-11a-d and (−)-11a-d and 26a, (+)-26a and (−)-26a were evaluated using a cell-free HIV-1-RT assay and, significantly, a number of the compounds were found to strongly inhibit HIV-1 RT (Table 5). Most notably, when examined as potential inhibitors of HIV-1-RT-catalysed incorporation of [$^3$H]dTTP in a poly rA/oligo dT template/primer, the (−) enantiomers of 11a and 11 b, corresponding to the "unnatural" L-thymine and L-uracil nucleosides, displayed potent inhibitory activity, and were considerably more active than their (+)-11a and (+)-11b counterparts. The thymine derivative 11a and uracil derivative 11b showed no marked, if any inhibition of the incorporation of [$^3$H]dCTP in poly rI/oligo dC and of [$^3$H]dATP in poly rU/oligo dA at 200 μg/mL, pointing to a specific competition with [$^3$H]dTTP but not with [$^3$H]dCTP or

[³H]dATP. Likewise, the cytosine derivative (−)-11c displayed strong inhibition in the [³H]dCTP-poly rI/dC system but not in the other systems. Finally, the adenine derivative 11d proved to be a potent inhibitor of HIV-1 RT in the [3H]dATP-poly rU/dA system but not in the other systems. In all cases, the (−)-enantiomer was by far superior to the (+)-enantiomer, pointing to a high degree of enantiospecificity of these compounds for HIV-1 RT inhibition.

TABLE 5

Inhibitory activity of the compounds against HIV-1 reverse transcriptase using different template/primers and natural dNTP substrates

| Compound | IC$_{50}$$^a$ (µg/ml) | | |
|---|---|---|---|
| | [³H]dTTP/ polyrA.dT | [³H]dCTP/ polyrI.dC | [³H]dATP/ polyrU.dA |
| 11a | 0.15 ± 0.03 | >200 | 107 ± 8 |
| (+)-11a | 13 ± 2 | >200 | 35 ± 23 |
| (−)-11a | 0.15 ± 0.00 | >200 | 58 ± 55 |
| 11b | 1.3 ± 0.7 | >200 | 74 ± 55 |
| (+)-11b | 40 ± 37 | >200 | 56 ± 21 |
| (−)-11b | 1.1 ± 0.6 | >200 | 78 ± 27 |
| 11c | 77 ± 43 | 1.6 ± 0.4 | 36 ± 2 |
| (+)-11c | 7.8 ± 6.2 | 134 ± 43 | 18 ± 1 |
| (−)-11c | 60 ± 8 | 1.5 ± 0.1 | 17 ± 0 |
| 11d | ≥200 | >200 | 0.098 ± 0.019 |
| (+)-11d | 174 ± 1 | >200 | 12 ± 3 |
| (−)-11d | >200 | >200 | 0.072 ± 0.042 |
| AZT-TP | 0.035 ± 0.016 | — | — |
| ddCTP | — | 5.0 ± 0.4 | — |
| ddATP | — | — | 0.55 ± 0.09 |

$^a$Fifty percent inhibitory concentration, or compound concentration required to inhibit HIV-RT catalysed incorporation of [³H]dNTP in the homopolymeric template/primer.

TABLE 6

| | IC50 (µM) (µg/ml) | | |
|---|---|---|---|
| | HIV-1 RT (PolyrA.dT) | CMV-DNA Pol (calf thymus DNA) | HSV-1 DNA Pol (calf thymus DNA) |
| (−)-11a | 0.15 ± 0.00 | 15 ± 4 | 9.7 ± 7.4 |
| (+)26a | >200 | >200 | >200 |
| (−)26a | >200 | >200 | >200 |
| 32 | — | | |
| 33 | 0.68 ± 0.42 | | |
| 35 | 186 | | |
| 39 | 0.90 ± 0.30 | 1.2 | <2 |
| 41 | 1.4 ± 0.0 | 0.4 | <2 |
| 60 | >200 | | |
| PFA | 0.34 ± 0.01 | 8.6 | 0.16 | a) 50% inhibitory concentration. [3H]dTTP is used as the radiolabled substrate. Template is indicated between brackets.

McClure et al. compared the anti-HIV activity of 6 licensed NRTIs using a cell-free HIV-RT assay.[44] Although not a direct comparison, the results reported by McClure indicate that our most active phosphononucleoside derivative (−)-11a (IC$_{50}$=0.15 µg/mL), possesses greater anti-HIV-RT activity than all of the NRTIs (IC$_{50}$=0.316-10 µg/mL) tested in their study with the exception of AZT (IC$_{50}$=0.1 µg/mL). This is a good indication of the remarkable potency of a number of the novel phosphononucleoside derivatives 11a-d.

Pharmaceutical Compositions

A further aspect of the invention relates to a pharmaceutical composition comprising a compound of the invention admixed with one or more pharmaceutically acceptable diluents, excipients or carriers. Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, 2$^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Salts/Esters

The compounds of the invention can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the compounds of the present invention. The terms used in the claims encompass these forms.

Polymorphs

The invention furthermore relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes the compounds of the present invention in prodrug form. Such prodrugs are generally compounds of the invention wherein one or more appropriate groups have been modified such that the modification may be reversed upon administration to a human or mammalian subject. Such reversion is usually (but not necessarily) performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

In one preferred embodiment of the invention, the prodrug is selected from a phosphoramidate derivative, a SATE (S-acyl-2-thioethyl) ester derivative, a pivaloyloxymethyl (POM) derivative, an isopropyloxymethylcarbonyl (POC) derivative and a cycloSal derivative, an alkyloxyalkyl derivative.

Suitable phosphoramidate derivatives will be familiar to a person skilled in the art and include, by way of example, compounds of formula (II),

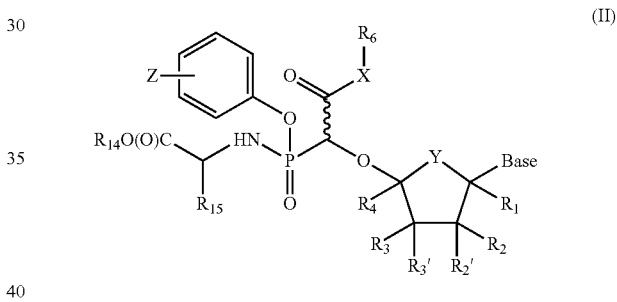

wherein $R_{15}$ is any side chain of an amino acid (more preferably, alkyl), $R_{14}$ is alkyl or aryl, Z is an optional substituent (for example one or more groups selected from alkyl, OH, SH, $NH_2$, $CF_3$, NH-alkyl, N(alkyl)$_2$, alkoxy, $N_3$, $NO_2$, halogen, CN, $CO_2$-alkyl and $CO_2H$).[45]

In an alternative preferred embodiment, the prodrug is of formula (III),

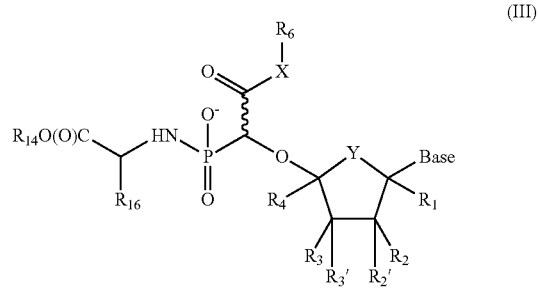

where $R_{14}$ is alkyl or aryl, and $R_{16}$ is any side chain of an amino acid (more preferably alkyl).[46]

Suitable POM derivatives[47] will be familiar to a person skilled in the art and include, by way of example, compounds of formula (IV):

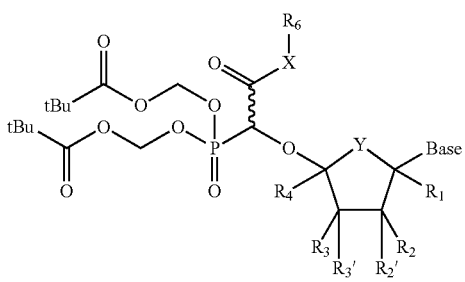

(IV)

Suitable SATE derivatives[48] will be familiar to a person skilled in the art and include, by way of example, compounds of formula (V):

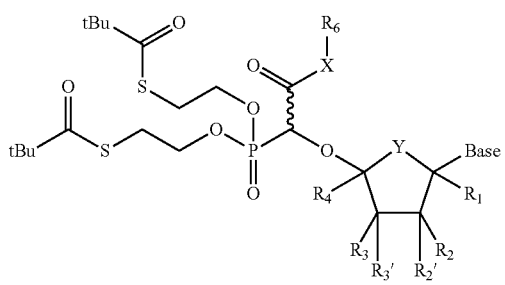

(V)

Suitable POC derivatives[49] will be familiar to a person skilled in the art and include, by way of example, compounds of formula (VI):

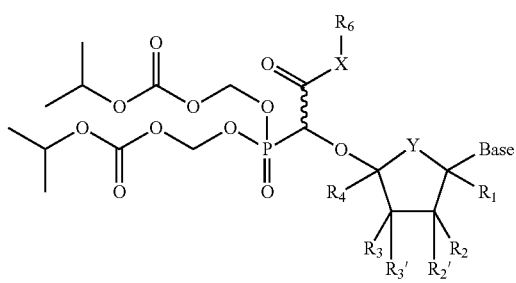

(VI)

Suitable cycloSal type derivatives[50] will be familiar to a person skilled in the art and include, by way of example, compounds of formula (VII),

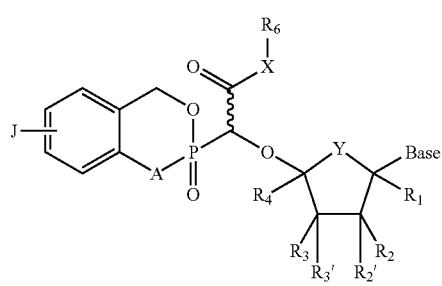

(VII)

wherein A is O ("cycloSal" derivatives) or NH ("cycloAMb" derivatives), and J is a substituent selected from $C_{1-6}$-alkyl and halogen, wherein the alkyl group is optionally further substituted with one or more additional groups, including alkyloxy, $CO_2$-alkyl, OCO-alkyl, $CO_2CH_2OCO$-alkyl and $CO_2CH_2OCOO$-alkyl. Preferably, A is O.

Preferably, the substituent J is selected from Me, methoxy, $^tBu$, $CH_2CH_2CO_2C_{1-6}$-alkyl, $CH_2CH_2OCOC_{1-6}$-alkyl, $CH_2CH_2CO_2CH_2OCOC_{1-6}$-alkyl and $CH_2CH_2CO_2CH_2OCOOC_{1-6}$-alkyl.

In one highly preferred embodiment, the cycloSal moiety is selected from the following, wherein the wavy line represents the point of attachment to the rest of the molecule:

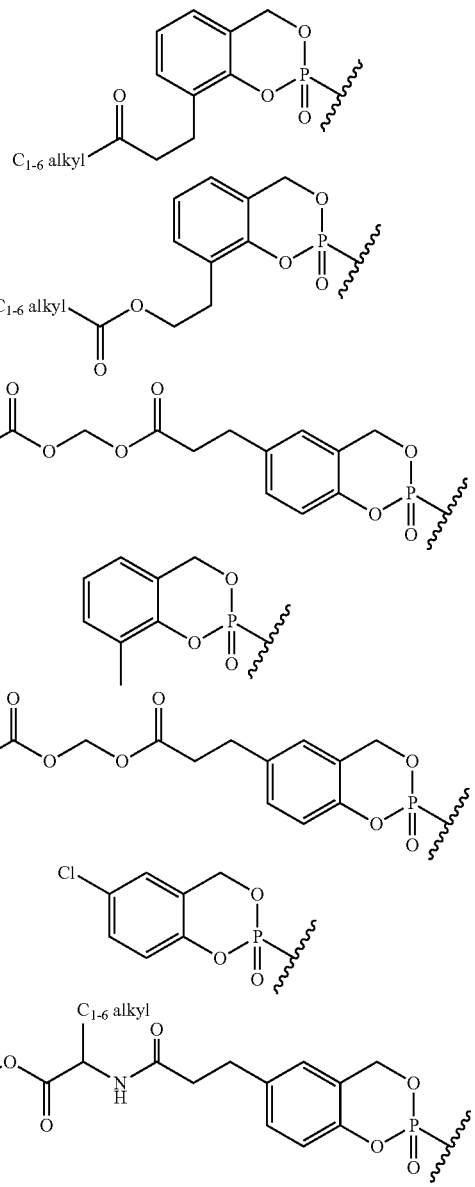

where $C_{1-6}$-alkyl is, for example, Me or $^tBu^{51}$ or any side chain of an amino acid.

Other nucleoside prodrugs such as the alkoxyalkyl derivatives will be familiar to the person skilled in the art[52].

Administration

The pharmaceutical compositions of the present invention may be adapted for oral, rectal, parenteral, intramuscular, intraperitoneal, intraarterial, intrathecal, intrabronchial, subcutaneous, intradermal, intravenous, nasal, vaginal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, vaginal rings, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight.

In an exemplary embodiment, one or more doses of 10 to 300 mg/day or more preferably, 10 to 150 mg/day, will be administered to the patient for the treatment of a viral disorder.

Combinations

In a particularly preferred embodiment, the one or more compounds of the invention are administered in combination with one or more other active agents, for example, existing antiviral drugs or pharmacological enhancers available on the market. In such cases, the compounds of the invention may be administered consecutively, simultaneously or sequentially with the one or more other active agents.

Antiviral drugs in general are more effective when used in combination. In particular, combination therapy is desirable in order to avoid an overlap of major toxicities, mechanism of action and afford complementary resistance mechanism(s). Furthermore, it is also desirable to administer most drugs at their maximum tolerated doses with minimum time intervals between such doses. The major advantages of combining drugs are that it may promote additive or possible synergistic effects through biochemical interactions and also may decrease the emergence of resistance.

Assays

Another aspect of the invention relates to the use of a compound of the invention as defined hereinabove in an assay for identifying further candidate compounds that are capable of inhibiting HIV-1-RT.

More preferably, the assay is a competitive binding assay.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, fixed on a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Synthesis

A further aspect of the invention relates to a process for preparing a compound of formula (If) or (Ig), wherein $R_6$ is H or $C_{1-6}$-alkyl, and the Base is a natural or non-natural nucleobase, said process comprising the steps of:

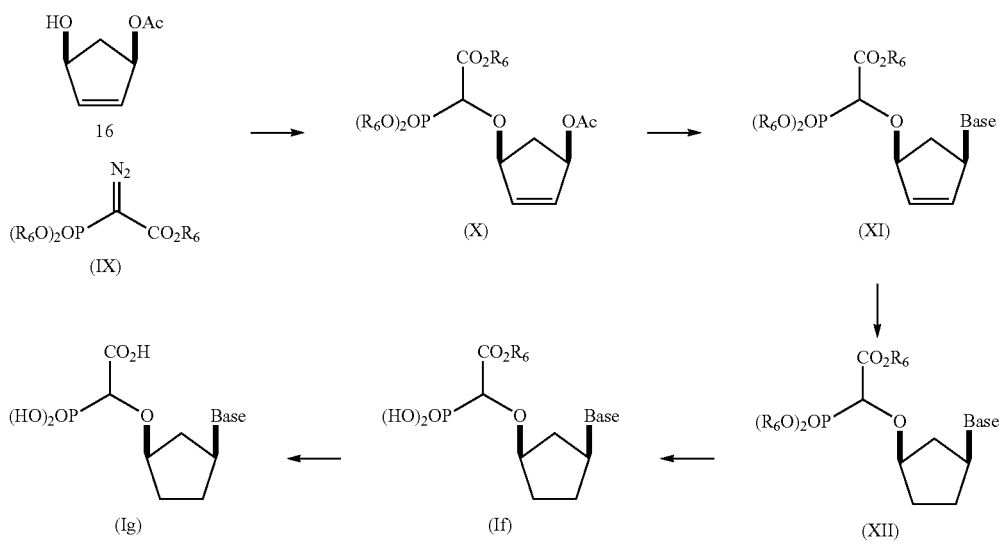

(i) reacting a compound of formula 16 with a compound of formula (IX) in the presence of a rhodium (II) acetate or copper (II) triflate catalyst to form a compound of formula (X);
(ii) reacting said compound of formula (X) with a Base in the presence of a palladium(0) catalyst in a suitable solvent to form a compound of formula (XI);
(iv) hydrogenating said compound of formula (XI) in the presence of palladium on charcoal to form a compound of formula (XII);
(v) treating said compound of formula (XII) with TMSBr in MeCN to form a compound of formula (If); and
(vi) optionally hydrolysing said compound of formula (If) to form a compound of formula (Ig).

Two strategies can be envisaged for the approach to compounds of formula (I): O—H insertion on the cyclopentanol core prior to introduction of the nucleoside base, or alternatively insertion of the base initially followed by O—H insertion. The latter approach is feasible but necessitates the use of more protecting groups to block competing reaction of the carbene at the electron-rich base.

O—H Insertion Reactions

The applicant has recently reported that rhodium-catalysed O—H insertion provides a mild and neutral way of attaching the phosphonate group to suitably protected nucleosides.[42,43] The O—H insertion reactions were carried out using triethyl and trimethyl phosphono-diazoacetate in the presence of rhodium(II) acetate or copper(II) triflate, as summarised in Table 1.

TABLE 1

O—H insertion reactions.

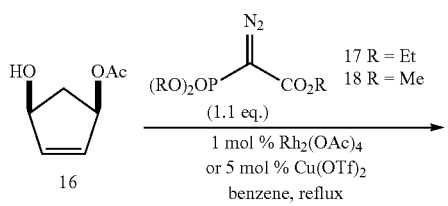

TABLE 1-continued

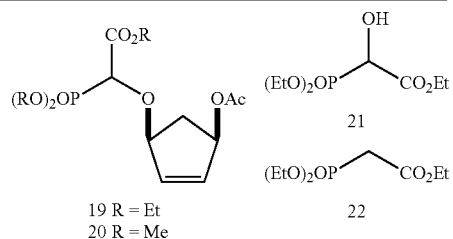

| Entry | Diazo | Catalyst | Time (h) | Yield (%) |
|---|---|---|---|---|
| 1 | 17 | Cu(OTf)$_2$ | 18 | 78 |
| 2 | 18 | Cu(OTf)$_2$ | 22 | 78 |
| 3 | 17 | Rh$_2$(OAc)$_4$ | 19 | 77 |
| 4 | 18 | Rh$_2$(OAc)$_4$ | 6 | 92 |

Use of both the methyl and ethyl esters was explored with a view to exploiting the different rates of hydrolysis in the deprotection sequence, potentially leading to selective hydrolysis of the phosphonate without cleaving the carboxylic ester. Initially the reactions were heated at reflux overnight (17-24 h). It was later determined that the reactions are essentially complete within 4-5 h. However, longer reaction time does not deleteriously impact on the yield. The O—H insertion reactions proceed smoothly, with clean conversion to the desired products as can be seen from the $^1$H NMR spectrum of the crude product. The $^1$H NMR spectrum of the crude material contains minor amounts of the water insertion product 21 (2%, d at 4.3 ppm $J_{PH}$=18.6) and the reduced product 22 (4%, d at 3.0 ppm $J_{PH}$=21.6) and the desired product 20 is present in ~90 mol %. In the case of the triethyl derivative 19 the O—H insertion reaction worked equally well when either copper(II) triflate (entry 1) or rhodium(II) acetate (entry 3) were employed as catalyst, with yields of 77-78% following purification by flash chromatography on silica gel. However, in the case of the trimethyl derivative 20, rhodium(II) acetate appears to give marginally better yields (92%, entry 4) compared with copper(II) triflate (78%, entry 2). These reactions were carried out many times and the results were entirely reproducible. This work demonstrates that the O—H insertion reaction can be carried out on a multigram scale in excellent yield using both the triethyl and trimethyl diazophosphonates 17 and 18. While the triethyl derivative 19 can be purified by flash chromatography on silica gel using diethyl ether as eluant, efforts to purify the corresponding trimethyl derivative 20 using this eluant failed and the compound remained on the column. However, 20 is readily eluted using 5% methanol in dichloromethane.

Each of the products 19 and 20 is formed as equimolar mixtures of diastereomers, readily identified spectroscopically from the characteristic signals in the $^1$H and $^{13}$C NMR spectra for the CH adjacent to the phosphorus.

Base Insertion Reactions

The introduction of the nucleobases onto the allylic acetate 19 was next undertaken. Other nucleobases than those reported herein, can be introduced using similar methodology. Tsuji-Trost type palladium(0) catalysed allylic substitution offers a mild method for the attachment of the nucleobases and has the added advantage of regio- and stereoselectivity.[53-56] Extensive optimisation was undertaken with variation of the palladium catalyst and reaction conditions and ultimately insertion of each of the bases to afford the desired series of phospononucleoside derivatives 23 and 24 was achieved, as summarised in Table 2.

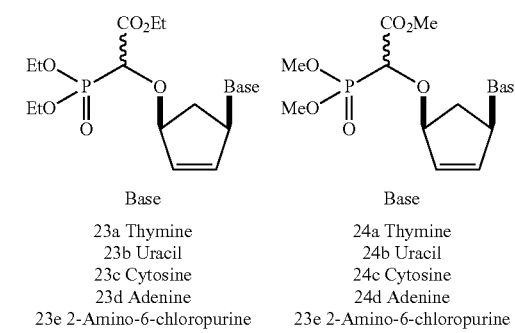

Base
23a Thymine
23b Uracil
23c Cytosine
23d Adenine
23e 2-Amino-6-chloropurine

Base
24a Thymine
24b Uracil
24c Cytosine
24d Adenine
23e 2-Amino-6-chloropurine

TABLE 2

Palladium-catalysed base insertion reactions

| Entry | acetate | base | product | conditions | yield[a] |
|---|---|---|---|---|---|
| 1 | 19 | T | 23a | Pd(PPh$_3$)$_4$, MeCN, Na$_2$CO$_3$ 66° C. 15 h | 35 |
| 2 | 19 | U | 23b | Pd(PPh$_3$)$_4$, MeCN, Na$_2$CO$_3$ 66° C., 15 h | 45 |
| 3 | 19 | U | 23b | Pd$_2$(dba)$_3$•CHCl$_3$, dppb, MeCN, Na$_2$CO$_3$ 55° C. 20 h | 57 |

TABLE 2-continued

Palladium-catalysed base insertion reactions

| Entry | acetate | base | product | conditions | yield[a] |
|---|---|---|---|---|---|
| 4 | 19 | C | 23c | Pd$_2$(dba)$_3$•CHCl$_3$, dppb, DMF, Na$_2$CO$_3$ 55° C. 28 h | 39 |
| 5 | 19 | A | 23d | Pd$_2$(dba)$_3$•CHCl$_3$, dppb, DMF, Na$_2$CO$_3$ 55° C. 26 h | 49 (19:1)[b] |
| 6 | 19 | A | 23d | Pd$_2$(dba)$_3$•CHCl$_3$, dppb, MeCN, Na$_2$CO$_3$ 55° C. 24 h | 62 (6:1)[b] |
| 7 | 19 | A | 23d | Pd$_2$(dba)$_3$•CHCl$_3$, dppb, MeCN, Cs$_2$CO$_3$ 55° C. 24 h | 58 (18:1)[b] |
| 8 | 20 | T | 24a | Pd(PPh$_3$)$_4$, MeCN, Na$_2$CO$_3$ 66° C. 24 h | 51 |
| 9 | 20 | T | 24a | Pd(dba)$_2$, dppb, MeCN, Na$_2$CO$_3$, 50° C. 5.5 h | 55 |
| 10 | 20 | U | 24b | Pd(dba)$_2$, dppb, MeCN, Na$_2$CO$_3$, 50° C. 5.5 h | 64 |
| 11 | 20 | C | 24c | Pd(dba)$_2$, dppb, MeCN, Na$_2$CO$_3$ 55° C. 3 h | 39 |
| 12 | 20 | A | 24d | Pd(dba)$_2$, dppb, MeCN, Na$_2$CO$_3$ 55° C. 2.5 h | 43 |
| 13 | 20 | 2-amino-6-chloropurine | 24e | Pd(dba)$_2$, dppb, MeCN, Cs$_2$CO$_3$ 50° C. 6.5 h | N-7 35 N-9 14 |
| 14 | 19 | T | 23a | Pd(PPh$_3$)$_4$, MeCN, Na$_2$CO$_3$ 55° C., microwave, 45 min | 38 |
| 15 | 19 | C | 23c | Pd(PPh$_3$)$_4$, MeCN, Na$_2$CO$_3$ 55° C., microwave, 45 min | 23 |
| 16 | 20 | A | 24d | Pd(dba)$_2$, dppb, MeCN, Na$_2$CO$_3$ 55 C., microwave, 45 min | 57 |

[a]isolated yield after chromatography.
[b]Crude N9:N7 ratio

It is clear from the results outlined in Table 2 that, for the pyrimidine derivatives 24a-c, the use of Pd(dba)$_2$ or Pd$_2$(dba)$_3$.CHCl$_3$ and dppb ligand generates superior yields relative to Pd(PPh$_3$)$_4$, and, while the yields with Pd(PPh$_3$)$_4$ varied considerably depending on the batch and age of the catalyst used, the yields obtained with Pd$_2$(dba)$_3$CHCl$_3$ or Pd(dba)$_2$ as catalyst were reproducible. In general, the use of Pd(dba)$_2$ or Pd$_2$(dba)$_3$CHCl$_3$ with dppb and a reaction temperature of 50-55° C. led to less of the unwanted hydroxyphosphonate side product 21 than when Pd(PPh$_3$)$_4$ was employed. Notably, all five nucleoside derivatives 24a-e can be reproducibly prepared in moderate to good yield using Pd(dba)$_2$/dppb as catalyst (Table 2, entries 9-13).

The base insertion reaction was also carried out under microwave irradiation with a view to reducing reaction times and improving the reaction efficiency. The reactions were found to be essentially complete within 45 min stirring at 55° C. in the microwave, confirming acceleration of the reaction under these conditions (Table 2, entries 14-16). However, in general, slightly lower yields were generally observed relative to the thermal reactions. It is essential to purge the mixture with nitrogen prior to sealing the microwave tube in order to ensure the reaction proceeds well. In general these microwave reactions were carried out on 100-200 mg scale, however, the reaction with the adenine derivative 23 was carried out using 1.5 g of the allylic acetate 17 and was again essentially complete in 45 min (Table 2, entry 16).

Characterisation, Purification and Stability of the Phosphononucleosides

In all cases the diastereomeric ratio of the crude product of the base insertion reaction was the same as that of the starting allylic acetate. This is evident from numerous examples where the diastereomeric ratio of the starting allylic acetate deviates from 1:1 where it is seen that the diastereomeric ratio is unaffected by the palladium mediated reaction. As previously observed for the products of the O—H insertion, the majority of $^1$H and $^{13}$C NMR signals are quite well distinguished for the two individual diastereomers. Purification of these compounds is straightforward and the nucleosides are readily separated from the impurities present in the crude product by flash chromatography on silica gel. While the thymine and uracil derivatives 23a-b and 24a-b eluted using 5% methanol in dichloromethane, the cytosine, adenine and 2-amino-chloropurine derivatives 23c-d and 24c-e required a more polar solvent system of 10% methanol in dichloromethane to elute the pure nucleosides. The stability of the nucleosides differ considerably and in general the triethyl derivatives are more stable than the corresponding trimethyl nucleosides. The triethyl and trimethyl derivatives 23a-d and 24a-b are stable, and can be left at room temperature neat or in solution for extended periods without any detectable decomposition. However, the trimethyl derivatives 24c-e were found to be much more labile. In particular the trimethyl cytosine derivative 24c was found to be labile in solution leading to a complex mixture of unidentifiable products.

Hydrogenation Reactions

Prior to exploring the deprotection reaction, saturation was first undertaken as it was expected that the saturated compounds 25a-d and 26a-d would be more stable than their allylic counterparts 23a-d and 24a-d. These saturated compounds were accessed by hydrogenation at 30-50 psi over palladium on carbon catalyst (Table 3). The hydrogenation reaction proceeded well for the pyrimidine derivatives (Table 3, entries 1-3) with yields of 80-95% after purification. For the thymine and uracil derivatives 25a-b and 26a-b the reaction is complete within 1.5 h at 20-30 psi and is essentially quantitative, although these compounds were isolated in slightly lower yields following chromatography. The cytosine derivatives 25c and 26c required slightly longer reaction times or increased catalyst loading and were accessed in lower yields than the thymine and uracil derivatives. The adenine derivatives 25d and 26d also required more forcing conditions.

TABLE 3

Hydrogenation of phosphononucleoside derivatives 23a-d and 24a-e.

23a-d R = Et
23a-d R = Me a Base = thymine
b Base = uracil
c Base = cytosine
d Base = adenine
e Base = 2-amino-6-chloropurine 25a-d R = Et
25a-d R = Me

| Starting material | Product | Pd/C % wt/wt | | Pressure (psi) | Time (h) | Yield (%) |
|---|---|---|---|---|---|---|
| 23a | 25a | 5 | EtOH | 30 | 3 | 89 |
| 23b | 25b | 10 | EtOH | 30 | 2.5 | 82 |
| 23c | 25c | 5 | EtOH | 25 | 18 | 82 |
| 23d | 25d | 5 | EtOH | 25 | 20 | 77 |
| 24a | 26a | 10 | MeOH | 30 | 2.5 | 92 |
| 24b | 26b | 5 | MeOH | 30 | 1.5 | 94 |
| 24c | 26c | 5 | MeOH | 25 | 15 | 80 |
| 24d | 26d | 5 | MeOH | 30 | 19 | 80 |
| 24e | 26e | 10 | MeOH | 50 | 26 | 10* |

*90% pure by $^1$H NMR, 10% of alklene 24e, N-7 isomer.

Deprotection Reactions

The deprotection of the triethyl thymine derivative 25a was first attempted using TMSBr (Scheme 1).[57] The phosphononucleoside 25a was treated with 7 equivalents of TMSBr at 0° C., allowed to return slowly to room temperature and then stirred overnight. Water was added to hydrolyse the resulting silyl esters, and the reaction mixture was concentrated (Scheme 1). $^1$H NMR analysis of the resulting residue confirmed that the phosphonate esters had been fully cleaved and the carboxylic ester moiety had remained intact to provide 27a.

Scheme 1. Deprotection of 25a

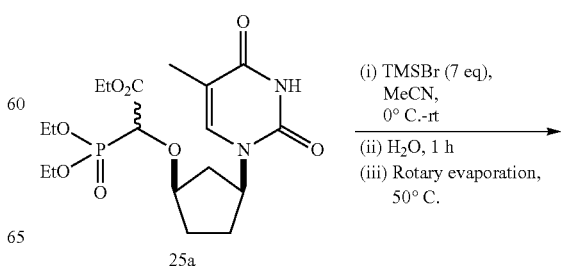

25a

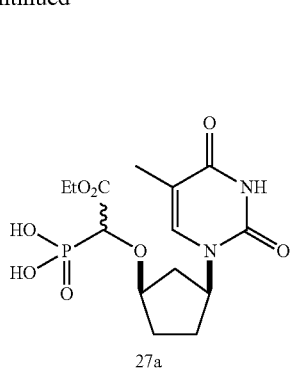

27a

↓ H₂O
microwave
140° C.,
15 min

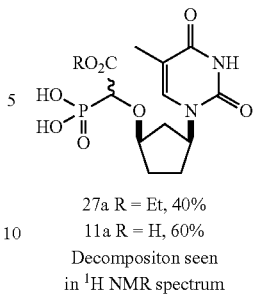

27a R = Et, 40%
11a R = H, 60%
Decompositon seen in ¹H NMR spectrum

← H₂O, reflux, 2 days

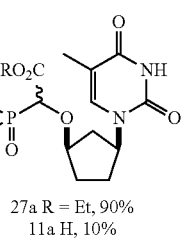

27a R = Et, 90%
11a H, 10%

A general procedure was devised that could be successfully applied to all four derivatives 26a-d (Scheme 2), which is essentially the same procedure we reported for the deprotection of the nucleoside series.[42,43] The derivatives were treated with excess TMSBr, followed by addition of water and then treatment with aqueous NaOH (1M, 10 equiv.) at 50° C. (Scheme 2). In the case of the adenine derivative, invariably a small amount of the carboxylic methyl ester remained intact (~5%) even after prolonged stirring with aqueous NaOH at 50° C. (3 days). The presence of excess base does not have a negative impact on the purity of the fully deprotected products 11a-d.

Scheme 2 General procedure for the deprotection of phosphononucleosides 26a-d.

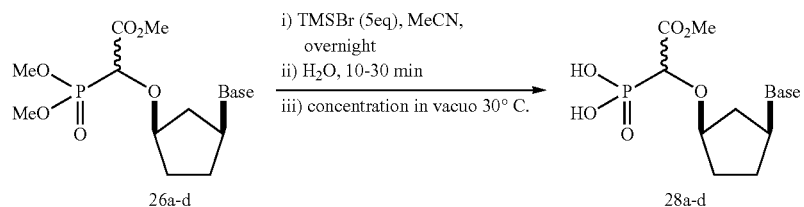

(i) 1M NaOH (10 equiv), H₂O, 50° C.
(ii) aq. NH₃, charcoal column

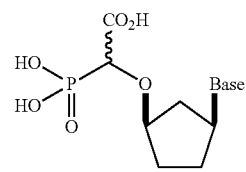

11a-d
(isolated as ammonium salts)
a thymine 57%
b uracil 58%
c cytosine 66%
d adenine 71%

Due to their potential in the synthesis of prodrugs with lipophilic side chains, the isolation of the partially deprotected 28a-d was also investigated (Scheme 3). The compounds 28a-d were also isolated following treatment with TMSBr (5 equiv.) and were found to be stable for extended periods when stored at neutral pH or as their ammonium salts. To prevent the HBr generated in the reaction from cleaving the carboxy ester it is important to adjust the pH of the reaction mixture to 7 with 10% sodium hydroxide before removing the water at a temperature below 30° C. through co-evaporation with acetonitrile. Concentration in vacuo at a higher temperature results in partial hydrolysis of the carboxylic ester. The compound 28a was isolated in as the ammonium salt in 45% yield following charcoal chromatography; the sodium salts of compounds 28b-d were isolated in quantitative yields prior to charcoal chromatography.

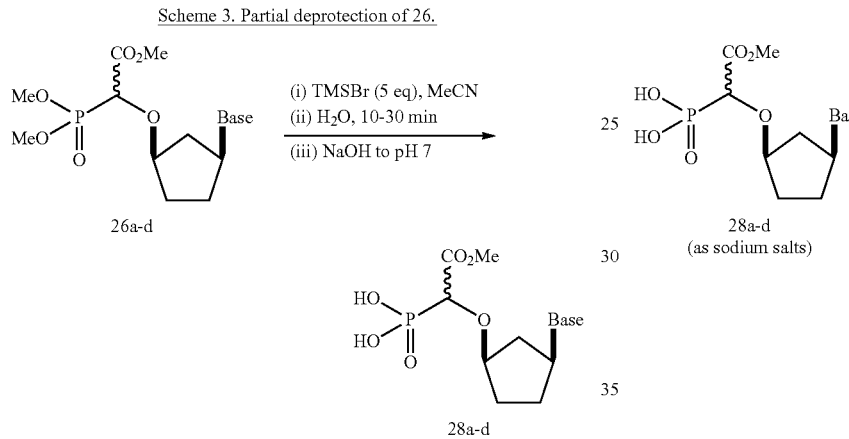

Scheme 3. Partial deprotection of 26.

26a-d (i) TMSBr (5 eq), MeCN
(ii) $H_2O$, 10-30 min
(iii) NaOH to pH 7

28a-d

The novel phosphononucleosides 11a-d were purified using charcoal chromatography (Scheme 4). The fully deprotected compounds 11a-d are not stable in acidic solutions, therefore in each case the material isolated from the base-catalysed deprotection was dissolved in the minimum amount of water and the solution was adjusted to pH 1-2.5 immediately prior to adsorption onto the charcoal column. The charcoal pad was then washed with water to remove inorganic impurities followed by 20% aqueous ammonia to release the pure phosphononucleoside as its ammonium salt. The ammonium salts of 11a-d were isolated in this way in 57-71% yield, as clear or pale pink gums. Following lyophilisation, these salts are isolated as fine white solids that can be stored for over a year at room temperature without noticeable decomposition.

Scheme 4

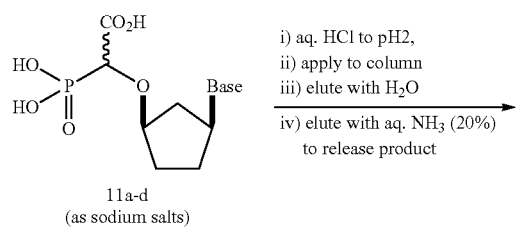

11a-d
(as sodium salts)

i) aq. HCl to pH2,
ii) apply to column
iii) elute with $H_2O$
iv) elute with aq. $NH_3$ (20%) to release product

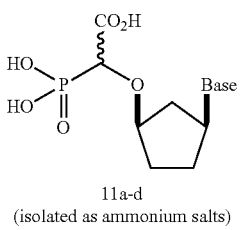

11a-d
(isolated as ammonium salts)

a thymin, b uracil, c cytosine, d adenine

The partially hydrolysed derivatives 28a-d, with the carboxylic ester intact, can also be purified by charcoal column chromatography, eluting with 10:10:3 ethanol/water/ammonia hydroxide (Scheme 5).

Scheme 5

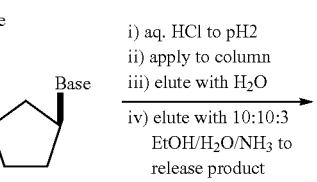

28a-d
(as sodium salts)

i) aq. HCl to pH2
ii) apply to column
iii) elute with $H_2O$
iv) elute with 10:10:3 EtOH/$H_2O$/$NH_3$ to release product

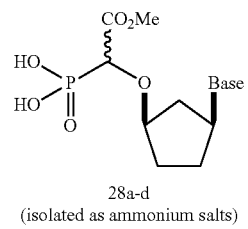

28a-d
(isolated as ammonium salts)

a thymine, b uracil, c cytosine, d adenine

Mono- and Diphosphorylations

As the phosphononucleosides 11a-d were envisaged as potential diphosphate or triphosphate mimics with the carboxylic acid mimicking one phosphate group, the monophosphorylated phosphononucleosides were important synthetic targets, with both the free carboxylic acid 12a-d and the methyl ester at the α-position 13a-d. 14a-d and 15a-d and prodrugs thereof are also part of the patent.

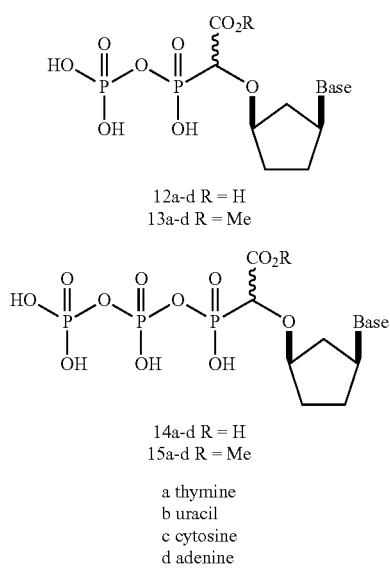

12a-d R = H
13a-d R = Me 14a-d R = H
15a-d R = Me a thymine
b uracil
c cytosine
d adenine The tributylammonium salt 29, generated in situ from 28a, was treated with an excess of 1,1-carbonyldiimidazole (CDI). Any unreacted CDI was quenched with methanol and the activated 5′-phosphoroimidazolidate 30 was reacted with an excess of tributylammonium phosphate (Scheme 6). The reaction mixture was stirred overnight before quenching with water. The solution was then directly applied to an ion exchange column of DEAE A-25 and eluted with ammonium bicarbonate (50 to 100 mM) and the fractions containing the pure product 13a were concentrated in vacuo to yield the compound as a white solid (52%).

Any attempts to hydrolyse the ester moieties of 13a using aqueous NaOH prior to ion exchange chromatography, as described by Debarge et al.,[42] resulted in 11a as the sole recovered material following ion exchange chromatography. Thus, the deprotection of the methyl ester was attempted on an ion-exchange-purified sample of 13a. In this instance the fully deprotected species 12a was accessed following hydrolysis of 13a with aqueous NaOH, as evidenced by the characteristic $^{31}$P NMR signals and HRMS on the isolated material.

Synthesis of the Enantioenriched Series of Phosphononucleosides

With the racemic phosphononucleosides 11a-d successfully isolated in excellent purity, the synthesis of these derivatives in enantiopure form ("natural" and "unnatural" enantiomers) was next undertaken. Access to these enantiopure compounds was achieved using enzymatic desymmetrisation of the prochiral diacetate 31, which would generate the two complimentary enantiomeric series of the key starting material cis-4-hydroxy-2-cyclopentylacetate 16 (Scheme 7). Following an enyme screen, the applicant selected CAL-B and PLE as the enzymes of choice to gain access to the (+)- and (−)-enantiomers, respectively.

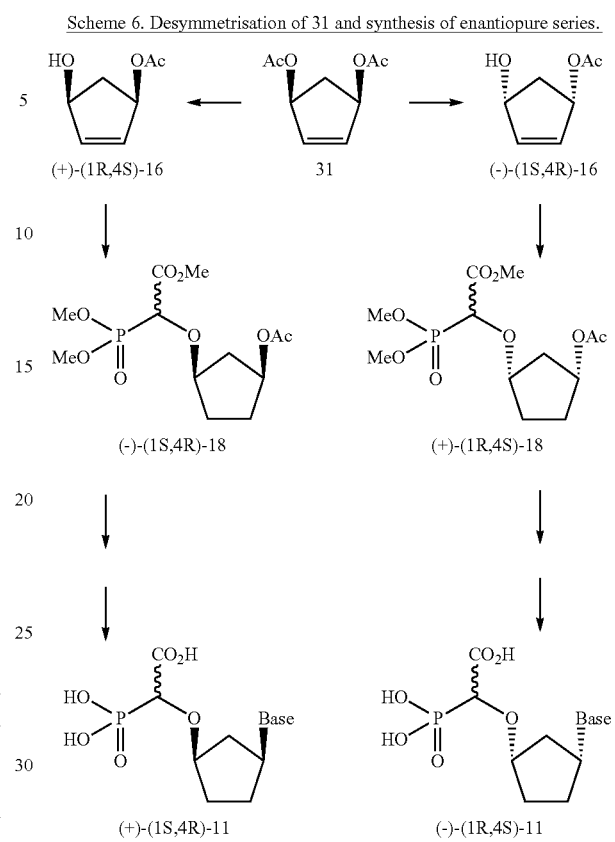

Scheme 6. Desymmetrisation of 31 and synthesis of enantiopure series.

Each of the series of enantioenriched phosphononucleosides (+)-11a-d and (−)-11a-d could then be accessed from the analogous precursor (+)-(1R,4S)-16 or (−)-(1S,4R)-16, employing the optimised route described for the racemic series, via the corresponding enantiomer of the trimethyl allylic acetate 20. Each of the phosphononucleosides (+)-11a-d were isolated in excellent enantiopurity (98% ee). The phosphononucleosides (+)-11a-d and (−)-11a-d were isolated in similar yields in each synthetic step to those described for the corresponding racemic derivatives 11a-d. Wherever possible, specific rotations were recorded at each step and development of HPLC conditions on a chiral stationary phase was undertaken for the unsaturated and saturated phosphononucleosides 24a-d and 26a-d and also for the final phosphonic acid derivatives 11a-d. The enantiomers of the alkene and alkane intermediates 24b and 26b were easily separated by using a Chiralcel® OJ-H column, with all four peaks clearly resolved. Separation of the enantiomers of the saturated thymine derivative 26a was successful to a degree using a Chiralpak® AS-H column, although complete resolution of all four peaks was not achieved. Tracking of the enantiopurities of a number of intermediates in the synthesis of the enantioenriched thymine and uracil derivatives 11a and 11b, by chiral HPLC and specific rotation, clearly show that the enantiopurity of the saturated derivatives 26a and 26b are the same as that of the starting acetoxy alcohol 16 in each case, thereby confirming that the stereochemical integrity of the precursor 16 is retained throughout the synthetic sequence.

The present invention is further described by way of the following non-limiting examples.

EXAMPLES

Experimental

(+)-(1R,4S)-4-Hydroxycyclopent-2-en-1-yl acetate (+)-(1R,4S)-16 cis-3,5-Diacetoxycyclopentene 31 (624 mg, 3.39 mmol), phosphate buffer (15 mL, 0.1M, pH7) and immobilised Candida antartica lipase B (62 mg, 10% wt/wt) were placed in a 100 mL conical flask and shaken until the reaction was judged complete by TLC analysis (diethyl ether) after 3.5 h. The reaction mixture was filtered to remove the enzyme and the resulting aqueous solution was washed with diethyl ether (3×25 mL). The ethereal layers were combined, dried over magnesium sulfate and concentrated in vacuo. The crude product was purified by flash chromatography ($SiO_2$, diethyl ether) to afford the pure compound (+)-(1R,4S)-16 (415 mg, 85% yield, 98% e.e.); m.p. 49-52° C.; $[\alpha]_D^{20}$ +65.54 (c 1.0, dichloromethane), Lit.[58] $[\alpha]_D^{20}$ +66.0 (c 1.0, chloroform); $\delta_H$ (400 MHz, $CDCl_3$): 1.63 (1H, dt, J=6.8, 4.4), 2.06 (3H, s), 1.82 (1H, br s), 2.77 (1H, dt, J=11.1, 7.2), 4.70-4.77 (1H, m), 5.48-5.51 (1H, m), 5.97-6.01 (1H, m), 6.10-6.14 (1H, m). HPLC conditions: CHIRALCEL® OJ-H, hexane/i-PrOH=95:5, 1 mL/min, 4-7° C., λ=210 nm, (+)-(1R,4S)-16 19.4 min, (−)-(1S,4R)-16 20.8 min. Note that the CAL B does not appear to be pH sensitive.

(−)-(1S,4R)-4-Hydroxycyclopent-2-en-1-yl acetate (−)-(1S,4R)-16 cis-3,5-Diacetoxycyclopentene 31 (1.185 mg, 6.43 mmol), phosphate buffer (30 mL, 0.1M, pH7) and pig liver esterase (120 mg, 10% wt/wt) were placed in a 100 mL rbf flask and the flask was shaken. The pH was kept constant by the continual addition of aqueous sodium hydroxide (1M) and the reaction mixture was judged complete by TLC analysis (diethyl ether) after 19 h. The reaction mixture was filtered to remove the enzyme and the resulting aqueous solution was washed with diethyl ether (3×60 mL). The ethereal layers were combined, dried over magnesium sulphate and concentrated in vacuo. The crude product was purified by flash chromatography ($SiO_2$, diethyl ether) to afford the pure compound (−)-(1S,4R)-16 (688 mg, 75% yield); m.p. 49-51° C.; $[\alpha]_D^{20}$-50.27 (c 0.56, dichloromethane), Lit.[58] $[\alpha]_D^{20}$ −69 (c 1.0, chloroform); $\delta_H$ (400 MHz, $CDCl_3$): 1.65 (1H, dt, J=14.7, 3.9), 2.06 (3H, s), 2.77 (1H, dt, J=14.4, 3.9), 4.69-4.76 (1H, m), 5.46-5.53 (1H, m), 5.95-6.01 (1H, m), 6.08-6.14 (1H, m). HPLC conditions: CHIRALCEL® OJ-H, hexane/i-PrOH=95:5, 1 mL/min, 4-7° C., λ=210 nm, (+)-(1R,4S)-16 19.4 min, (−)-(1S,4R)-16 20.8 min. Note the PLE is pH sensitive; when this reaction was carried out without keeping the pH at 7 the conversion was significantly lower (~40%).

O—H Insertion Reactions cis-1-[(Ethoxycarbonyl)diethylphosphonomethoxy]-4-acetoxycyclopent-2-ene 19

A solution of acetoxy alcohol 16 (259 mg, 1.82 mmol) and triethyl diazophosphonoacetate 17 (500 mg, 2.0 mmol) in benzene (20 mL) was added to a flame dried 50 mL round bottomed flask containing preactivated 3 Å molecular sieve powder (336 mg). The solution was degassed prior to the addition of copper(II) trifluoromethanesulfonate (28 mg, 0.08 mmol, 4 mol %), and heated in a pre-equilibrated oil bath (92° C.) under a nitrogen atmosphere for 19 h. The mixture was then allowed to cool to room temperature before filtering by gravity to remove the molecular sieve powder. The solution was then concentrated in vacuo. $^1H$ NMR analysis of the crude material indicated that the major component was the desired insertion product 19 (~85%, dr 1:1) and the reduced compound (~10%) was also observed. Purification by flash chromatography ($SiO_2$, diethyl ether) afforded 19 as a colourless oil (459 mg, 69% yield*, dr 1.2:1); $U_{max}$/cm$^{-1}$ (film) 3459, 2986 (CH), 2939 (CH), 1737 (C=O), 1645 (C=C), 1442, 1371, 1248 (P=O), 1113 (C—N), 1024 (C—O); $\delta_H$ (300 MHz, $CDCl_3$): 1.10-1.42 (9H, m) 1.71-1.80 (0.4H, dt, J=14.4, 4.2) 1.82-1.91 (0.6H, dt, J=15.0, 3.6), 2.04 (1.2H, s), 2.05 (1.8H, s), 2.77 (1H, overlapping dt, J=15.0, 7.2), 4.16-4.35 (6H, m), 4.42 (0.4H, d, $J_{PH}$=19.2), 4.45 (0.6H, d, $J_{PH}$=18.0), 4.60-4.65 (0.4H, m), 4.69-4.74 (0.6H, m), 5.45-5.50 (1H, m), 6.03-6.08 1H, m), 6.10-6.15 (1H, m); $\delta_C$ (150.9 MHz, $CDCl_3$): 14.1, 16.39, 16.43, 21.06, 21.09, 36.8, 36.9, 61.88, 61.93, 63.7, 63.8, 73.9 (d, $J_{PC}$=158.6), 74.4 (d, $J_{PC}$=158.9), 76.3, 76.4, 83.90 (d, $J_{PC}$=11.6), 83.91 (d, $J_{PC}$=12.4), 134.1, 134.7, 134.9, 135.5, 167.8 (br d, $J_{PC}$~2.0), 167.9 (br d, $J_{PC}$~2.3), 170.68, 170.70; $\delta_P$ (121.5 MHz, $CDCl_3$): 14.2, 16.5; HRMS (ES+): Exact mass calculated for $C_{15}H_{26}O_8P$ [M+H]$^+$ 365.1365. Found: 365.1372. m/z (ES+) 751.0 [(dimer+Na)$^+$, 40%], 729.0 (dimer, 30%). 574.2 (20%), 387.1 [(M+Na)$^+$, 90%], 365.1 [(M+H)$^+$, 100%], 305.1 (95%), 125.2 (100%).

*~95% pure by $^1H$ NMR analysis, ~2% of reduced product observed at 2.98 ppm (d, $J_{PC}$=21.6) and an unknown impurity seen at 4.56 (br s) in the $^1H$ NMR spectrum.

cis-1-[(Methoxycarbonyl)dimethylphosphonomethoxy]-4-acetoxycyclopent-2-ene 20

Compound 20 was prepared following the procedure described above for 19 except rhodium(II) acetate was used as the catalyst. Rhodium(II) acetate (8 mg, 0.018 mmol, 1 mol %) was added to a degassed solution of acetoxy alcohol 16 (2.309 g, 16.24 mmol) and trimethyl diazophosphonoacetate 18 (3.712 g, 17.85 mmol) in benzene (35 mL). The reaction mixture was stirred while heating under reflux for 5 h under a nitrogen atmosphere. $^1H$ NMR analysis of the crude oil indicated that the major component was the desired insertion product 20 (~85%, dr 1:1) however, the side product due to insertion into acetic acid (~13%) and traces of the reduced side product (~2%) were also observed. Purification by flash chromatography ($SiO_2$, 5% methanol in dichloromethane) yielded 20 as a pale yellow oil (3.873 g, 78% yield*, dr 1:1); $v_{max}$/cm$^{-1}$ (film) 2960 (CH), 1733 (C=O), 1438, 1373, 1244 (P=O), 1111, 1031 (C—O); $\delta_H$ (300 MHz, $CDCl_3$): 1.75 (0.5H, dt, J=14.7, 3.9), 1.86 (0.5H, dt, J=15.0, 3.9), 2.05 (0.5H, s), 2.06 (0.5H, s), 2.71-2.84 (1H, m), 3.81-3.89 (6H, m), 3.87-3.91 (3H, m), 4.49 (0.5H, d, $J_{PH}$=20.4), 4.52 (0.5H, d, $J_{PH}$=19.8), 4.60-4.67 (0.5H, m), 4.69-4.76 (0.5H, m), 5.45-5.52 (1H, m), 6.04-6.16 (2H, m); $\delta_C$ (75.5 MHz, $CDCl_3$): 21.05, 21.07, 36.7, 36.8, 52.9, 54.2-54.4 (m), 73.3 (d, $J_{PC}$=159.5), 73.9 (d, $J_{PC}$=159.8), 76.2, 76.3, 84.00 (br d, $J_{PC}$~11.3), 84.04 (br d, $J_{PC}$~12.0), 134.37, 134.42, 135.18, 135.23, 168.1 (d, $J_{PC}$~2.6), 168.2 (d, $J_{PC}$~2.8), 170.6 170.7; $\delta_P$ (121.5 MHz, $CDCl_3$): 16.5, 16.8; HRMS (ES+): Exact mass calculated for $C_{12}H_{20}O_8P$ [M+H]$^+$ 323.0896. Found: 323.0909. m/z (ES−) 90.9 [100%], 124.9 [80%], 151.0 [85%], 345.0 [(M+Na), 30%] 447.1 [30%].

*~98% pure by $^1H$ NMR analysis, ~2% of the reduced product seen at 3.00 ppm (d, $J_{PC}$=21.6) in the $^1H$ NMR spectrum.

(−)-(1S,4R)-1-[(Methoxycarbonyl)dimethylphosphonomethoxy]-4-acetoxycyclopent-2-ene(−)-(1S,4R)-20

This was synthesised using the procedure described above for 19 using acetoxy alcohol (+)-(1R,4S)-16 (1.491 g, 10.49 mmol) and trimethyl diazophosphonoacetate 18 (2.209 g, 10.62 mmol) in benzene (35 mL) and a spatula tip of rhodium(II) acetate. The reaction was stirred while heating under reflux for 17 h. $^1$H NMR analysis of the crude oil indicated the main product was the desired insertion product (−)-(1S,4R)-19 (~90%, 98% e.e., dr 1:1). Purification by flash chromatography (SiO$_2$, 5% methanol in dichloromethane) afforded (−)-(1S,4R)-19 as a pale yellow oil (2.820 g, 88% yield*, 98% e.e.**, dr 1:1); $[\alpha]_D^{20}$ −10.58 (c 0.95, dichloromethane)

*Estimated by $^1$H NMR analysis to be of ~97% purity, ~3% acetoxy alcohol (+)-(1R,4S)-16 present in the $^1$H NMR spectrum.

**The enantiopurity of (−)-(1S,4R)-20 was not determined directly, but assigned on the basis of the enantiopurites of the acetoxy alcohol (+)-(1R,4S)-16 and of the base insertion product (+)-(1R,4S)-24b.

(+)-(1R,4S)-1-[(Methoxycarbonyl)dimethylphosphonomethoxy]-4-acetoxycyclopent-2-ene (+)-(1R,4S)-20

This was synthesised using the procedure described above for 19 from the acetoxy alcohol (−)-(1S,4R)-16 (262 mg, 1.84 mmol, 30% e.e.) and trimethyl diazophosphonate 18 (415 mg, 2.00 mmol) and rhodium(II) acetate (8 mg, 0.02 mmol, 1 mol %) in benzene (20 mL). The reaction mixture was stirred while heating under reflux for 6 h. $^1$H NMR analysis of the crude oil indicated that the major component was the desired insertion product (+)-(1R,4S)-20 (~90%, dr 1:1). Following purification by flash chromatography (SiO$_2$, 5% methanol in dichloromethane) the product (+)-(1R,4S)-20 was isolated as a clear oil (545 mg, 92% yield, 30% e.e*., dr 1:1); $[\alpha]_D^{20}$ +3.50 (c 0.3, dichloromethane).

*The enantiopurity of (+)-(1R,4S)-20 was not determined directly but assigned on the basis of the enantiopurity of the acetoxy alcohol (−)-(1S,4R)-16 and of the base insertion product (−)-(1S,4R)-24b.

Base Insertion Reactions cis-1-{4-[(ethoxycarbonyl)diethylphosphonomethoxy]cyclopent-2-en-1-yl}thymine 23a A suspension of thymine (212 mg, 1.7 mmol) and aqueous sodium carbonate (2M, 0.7 mL, ~1.4 mmol) in acetonitrile (10 mL) was stirred for 10 min under a nitrogen atmosphere prior to the addition of the allylic acetate 19 (dr 1.2:1) (415 mg, 1.14 mmol) in acetonitrile (10 mL). Nitrogen was bubbled through the reaction mixture for 5 min and tetrakis (triphenylphosphine)palladium(0) (66 mg, 0.06 mmol, 5 mol %) was then added. The reaction mixture was stirred at 66° C. for 4.5 h prior to the addition of another 5 mol % of tetrakis(triphenylphosphine)palladium(0) (66 mg). The reaction mixture was stirred for a further 15 h at 66° C. and was then left to cool to room temperature before dichloromethane (20 mL) was added. The resulting precipitate was removed via gravity filtration and the solution was concentrated in vacuo. The major components of the $^1$H NMR spectrum of the crude product were the desired product 23a (~30%, dr 1.2:1), the α-hydroxyphosphonate 21 (~60%, 4.57 ppm, d, $J_{PC}$=10.8) and triphenylphosphine oxide (~10%). Purification by flash chromatography (SiO$_2$, 5% methanol in dichloromethane) yielded the product 23a as a cream solid (172 mg, 35%, dr 1.3:1); m.p. 135-137° C.; (Found: C, 50.00; H, 6.34; N, 6.56. C$_{18}$H$_{27}$N$_2$O$_8$P requires C, 50.23; H, 6.32; N, 6.56%); $v_{max}$/cm$^{-1}$ (KBr) 3165 (NH), 3043, 2994 (CH), 1742 (C=O), 1690 (C=O), 1667 (C=O), 1641 (C=C), 1470 (CH), 1263 (P=O), 1102 (C—N), 1022 (C—O); $\delta_H$ (300 MHz, CDCl$_3$) 1.27-1.40 (9H, m), 1.74-1.85 (1H, m), 1.94 (3H, s with unresolved splitting), 2.72-2.87 (1H, m), 4.14-4.38 (6H, m), 4.45 (0.6H, d, $J_{PH}$=19.5), 4.48 (0.4H, d, $J_{PH}$=18.9), 4.57-4.64 (0.6H, m), 4.64-4.71 (0.4H, m), 5.64-5.73 (1H, m), 5.91-5.98 (1H, m), 6.24-6.36 (1H, m), 7.30 (0.4H, br q, J~1.2, 7.36 (0.6H, br q J~1.2), 9.21 (1H, br s); $\delta_C$ (75.5 MHz, CDCl$_3$): 12.3, 14.10, 14.12, 16.35, 16.43, 37.0, 37.1, 57.7, 57.8, 62.1, 63.5 (d, $J_{PC}$=6.3), 63.9 (d, $J_{PC}$=6.6), 75.3 (d, $J_{PC}$=158.5), 84.6 (d, $J_{PC}$=10.5), 84.7 (d, $J_{PC}$=11.9), 111.5, 111.6, 134.6, 134.7, 135.5, 136.0, 137.2, 137.4, 151.2, 164.1, 167.2 (d, $J_{PC}$=2.1), 167.5 (d, $J_{PC}$=2.0); $\delta_P$ (121.5 MHz, CDCl$_3$): 13.9, 14.1; HRMS (ES+) Exact mass calculated for C$_{18}$H$_{28}$N$_2$O$_8$P [M+H]$^+$ 431.1583. Found: 431.1593. m/z (ES+) [M+H]$^+$ 861.0 (dimer 20%), 453.0 [(M+Na)$^+$, 30%)] 431.1 [(M+H)$^+$, 100%)], 350.1 (50%), 191.2 (70%), 110.1 (50%).

cis-1-{[4-(Methoxycarbonyl)dimethylphosphonomethoxy]cyclopent-2-en-1-yl}thymine 24a A degassed solution of aqueous sodium carbonate (2M, 0.35 mL, ~0.7 mmol) was added to a suspension of thymine (112 mg, 0.89 mmol) in acetonitrile (10 mL). The reaction mixture, which contained some undissolved material, was stirred for 15 min under a nitrogen atmosphere prior to the addition of a solution of the allylic acetate 20 (dr 1.1:1) (186 mg, 0.58 mmol) in acetonitrile (5 mL). The reaction mixture was degassed and tetrakis(triphenylphosphine)palladium(0) (54 mg, 0.047 mmol, 8 mol %) was added. The reaction mixture was stirred at 66° C. for 24 h and allowed to cool to room temperature before the addition of dichloromethane (20 mL). The mixture was filtered by gravity to remove the resulting precipitate and the solution was concentrated in vacuo. $^1$H NMR analysis indicated that the major components of the crude material were the desired compound 4a (~35%, dr 1.1:1), the α-hydroxyphosphonate 21 (~55%) and triphenylphosphine oxide (~10%). Purification via flash chromatography (SiO$_2$, 5% methanol in dichloromethane) yielded the product 24a as a cream solid (115 mg, 51%, dr 1.2:1); m.p. 134-138° C.; (Found: C, 46.27; H, 5.45; N, 6.86. C$_{15}$H$_{21}$N$_2$O$_8$P requires C, 46.40; H, 5.38; N, 7.21%); $v_{max}$/cm$^{-1}$ (KBr) 3176 (NH), 3042, 2959 (CH), 1754 (C=O), 1689 (C=O), 1663 (C=O), 1640 (C=C), 1470 (CH), 1264 (P=O), 1102 (C—N), 1029 (C—O); $\delta_H$ (300 MHz, CDCl$_3$): 1.73-1.85 (1H, m), 1.94 (3H, d, J=1.2), 2.73-2.87 (1H, m), 3.81-3.90 (9H, m), 4.50 (0.55H, d, $J_{PH}$=19.8), 4.53 (0.45H, d, $J_{PH}$=19.2), 4.58-4.64 (0.55H, m), 4.64-4.71 (0.45H, m), 5.62-5.73 (1H, m), 5.91-6.00 (1H, m), 6.25-6.35 (1H, m), 7.27 (0.45H, br q, J~1.2), 7.32 (0.55H, br q, J~1.2), 9.13 (1H, br s); $\delta_C$ (75.5 MHz, CDCl$_3$): 12.3, 36.9, 37.1, 53.0, 53.9-54.3 (m), 57.8, 57.9, 74.86 (d, $J_{PC}$=159.6), 74.93 (d, $J_{PC}$=159.5), 84.7 (d, $J_{PC}$=10.0), 84.8 (d, $J_{PC}$=11.6), 111.5, 111.6, 134.7, 134.9, 135.4, 135.9, 137.1, 137.2, 151.1, 163.9, 167.6 (br d, $J_{PC}$~2.5), 167.9 (br d, $J_{PC}$~2.3); $\delta_P$ (CDCl$_3$): 16.3, 16.5; HRMS (ES+) Exact mass calculated for C$_{15}$H$_{22}$N$_2$O$_8$P [M+H]$^+$ 389.1114. Found: 389.1086. m/z (ES+) [M+H]$^+$ 777.2 (30%), 406.1 (20%) 389.0 (100%), 82.9 (28%).

(+)-(1R,4S)-1-{4-[(Methoxycarbonyl)dimethylphosphonomethoxy]cyclopent-2-en-1-yl}thymine (+)-(1R,4S)-24a Thymine (714 mg, 5.66 mmol) was added to a degassed solution of the allylic acetate(−)-(1S,4R)-20 (98% e.e., dr 1:1) (1.251 g, 3.88 mmol) in acetonitrile (50 mL), followed by aqueous sodium carbonate (2M, 2.25 mL, ~4.50 mmol). Nitrogen was bubbled through the reaction mixture for 2 min prior to the addition of bis(dibenzylideneacetone)palladium(0) (112 mg, 0.21 mmol, 6 mol %) and 1,4-bis(diphenylphosphino)butane (182 mg, 0.427 mmol, 11 mol %). The reaction mixture, which contained some undissolved material, was stirred for 5.5 h at 50° C. under a nitrogen atmosphere. The reaction mixture was allowed to cool to room temperature and dichloromethane was added (60 mL). The resulting precipitate was removed via filtration by gravity and the solution was concentrated in vacuo. $^1$H NMR analysis indicated that the major components of the crude material were the desired product (+)-(1R,4S)-24a (~55%, dr 1:1), the α-hydroxyphosphonate 275 (~15%), the starting allylic acetate 20 (~10%) and dibenzylideneacetone (~20%). Purification by flash chromatography (SiO$_2$, 5% methanol in dichloromethane) yielded (+)-(1R,4S)-24a as a cream solid (831 mg, 55%, 98% e.e., dr 1:1.2); m.p. 134-135° C.; $[\alpha]_D^{20}$ +43.70 (c 1.00, dichloromethane. The enantiopurity of (+)-(1R,4S)-24a was not determined directly, but assigned on the basis of the enantiopurites of the acetoxy alcohol (+)-(1R,4S)-16 and of the saturated product (−)-(1S,4R)-26a.

(−)-(1S,4R)-1-{4-[(Methoxycarbonyl)dimethylphosphonomethoxy]cyclopent-2-en-1-yl}thymine (−)-(1S,4R)-24a Thymine (234 mg, 1.85 mmol) was added to a degassed solution of allylic acetate(+)-(1R,4S)-20 (70% e.e., dr 1:1) (395 mg, 1.23 mmol) in acetonitrile (20 mL), followed by aqueous sodium carbonate (2M, 0.7 mL, ~1.40 mmol). Nitrogen was bubbled through the reaction mixture for 2 min prior to the addition of bis(dibenzylideneacetone)palladium(0) (54 mg, 0.10 mmol, 8 mol %) and 1,4-bis(diphenylphosphino)butane (60 mg, 0.141 mmol, 11 mol %). The reaction mixture, which contained some undissolved material, was stirred for 5.5 h at 50° C. under a nitrogen atmosphere. The reaction mixture was allowed to cool to room temperature and dichloromethane was added (60 mL). The resulting precipitate was removed via filtration by gravity and the solution was concentrated in vacuo. $^1$H NMR analysis indicated the crude material consisted of the desired product (−)-(1S,4R)-24a (~40%, dr 1:1), the α-hydroxyphosphonate 21 (~40%) and dibenzylideneacetone (~20%). Purification by flash chromatography (SiO$_2$, 5% methanol in dichloromethane) yielded the compound (−)-(1S,4R)-24a as a cream solid (261 mg, 55%, 70% e.e, dr 1.2:1); m.p. 136-137° C.; $[\alpha]_D^{20}$ −33.22 (c 0.90, dichloromethane). The enantiopurity of (−)-(1S,4R)-24a was not determined directly, but assigned on the basis of the enantiopurites of the acetoxy alcohol (−)-(1S,4R)-16 and of the saturated product (+)-(1R,4S)-26a.

cis-1-{4-[(Ethoxycarbonyl)diethylphosphonomethoxy]cyclopent-2-en-1-yl}uracil 23b Tris(dibenzylideneacetone)dipalladium(0). chloroform (89 mg, 0.086 mmol, 5 mol %) and 1,4-bis(diphenylphospino)butane (90 mg, 0.211 mmol, 11 mol %) were added to a degassed solution of allylic acetate 20 (dr 1.2:1) (700 mg, 1.92 mmol) in N,N-dimethylformamide (15 mL). The solution was stirred for 5 min at room temperature under a nitrogen atmosphere prior to the addition of uracil (340 mg, 3.02 mmol) and aqueous sodium carbonate (2M, 1 mL, ~2.00 mmol). Nitrogen was bubbled through the dark red mixture for 2 min and the mixture was then stirred at 55° C. for 20 h. The mixture was allowed to cool to room temperature and diluted with dichloromethane (30 mL). The resulting precipitate was removed by gravity filtration and the solution was concentrated in vacuo. $^1$H NMR analysis of the crude residue indicated the major components were the desired product 23b (~30%, dr 1.2:1), the starting allylic acetate 19 (~55%) and dibenzylideneacetone (~15%). The crude material was purified by flash chromatography (SiO$_2$, 5% methanol in dichloromethane) to afford the product 23b as a pale yellow hygroscopic solid (242 mg, 29%, dr 1.2:1); m.p. 107-110° C.; (Found: C, 48.80; H, 6.01; N; 6.66. C$_{17}$H$_{25}$N$_2$O$_8$P requires C, 49.04; H, 6.05; N, 6.73%); $v_{max}$/cm$^{-1}$ (KBr) 3172 (NH), 3055 (CH), 2985 (CH), 1743 (C=O), 1681, 1462 (CH), 1262 (P=O), 1096 (C—N), 1021 (C—O); $\delta_H$ (300 MHz, CDCl$_3$): 1.28-1.39 (9H, m), 1.78 (0.45H, apparent dt, J~4.8, 3.0), 1.83 (0.55H, apparent dt, J~5.1, 3.0), 2.80 (1H, apparent dt, J~15.0, 7.8), 4.12-4.37 (6H, m), 4.46 (0.55H, d, $J_{PH}$=19.5), 4.48 (0.45H, d, $J_{PH}$=18.9), 4.59-4.65 (0.55H, m), 4.65-4.72 (0.45H, m), 5.64-5.74 (1H, m), 5.74 (1H, br d, J~8.7), 5.91-5.99 (1H, m), 6.27-6.32 (0.55H, m), 6.32-6.37 (0.45H, m), 7.52 (0.45H, d, J=8.1), 7.55 (0.55H, d, J=8.4), 9.72 (1H, br s); $\delta_C$ (75.5 MHz, CDCl$_3$): 14.1, 16.37, 16.44, 37.0, 37.3, 58.0, 58.1, 62.1, 63.5 (br d, $J_{PC}$~6.6), 63.6 (br d, $J_{PC}$~6.6), 63.8 (br d, $J_{PC}$~6.6), 63.9 (br d, $J_{PC}$~6.6), 75.3 (d, $J_{PC}$=158.6), 75.4 (d, $J_{PC}$=158.8), 84.4 (d, J=10.0), 84.6 (d, J=11.7, 102.9, 134.1, 134.4, 136.0, 136.4, 141.7, 151.2, 163.5, 163.6, 167.2 (br d, $J_{PC}$~2.1), 167.5 (br d, $J_{PC}$~2.1); $\delta_P$ (161.9 MHz, CDCl$_3$): 13.9, 14.1; HRMS (ES+): Exact mass calculated for C$_{17}$H$_{26}$N$_2$O$_8$P [M+H]$^+$ 417.1427. Found: 417.1415. m/z (ES+) 833.2 [dimer, 40%], 434.1 [(M+Na)$^+$, 15%], 417.1 [(M+H)$^+$, 100%]. A yield of 57% was achieved when this reaction was repeated at a later date with acetonitrile as solvent.

cis-1-{4-[(Methoxycarbonyl)dimethylphosphonomethoxy]cyclopent-2-en-1-yl}uracil 24b Aqueous sodium carbonate (2M, 0.6 mL, ~1.2 mmol) was added to a suspension of uracil (171 mg, 1.52 mmol) in acetonitrile (30 mL) and the mixture was stirred for 10 min under a nitrogen atmosphere prior to the addition of the allylic acetate 20 (dr 1:1) (324 mg, 1.01 mmol). Nitrogen was bubbled through the reaction mixture for 5 min and tetrakis(triphenylphosphine)palladium(0) (58 mg, mmol, 5 mol %) was then added. The reaction mixture was stirred at 66° C. for 24 h under a nitrogen atmosphere. The mixture was allowed to cool to room temperature prior to the addition of dichloromethane (40 mL). The resulting precipitate was removed via gravity filtration and the solution was concentrated in vacuo to give a dark red oil. The crude $^1$H NMR spectrum indicated that the major components were the desired product 24b (~35%, dr 1:1), the α-hydroxyphosphonate 21 (~55%) and triphenylphosphine oxide (~10%). Purification via flash chromatography (SiO$_2$, 5% methanol in dichloromethane) afforded the pure product 24b as a cream gum (148 mg, 38%, dr 1.2:1); $v_{max}$/cm$^{-1}$ (film) 3480, 3177 (NH), 3057 (CH), 2961 (CH), 1750 (C=O), 1689, 1625, 1462, 1380, 1260 (P=O), 1105 (C—N), 1032 (C—O); $\delta_H$ (300 MHz, CDCl$_3$): 1.74-1.86 (1H, 2× overlapping apparent dt, J=10.8, 2.7, 8.1, 3.0), 2.74-2.87 (1H, apparent dt, J=15.3, 7.5), 3.80-3.90 (9H, m), 4.50 (0.5H, d, $J_{PH}$=19.8), 4.53 (0.5H, d, $J_{PH}$=19.2), 4.59-4.65 (0.5H, m), 4.66-4.72 (0.5H, m), 5.64-5.72 (1H, m), 5.74 (1H, br d, J~8.1), 5.93-6.01 (1H, m), 6.28-6.37 (1H, m), 7.49 (0.5H, d, J=8.1), 7.51 (0.5H, d, J=8.1), 9.46 (1H, br s); $\delta_C$ (75.5 MHz, CDCl$_3$): 36.9, 37.3, 53.0, 54.1 (2× overlapping d, $J_{PC}$~6.6, 6.6), 54.2 (d, $J_{PC}$=6.3), 54.3 (d, $J_{PC}$=6.2), 58.08, 58.11, 74.78 (d, $J_{PC}$=159.8), 74.81 (d, $J_{PC}$=160.1), 84.5 (d, $J_{PC}$=9.6), 84.6 (d, $J_{PC}$=11.7), 102.9, 134.2, 134.6, 135.8, 136.4, 141.6, 151.1, 163.4, 167.5 (br d, $J_{PC}$~2.5), 167.8 (br d, $J_{PC}$~2.5); by (121.5 MHz, CDCl3): 16.3, 16.5; HRMS (ES+): Exact mass calculated for $C_{14}H_{20}N_2O_8P$ [M+H]$^+$ 375.0957. Found: 375.0952. m/z (ES+) 749.1 [dimer, 50%], 397.0 [(M+Na), 25%] 375.0 [(M+H)$^+$, 100%], 177.0 [30%], 82.9 [40%].

(+)-(1R,4S)-1-{4-[(Methoxycarbonyl)dimethyl-phosphonomethoxy]cyclopent-2-en-1-yl}uracil (+)-(1R,4S)-24b Uracil (208 mg, 1.86 mmol) was added to a degassed solution of allylic acetate(−)-(1S,4R)-20 (98% e.e., dr 1.1:1) (395 mg, 1.23 mmol) in acetonitrile (30 mL), followed by aqueous sodium carbonate (2M, 0.7 mL, ~1.40 mmol). Nitrogen was bubbled through the reaction mixture for 2 min prior to the addition of bis(dibenzylideneacetone)palladium(0) (38 mg, 0.07 mmol, 6 mol %) and 1,4-bis(diphenylphospino)butane (52 mg, 0.12 mmol, 10 mol %). The reaction mixture, which contained some undissolved material, was then stirred for 5.5 h at 50° C. under a nitrogen atmosphere before allowing it to cool to room temperature. Dichloromethane (30 mL) was added and the resulting precipitate was removed by filtration and the solution was concentrated in vacuo. $^1$H NMR analysis of the crude material indicated that the main components were the desired product (+)-(1R,4S)-24b (~60%, dr 1.1:1), the α-hydroxyphosphonate 21 (~30%) and dibenzylideneacetone (~10%). The crude material was purified by flash chromatography (SiO$_2$, 5% methanol in dichloromethane) to afford the product (+)-(1R,4S)-24b as a cream hygroscopic gum (294 mg, 64%, 98% e.e., dr 1.2:1); [α]$_D^{20}$ +19.56 (c 2.30, dichloromethane); HPLC conditions: CHIRALCEL® OJ-H column, 30:70 isopropanol:hexane, 0.7 mL/min. 49.2 min, 59.3 min, 83.6 min, 115.0 min.

(−)-(1S,4R)-1-{4-[(Methoxycarbonyl)dimethyl-phosphonomethoxy]cyclopent-2-en-1-yl}uracil (−)-(1S,4R)-24b Uracil (422 mg, 3.77 mmol) was added to a degassed solution of the allylic acetate(+)-(1R,4S)-20 (30% e.e., dr 1.1:1) (801 mg, 2.5 mmol) in acetonitrile (30 mL), followed by aqueous sodium carbonate (2M, 1.4 mL, ~2.80 mmol). Nitrogen was bubbled through the reaction mixture for 2 min prior to the addition of bis(dibenzylideneacetone)palladium(0) (94 mg, 0.18 mmol, 7 mol %) and 1,4-bis(diphenylphospino)butane (107 mg, 0.25 mmol, 10 mol %). The reaction mixture, which contained some insoluble material, was then stirred for 2.5 h at 55° C. under a nitrogen atmosphere. The mixture was then allowed to cool to room temperature and diluted with dichloromethane (30 mL). The mixture was filtered by gravity to remove the resulting precipitate and concentrated in vacuo. $^1$H NMR analysis of the crude material indicated that the main components were the desired product (−)-(1S,4R)-24b (~60%, dr 1.1:1), the α-hydroxyphosphonate 21 (~30%) and dibenzylideneac- etone (~10%). Purification by flash chromatography (SiO$_2$, 5% methanol in dichloromethane) afforded the product (−)-(1S,4R)-24b as a cream hygroscopic gum (511 mg, 55%, 30% e.e., dr 1:1); [α]$_D^{20}$ −5.87 (c 2.23, dichloromethane); HPLC conditions: CHIRALCEL® OJ-H column, 30:70 isopropanol:hexane, 0.7 mL/min. 49.2 min, 59.3 min, 83.6 min, 115.0 min.

cis-1-{4-[(Ethoxycarbonyl)diethylphospho-nomethoxy]cyclopent-2-en-1-yl}cytosine 23c A degassed solution of aqueous sodium carbonate (2M, 0.35 mL, ~0.70 mmol) was added to a stirring mixture of cytosine (103 mg, 0.93 mmol) and allylic acetate 19 (dr 1:1) (225 mg, 0.62 mmol) in N, N-dimethylformamide (15 mL). Nitrogen was bubbled through the reaction mixture for 2 min prior to the addition of bis(dibenzylideneacetone)palladium(0), chloroform (23 mg, 0.04 mmol, 7 mol %) and 1,4-bis(diphenylphospino)butane (27 mg, 0.06 mmol, 10 mol %). The reaction mixture was stirred for 28 h at 55° C. before concentration in vacuo. Dichloromethane (25 mL) was added to the residue, the resulting precipitate was removed via gravity filtration and the solution was concentrated in vacuo. $^1$H NMR analysis indicated that the major components of the crude material were the desired compound 23c (~50%, dr 1:1), the α-hydroxyphosphonate 21 (~35%) and dibenzylideneacetone (~15%). Purification by flash chromatography (SiO$_2$, 5% methanol in dichloromethane) afforded the pure phosphononucleoside 23c as a pale orange solid (101 mg, 39%, dr 1.1:1); m.p. 155-159° C.; (Found: C, 48.71; H, 6.27; $C_{17}H_{26}N_3O_7P$ requires C, 49.16; H, 6.31%); u$_{max}$/cm$^{-1}$ (KBr) 3381 (NH), 3101 (CH), 2986 (CH), 1735 (C=O), 1647, 1492, 1384, 1261 (P=O), 1105 (C—N), 1019 (C—O); $\delta_H$ (300 MHz, CDCl$_3$) 1.24-1.39 (9H, m), 1.67-1.79 (1H, 2× overlapping dt, J=8.4, 3.0, 8.4, 3.0), 2.76-2.89 (1H, dt, J=15.0, 7.5), 4.11-4.37 (6H, m), 4.42 (0.5H, d, $J_{PH}$=19.5), 4.44 (0.5H, d, $J_{PH}$=19.2), 4.55-4.62 (0.5H, m), 4.63-4.70 (0.5H, m), 4.99-7.00 (2H, br s), 5.74-5.85 (2H, m & d at 5.82, J=7.2), 5.92-6.00 (1H, m), 6.21-6.29 (1H, m), 7.51 (0.5H, d, J=7.5), 7.54 (0.5H, d, J=7.2); $\delta_C$ (75.5 MHz, CDCl$_3$) 14.13, 14.15, 16.4 (2 overlapping d, $J_{PC}$~5.8, 5.8), 37.6, 37.9, 58.78, 58.83, 62.1, 63.59, (d, $J_{PC}$~6.7), 63.64 (d, $J_{PC}$~6.7), 63.87 (CH$_3$, d, $J_{PC}$ 6.5), 63.91 (d, $J_{PC}$~6.5), 75.3 (d, $J_{PC}$=158.9), 84.86 (d, $J_{PC}$=10.2), 84.94 (d, $J_{PC}$=12.2), 95.0, 134.9, 135.2, 135.5, 135.6, 142.9, 143.0, 156.6, 165.4, 167.3 (d, $J_{PC}$=2.3), 167.6 (d, $J_{PC}$=2.1); $\delta_P$ (121.5 MHz, CDCl$_3$): 14.0, 14.3; HRMS (ES+) Exact mass calculated for $C_{17}H_{27}N_3O_7P$ [M+H]$^+$, 416.1587. Found 416.1532; m/z (ES+) [M+H]$^+$ 831.3 [dimer, 20%], 416.1 [(M+H)$^+$, 100%].

cis-1-{4-[(Methoxycarbonyl)dimethylphospho-nomethoxy]cyclopent-2-en-1-yl}cytosine 24c A degassed solution of aqueous sodium carbonate (2M, 0.45 mL, ~0.90 mmol) was added to a stirring mixture of cytosine (128 mg, 1.17 mmol) and allylic acetate 20 (dr 1:1.1) (255 mg, 0.79 mmol) in acetonitrile (10 mL) in a microwave tube. Nitrogen was bubbled through the reaction mixture for 2 min prior to the addition of bis(dibenzylideneacetone)-palladium(0) (25 mg, 0.05 mmol, 6 mol %) and 1,4-bis(diphenylphospino)butane (36 mg, 0.08 mmol, 10 mol %). The reaction mixture was degassed and the tube was sealed and placed in the microwave for 1 h at 55° C. with stirring. The mixture was then allowed to cool to room temperature and diluted with dichloromethane (10 mL). The mixture was filtered by gravity to remove the resulting precipitate and concentrated in vacuo. $^1$H NMR analysis of the crude residue indicated that the major components were the desired product 24c (~35%, dr 1:1.1), the α-hydroxyphosphonate 21 (~55%) and dibenzylideneacetone (~10%). Purification by flash chromatography (SiO$_2$, 5% methanol in dichloromethane) afforded the product 24c as a cream hygroscopic gum (105 mg, 36%, dr 1:1, A:B); $v_{max}$/cm$^{-1}$ (film) 3423 (NH), 3194 (CH), 2957 (CH), 2853 (CH), 1736 (C=O), 1723 (C=O), 1649, 1233 (P=O), 1101 (C—N), 1051 (C—O); $\delta_H$ (300 MHz, CDCl$_3$): 1.67-1.80 (1H, 2 overlapping dt, J=10.2, 2.7, 10.2, 3.0), 2.76-2.90 (1H, m), 3.79-3.99 (9H, m), 4.47 (0.5H, d, $J_{PH}$=19.8), 4.50 (0.5H, d, $J_{PH}$=19.5), 4.56-4.62 (0.5H, m), 4.65-4.71 (0.5H, m), 5.10-7.00 (2H, br s), 5.76-5.88 (2H, m & d at 5.83, J~7.2), 5.94-6.02 (1H, m), 6.23-6.30 (1H, m), 7.52 (0.5H, d, J=7.2), 7.54 (0.5H, d, J=7.2); $\delta_C$ (75.5 MHz, CDCl$_3$): 37.5, 37.8, 53.0, 54.1-54.4, 58.77, 58.83, 74.65 (d, $J_{PC}$=160.0), 74.72 (d, $J_{PC}$=159.8, PCH), 85.0 CH, d, J 9.7), 86.0 (br d, J~12.5), 95.2, 134.8, 135.2, 135.5, 135.8, 142.7, 156.3, 165.2, 167.7 (br d, $J_{PC}$~2.7), 167.9 (br d, $J_{PC}$~2.3); by (121.5 MHz, CDCl$_3$): 16.4, 16.8; HRMS (ES+): Exact mass calculated for C$_{14}$H$_{21}$N$_3$O$_7$P [(M+H)$^+$], 374.1117. Found 374.1114. m/z (ES+) 747.2 [dimer, 100%], 597.1 (10%), 459.1 (10%), 388.1 (15%), 374.1 [(M+H)$^+$, 50%]. This phosphononucleoside 24c decomposes readily in solvents such as dichloromethane, deuterated chloroform and methanol. Significant decomposition was seen in a sample of 24c in deuterated chloroform after 36 hours at room temperature.

(+)-(1R,4S)-1-{4-[(Methoxycarbonyl)dimethylphosphonomethoxy]cyclopent-2-en-1-yl}cytosine (+)-(1R,4S)-24c This was prepared following the procedure described for 23a from the allylic acetate(−)-(1S,4R)-20 (98% e.e., dr 1.1:1) (390 mg, 1.21 mmol), cytosine (202 mg, 1.82 mmol) and aqueous sodium carbonate (2M, 0.66 mL, ~1.32 mmol), bis(dibenzylideneacetone)-palladium(0) (35 mg, 0.07 mmol, 5 mol %) and 1,4-bis(diphenylphospino)butane (52 mg, 0.12 mmol, 10 mol %), in acetonitrile (25 ml) for 3 h at 55° C. $^1$H NMR analysis of the crude residue indicated that the main components were (+)-(1R,4S)-24c (~40%, dr 1.1:1), the starting allylic acetate(−)-(1S,4R)-20 (~25%, dr 1.1:1), the α-hydroxyphosphonate 21 (~25%) and dibenzylideneacetone (~10%). Purification by flash chromatography (SiO$_2$, 5% methanol in dichloromethane) afforded the pure product (+)-(1R,4S)-24c as a light brown gum (178 mg, 39% yield, 98% e.e., dr 1.1:1); $[\alpha]_D^{20}$ +24.50 (c 0.1, dichloromethane). The enantiopurity of (+)-(1R,4S)-24c was not determined directly, but assigned on the basis of the enantiopurity of the acetoxy alcohol (+)-(1R,4S)-16.

(−)-(1S,4R)-1-{4-[(Methoxycarbonyl)dimethylphosphonomethoxy]cyclopent-2-en-1-yl}cytosine (−)-(1S,4R)-24c Cytosine (441 mg, 3.97 mmol) was added to a degassed solution of allylic acetate(+)-(1R,4S)-20 (70% e.e., dr 1:1) (848 mg, 2.63 mmol) in acetonitrile (45 mL). A solution of aqueous sodium carbonate (2M, 1.5 mL~3.0 mmol) was added and nitrogen was bubbled through the reaction mixture for 2 min prior to the addition of bis(dibenzylideneacetone)-palladium(0) (104 mg, 0.2 mmol, 7.5 mol %) and 1,4-bis(diphenylphospino)butane (114 mg, 0.27 mmol, 10 mol %). The reaction mixture was then degassed and stirred for 6.5 h at 55° C. under a nitrogen atmosphere. The reaction mixture was allowed to cool to room temperature before diluting with dichloromethane (60 mL) and the mixture then was filtered by gravity to remove the resulting precipitate and concentrated in vacuo. $^1$H NMR analysis of the crude material indicated the main components were the desired product (−)-(1S,4R)-24c (~35%, dr 1:1), the starting allylic acetate(+)-(1R,4S)-20 (~30%), the α-hydroxyphosphonate 21 (~25%) and dibenzylideneacetone (~10%). Purification by flash chromatography (SiO$_2$, 5% methanol in dichloromethane) afforded (−)-(1S,4R)-24c as a pale brown gum (356 mg, 36%, 70% e.e., dr 1.2:1); $[\alpha]_D^{20}$ −18.25 (c 0.2, dichloromethane). The enantiopurity of (−)-(1S,4R)-24c was not determined directly, but assigned on the basis of the enantiopurity of the acetoxy alcohol (−)-(1S,4R)-16.

cis-9-{4-[(Ethoxycarbonyl)diethylphosphonomethoxy]cyclopent-2-en-1-yl}adenine 23d Tris(dibenzylideneacetone)dipalladium(0). chloroform (53 mg, 0.05 mmol, 5 mol %) and 1,4-bis(diphenylphospino)butane (41 mg, 0.10 mmol, 10 mol %) were added to a degassed solution of the allylic acetate 19 (dr 1:1) (345 mg, 0.95 mmol) in N,N-dimethylformamide (8 mL) and the reaction mixture was stirred for 5 min under a nitrogen atmosphere. Adenine (195 mg, 1.44 mmol) was added, followed by aqueous cesium carbonate (2M, 0.5 mL, ~1 mmol) and nitrogen was bubbled through the mixture for 2 min. The reaction mixture, which contained some undissolved material, was then stirred for 26 h at 50° C. before concentration in vacuo. Dichloromethane (20 mL) was added to the residue, the resulting precipitate was removed by gravity filtration and the solution was concentrated in vacuo. $^1$H NMR analysis indicated that the main components of the crude material were the desired compound N-9-23d (~55%, dr 1:1), N-7-23d (~5%), the α-hydroxyphosphonate 21 (~30%) and dibenzylideneacetone (~10%). Purification by flash chromatography (SiO$_2$, 5% methanol in dichloromethane) afforded the product N-9-23d as a cream hygroscopic solid (206 mg, 49%, dr 1:1.3); m.p. 142-144° C.; $v_{max}$/cm$^{-1}$ (KBr) 3394 (NH), 3334 (NH), 3174, 2984 (CH), 1749 (C=O), 1663, 1599 (C=C), 1573, 1478 (CH), 1262 (P=O), 1098 (C—N), 1019 (C—O); $\delta_H$ (300 MHz, CDCl$_3$): 1.26-1.40 (9H, m), 2.03-2.16 (1H, 2 overlapping dt, J=14.4, 2.7, 14.4, 2.7) 2.85-3.00 (1H, m), 4.11-4.39 (6H, m), 4.50 (0.4H, d, $J_{PH}$=19.8), 4.57 (0.6H, d, $J_{PH}$=19.2), 4.70-4.77 (0.4H, m), 4.78-4.85 (0.6H, m), 5.61-5.70 (1H, m), 6.11-6.20 (1H, m), 6.24 (2H, br s), 6.32-6.40 (1H, m), 8.12 (0.6H, s), 8.15 (0.4H, s), 8.35 (1H, s); $\delta_C$ (75.5 MHz, CDCl$_3$): 14.08, 14.13, 16.3-16.5 (m), 38.3, 38.7, 56.46, 56.50, 62.0, 62.1, 63.6 (2 overlapping d, $J_{PC}$~6.7, 6.5), 63.89 (br d, $J_{PC}$~6.6), 63.94 (br d, $J_{PC}$~6.6, 75.1 (d, $J_{PC}$=158.6), 75.3 (d, $J_{PC}$=158.7), 84.3 (d, $J_{PC}$=10.6), 84.6 (d, $J_{PC}$=11.9), 119.5, 134.4, 134.9, 135.0, 135.6, 139.65, 139.73, 149.6, 152.8, 155.7, 167.4 (d, $J_{PC}$=2.0), 167.6 (d, $J_{PC}$=2.1); $\delta_P$ (121.5 MHz, CDCl$_3$): 13.9, 14.2; HRMS (ES+): Exact mass calculated for C$_{18}$H$_{27}$N$_5$O$_6$P [M+H]$^+$ 440.1699. Found: 440.1695. m/z (ES+) 442.3 (5%) 441.3 [20%] 440.3 [(M+H)$^+$, 100%]. A yield of 60% was achieved when this reaction was repeated with acetonitrile as solvent.

cis-9-{4-[(Methoxycarbonyl)dimethylphosphonomethoxy]cyclopent-2-en-1-yl}adenine 24d Adenine (316 mg, 2.34 mmol) was added to a degassed solution of the allylic acetate 20 (dr 1:1) (458 mg, 1.42 mmol) in acetonitrile (25 mL), followed by aqueous cesium carbonate (2M, 0.7 mL, ~1.43 mmol). Nitrogen was bubbled through the reaction mixture for 2 min prior to the addition of tris(dibenzylideneacetone)palladium(0) chloroform (80 mg, 0.09 mmol, 6 mol %) and 1,4-bis(diphenylphospino)butane (67 mg, 0.16 mmol, 11 mol %). The reaction mixture, which contained some undissolved material, was then stirred for 5.5 h at 50° C. under a nitrogen atmosphere. The mixture was allowed to cool to room temperature, diluted with dichloromethane (30 mL), filtered by gravity to remove the resulting precipitate and concentrated in vacuo. $^1$H NMR analysis of the crude material showed a complex mixture of products, however, the peaks for the desired compound 24d (dr 1:1) were present. Purification by flash chromatography (SiO$_2$, 5% methanol in dichloromethane) yielded the phosphononucleoside 24d as a cream hygroscopic gum (153 mg, 27%, dr 1:1); $v_{max}$/cm$^{-1}$ (film) 3392 (NH), 3185, 2958 (CH), 1749 (C=O), 1655, 1599 (C=C), 1235 (P=O), 1104 (C—N), 1035 (C—O); $\delta_H$ (300 MHz, CDCl$_3$): 2.01-2.17 (1H, 2 dt, J=9.6, 3.0, 9.3, 3.0), 2.84-3.00 (1H, m), 3.78-3.92 (9H, m), 4.55 (0.5H, d, J$_{PH}$=20.1), 4.65 (0.5H, d, J$_{PH}$=19.5), 4.70-4.77 (0.5H, m), 4.79-4.86 (0.5H, m), 5.61-5.70 (1H, m), 6.10-6.31 (3H, m), 6.34-6.41 (1H, m), 8.10 (0.5H, s), 8.11 (0.5H, s), 8.35 (1H, s); $\delta_C$ (75.5 MHz, CDCl$_3$): 38.2, 38.6, 53.06, 53.08, 54.0-54.5 [4 overlapping d, J~6.7, 6.8, 6.7, 6.6), 56.5, 56.6, 74.5 (d, J$_{PC}$=159.6), 74.6 (d, J$_{PC}$=159.8), 84.5 (d, J$_{PC}$=10.5), 84.8 (d, J$_{PC}$=11.8), 119.46, 119.48, 134.5, 134.8, 135.2, 135.6, 139.59, 139.64, 149.52, 149.54, 152.9, 155.59, 155.61, 167.7 (d, J$_{PC}$=2.2), 167.9 [d, J$_{PC}$=2.5); $\delta_P$ (CDCl$_3$): 16.3, 16.6; HRMS (ES+) Exact mass calculated for C$_{15}$H$_{21}$N$_5$O$_6$P [M+H]$^+$ 398.1229. Found: 398.1215 m/z (ES+) [M+H]$^+$ 398.2 [(M+H)$^+$, 100%], 412.1 [10%].

(+)-(1R,4S)-9-{4-[(Methoxycarbonyl)dimethylphosphonomethoxy]cyclopent-2-ene-1-yl}adenine (+)-(1R,4S)-24d Adenine (521 mg, 3.86 mmol) was added to a degassed solution of allylic acetate(−)-(1S,4R)-20 (98% e.e., dr 1:1), (701 mg, 2.18 mmol) in acetonitrile (70 mL), followed by aqueous cesium carbonate (2M, 1.35 mL, ~2.7 mmol). Nitrogen was bubbled through the reaction mixture prior to the addition of bis(dibenzylideneacetone)palladium(0) (75 mg, 0.14 mmol, 7 mol %) and 1,4-bis(diphenylphospino)butane (123 mg, 0.29 mmol, 13 mol %). The reaction mixture, which contained some undissolved material, was then stirred for 5 h at 50° C. under a nitrogen atmosphere. The reaction mixture was allowed to cool to room temperature, diluted with dichloromethane (70 mL), filtered by gravity to remove the resulting precipitate and concentrated in vacuo. $^1$H NMR analysis of the crude material showed a mixture of compounds of which the desired compound (+)-(1R,4S)-24d (~30%, dr 1:1) and dibenzylideneacetone (~10%) were identifiable. Purification by flash chromatography (SiO$_2$, 5% methanol in dichloromethane) afforded the product (+)-(1R,4S)-24d as a cream hygroscopic gum (279 mg, 32%, 98% e.e. dr 1.1:1). The enantiopurity of (+)-(1R, 4S)-24d was not determined directly, but assigned on the basis of the enantiopurity of the starting acetoxy alcohol (+)-(1R,4S)-16.

(−)-(1S,4R)-9-{4-[(Methoxycarbonyl)diethylphosphonomethoxy]cyclopent-2-en-1-yl}adenine (−)-(1S,4R)-24d Adenine (352 mg, 2.56 mmol) was added to a degassed solution of allylic acetate(+)-(1R,4S)-20 (70% e.e., dr 1.1:1) (551 mg, 1.70 mmol) in acetonitrile (25 mL), followed by aqueous cesium carbonate (2M, 1.0 mL, ~2.0 mmol). Nitrogen was bubbled through the reaction mixture for 2 min prior to the addition of bis(dibenzylideneacetone)palladium (0) (62 mg, 0.12 mmol, 6 mol %) and 1,4-bis(diphenylphospino)butane (80 mg, 0.19 mmol, 11 mol %). The reaction mixture, which contained some undissolved material, was then stirred for 2.5 h at 55° C. under a nitrogen atmosphere. The reaction mixture was allowed to cool to room temperature and then diluted with dichloromethane (70 mL). The resulting precipitate was removed by gravity filtration and the solution was concentrated in vacuo. The crude $^1$H NMR spectrum indicated that the main components were the desired product (−)-(1S,4R)-24d (~35%, dr 1.1:1), the α-hydroxyphosphonate 21 (~35%), dibenzylideneacetone (~20%) and an unknown impurity (~10%, 5.33 ppm, t, J=2.1). Purification by flash chromatography (SiO$_2$, 5% methanol in dichloromethane) afforded the product (−)-(1S, 4R)-24d as a cream hygroscopic gum (268 mg, 40%, 70% e.e., dr 1.1:1). The enantiopurity of (−)-(1S,4R)-24d was not determined directly, but assigned on the basis of the enantiopurity of the starting acetoxy alcohol (−)-(1S,4R)-16.

cis-2-Amino-9-[{4-(methoxycarbonyl)dimethylphosphonomethoxy}cyclopent-2-en-1-yl]-6-chloropurine N-9-24e and cis-2-Amino-7-[{4-(methoxycarbonyl)dimethylphosphonomethoxy}cyclopent-2-en-1-yl]-6-chloropurine N-7-24e 2-Amino-6-chloropurine (432 mg, 2.55 mmol) was added to a degassed solution of allylic acetate 20 (dr 1.1:1) (550 mg, 1.70 mmol) in acetonitrile (25 mL), followed by aqueous cesium carbonate (2M, 0.95 mL, ~1.89 mmol). Nitrogen was bubbled through the reaction mixture for 2 min prior to the addition of bis(dibenzylideneacetone)palladium(0) (50 mg, 0.15 mmol, 5 mol %) and 1,4-bis(diphenylphosphino)butane (73 mg, 0.17 mmol, 10 mol %). The reaction mixture, which contained some undissolved material, was stirred for 6.5 h at 45° C. under a nitrogen atmosphere before allowing it to cool to room temperature and diluting with dichloromethane (30 mL). The mixture was filtered by gravity to remove the resulting precipitate and concentrated in vacuo. $^1$H NMR analysis of the crude material indicated that the main components were N-9-24e (~35%, dr 1.1:1), the N-7-24e (~35% dr 1.1:1), α-hydroxyphosphonate 21 (~15%) and dibenzylidene acetone (~15%). Purification by flash chromatography (SiO$_2$, 5% methanol in dichloromethane) afforded the N-9-24e (101 mg, 14%, dr 1.2:1) as a pale yellow oil, and N-7-24e (253 mg, 35%, dr 1.2:1) as a yellow oil;

N-9-24e $\delta_H$ (300 MHz, CDCl$_3$): 2.09 (0.45H, dt, J=15.0, 3.3), 2.32 (0.55H, dt, J=15.0, 4.5), 2.83-3.02 (1H, m), 3.79-3.89 (9H, m), 4.78 (0.45H, d, J$_{PC}$=20.4), 4.79-4.86 (0.45H, m), 4.99-5.06 (0.55H, m), 5.25-5.39 (2.1H, m), 5.41-5.48 (1H, m), 5.54 [1H, br s), 6.04-6.12 (1H, m), 6.22-6.28 (0.55H, m), 6.34-6.39 (0.45H, m), 7.88 (0.55H, br s), 7.97 (0.45H, br s).

N-7-24e (Found: C, 39.50; H, 4.47; N, 15.87 C$_{12}$H$_{17}$O$_6$P.1.2H$_2$O requires C, 39.74; H, 4.76; N, 15.45%); $v_{max}$/cm$^{-1}$ (KBr) 3440, 3401, 3327 (NH), 3209 (CH), 2958 (CH), 1749 (C=O), 1626, 1544, 1496 (CH), 1378, 1257, 1226 (P=O), 1107 (C—N), 1028 (C—O); $\delta_H$ (300 MHz, CDCl$_3$): 1.98-2.14 (1H, 2 dt, J=14.7, 2.7, 15.0, 3.0), 2.87-3.03 (1H, m), 3.72-3.90 (9H, m), 4.48 (0.55H, d, J$_{PC}$=19.8), 4.52 (0.45H, d, J$_{PC}$=19.2), 4.69-4.75 (0.55H, m), 4.77-4.83 (0.45H, m), 5.33 (2H, br s), 5.76-5.86 (1H, m), 6.21-6.29 (1H, m), 6.43-6.51 (1H, m), 8.19 (0.45H, br s), 8.20 (0.55H, br s); $\delta_C$ (75.5 MHz, CDCl$_3$): 39.4, 39.8, 53.08, 53.10, 54.1-54.5 (m), 59.7, 59.8, 74.89 (d, $J_{PC}$=159.6), 74.94 (d, $J_{PC}$=159.8), 84.5 (d, $J_{PC}$=10.7), 84.7 (d, $J_{PC}$=12.3), 132.7, 133.3, 134.0, 136.4, 137.1, 143.1, 146.9, 159.3, 164.4, 167.6 (d, J=2.2), 167.8 (d, J=2.5); $\delta_P$ (121.5 MHz, CDCl$_3$): 16.0, 16.2

Peaks due to unknown impurity (~10%) visible in $^{13}$C NMR spectrum at 141.8, 159.1 ppm and in the $^1$H NMR at 5.51-5.53 (0.2H, m) and 8.10 (0.2H, s).

Hydrogenation Reactions cis-1-{4-[(Ethoxycarbonyl)diethylphosphonomethoxy]cyclopentan-1-yl}thymine 25a Palladium (5% on carbon, 23 mg) was added to a hydrogenation vessel followed by a solution of the alkene 23a (dr 1.2:1) (53 mg, 0.12 mmol) in absolute ethanol (10 mL). The reaction mixture was shaken under hydrogen at 30 psi at room temperature for 3 h at which point the mixture was tested by $^1$H NMR and the reaction judged to be complete. The palladium catalyst was removed by filtration through a short column of Celite®, the column was washed with ethanol (2×10 mL) and the filtrate was concentrated in vacuo. $^1$H NMR analysis of the crude material showed the alkane 25a was the main component (~90%, dr 1.1:1). Purification by flash chromatography (SiO$_2$, 5% methanol in dichloromethane) yielded the saturated compound 25a as a cream solid (46 mg, 89%, dr 1.2:1); m.p. 133-135° C.; $v_{max}$/cm$^{-1}$ (KBr) 3174 (NH), 3054, 2991 (CH), 1742 (C=O), 1691 (C=O), 1667 (C=O), 1643 (C=C), 1470 (CH), 1257 (P=O), 1105 (C—N), 1022 (C—O); $\delta_H$ (600 MHz, CDCl$_3$): 1.29-1.40 (9H, m), 1.53-1.64 (1H, m), 1.78-1.88 (2H, m), 1.98 (1.35H, s), 1.99 (1.65H, s), 2.01-2.07 (0.55H, br dd, J~6.0, 7.2), 2.08-2.14 (0.45H, br dd, J~6.0, 7.2), 2.16-2.24 (1H, m), 2.33-2.42 (1H, m, 4.14-4.34 (7H, m), 4.35 (0.55H, d, $J_{PH}$=18.6), 4.40 (0.45H, d, $J_{PH}$=19.8), 5.22-5.31 (1H, m), 7.70 (0.45H, s), 7.86 (0.55H, s), 8.79 (1H, br s); $\delta_C$ (125.8 MHz, CDCl$_3$): 12.26, 12.28, 14.10, 14.12, 16.3-16.5 (m), 30.10, 30.14, 30.6, 31.4, 38.5, 38.7, 53.1, 53.2, 61.98, 62.05, 63.4 (d, $J_{PC}$=6.7), 63.6 (d, $J_{PC}$=6.5), 63.9 (d, $J_{PC}$=6.5), 73.9 (d, $J_{PH}$=159.6), 74.6 (d, $J_{PH}$=158.8), 81.8 (d, $J_{PH}$=11.6), 82.7 (d, $J_{PH}$=8.6), 111.67, 111.75, 138.1, 138.3, 151.3, 151.4, 163.76, 163.78, 167.3 (br d, $J_{PC}$~1.6), 167.5 (br d, $J_{PC}$~2.4), $\delta_P$ (CDCl$_3$): 14.1, 14.6; HRMS (ES+) Exact mass calculated for C$_{18}$H$_{30}$N$_2$O$_8$P [M+H]$^+$433.1740. Found: 433.1749. m/z (ES-F) [M+H]$^+$ 865.2 (dimer 5%), 721.1 (5%), 676.3 (10%), 505.0 (5%), 483.0 [(M+Na)$^+$, 15%)] 433.1 [(M+H)$^+$, 100%)], 352.2 (20%), 289.2 (40%). Peaks due to an unknown impurity were observed in the $^1$H NMR spectrum at 2.45 ppm (apparent t, $J_{PC}$=21.6). The impurity was also seen in the $^{13}$C NMR spectrum at 62.6 ppm (apparent t, $J_{PC}$=2.5) and in the $^{31}$P NMR at 19.4 ppm.

cis-1-{4-[(Methoxycarbonyl)dimethylphosphonomethoxy]cyclopentan-1-yl}thymine 26a This was prepared following the procedure described for 25a above from the alkene 24a (dr 1.2:1) (108 mg, 0.28 mmol) and 10% palladium on carbon (54 mg) in methanol (10 mL). The $^1$H NMR spectrum of the crude material indicated that the desired alkane 26a was the main component of (95%, dr 1:1). Purification by flash chromatography (SiO$_2$, 5% methanol in dichloromethane) yielded the saturated compound 26a as a cream solid (100 mg, 92%, dr 1.1:1); m.p. 130-133° C.; (Found: C, 45.91; H, 5.84; N, 6.90. C$_{15}$H$_{23}$N$_2$O$_8$P requires C, 46.16; H, 5.94; N, 7.18%); $v_{max}$/cm$^{-1}$ (KBr) 3183 (NH), 3053, 2960 (CH), 1748 (C=O), 1689 (C=O), 1662 (C=O), 1644 (C=C), 1469 (CH), 1261 (P=O), 1113 (C—N), 1023 (C—O); $\delta_H$ (600 MHz, CDCl$_3$): 1.55-1.66 (1H, m), 1.76-1.90 (2H, m), 1.98 (1.5H, s), 2.00 (1.5H, s), 2.02-2.07 (0.5H, br dd, J~6.6, 7.2), 2.08-2.14 (0.5H, br, dd, J~6.6, 7.2), 2.16-2.25 (1H, m), 2.35-2.43 (1H, m), 3.83-3.90 (9H, m), 4.15-4.19 (0.5H, m), 4.20-4.24 (0.5H, m), 4.40 (0.5H, d, $J_{PH}$=18.6), 4.46 (0.5H, d, $J_{PH}$=19.8), 5.22-5.31 (1H, m), 7.66 (0.5H, s), 7.80 (0.5H, s), 8.75 (1H, br s); $\delta_C$ (75.5 MHz, CDCl$_3$): 12.25, 12.27, 30.0, 30.1, 30.6, 31.4, 38.4, 38.7, 52.97, 53.00, 53.02, 53.2, 53.8-54.4 (m), 73.3 (d, $J_{PC}$=160.8), 74.1 (d, $J_{PC}$=160.1), 82.0 (d, $J_{PC}$=11.3), 82.8 (d, $J_{PC}$=9.1), 111.67, 111.8, 138.0, 138.1, 151.45, 151.48, 163.9, 167.7 (d, J=2.3), 167.9 (d, J=2.3); by (121.5 MHz, CDCl$_3$): 16.8, 17.0; HRMS (ES+): Exact mass calculated for C$_{15}$H$_{24}$N$_2$O$_8$P [M+H]$^+$, 391.1270. Found 390.1263. m/z (ES+) 803.2 (10%) 598 (10%), 464 (8%) 413 [(M+Na)$^+$, 100%], 391 [(M+H)$^+$, 40%].

(−)-(1S,4R)-1-{4-[(Methoxycarbonyl)dimethylphosphonomethoxy]cyclopentan-1-yl}thymine(−)-(1S,4R)-26a This was prepared following the procedure described for 25a above from the alkene (+)-(1R,4S)-24a (98% e.e., dr 1.2:1) (636 mg, 1.64 mmol) and 5% palladium on carbon (217 mg) in methanol (25 mL). The $^1$H NMR spectrum of the crude residue indicated that the main component was the desired alkane (−)-(1S,4R)-26a (95%, dr 1:1). Purification by flash chromatography (SiO$_2$, 5% methanol in dichloromethane) yielded the saturated compound (−)-(1S,4R)-26a as a white solid (584 mg, 91%, 98% e.e., dr 1.1:1); m.p. 133-135° C.; $[\alpha]_D^{20}$ −8.48 (c 0.67, dichloromethane); HPLC conditions: CHIRALPAK® AS-H column 25:75 IPA: hexane, flow 0.8 mL/min. Retention times: 48.5 min (not resolved), 84.1 min, 102.7 min.

(+)-(1R,4S)-1-{4-[(Methoxycarbonyl)dimethylphosphonomethoxy]cyclopentan-1-yl}thymine (+)-(1R,4S)-26a This was prepared following the procedure described for 25a from the alkene (−)-(1S,4R)-24a (50% e.e., dr 1.2:1) (167 mg, 0.43 mmol) and 5% palladium on carbon (76 mg) in methanol (15 mL). The $^1$H NMR spectrum of the crude product indicated that the desired alkane (+)-(1R,4S)-26a was the major component (~95%, dr 1.2:1). Purification by flash chromatography (SiO$_2$, 5% methanol in dichloromethane) yielded the saturated compound (+)-(1R,4S)-26a as a cream solid (143 mg, 85%, 50% e.e, dr 1:1); m.p. 129-130° C.; $[\alpha]_D^{20}$ +6.11 (c 1.24, dichloromethane); HPLC conditions: CHIRALPAK® AS-H column 25:75 IPA:hexane, flow 0.8 mL/min. Retention times: 48.5 min (not resolved), 84.1 min, 102.7 min.

cis-1-{4-[(Ethoxycarbonyl)diethylphosphonomethoxy]cyclopentan-1-yl}uracil 25b

This compound was prepared following the procedure described for 25a from the alkene 23b (dr 1.2:1) (156 mg, 0.38 mmol) and 10% palladium on carbon (50 mg) in absolute ethanol (15 mL). The $^1$H NMR spectrum of the crude material showed that the alkane 25b was the major component (~90%, dr 1.2:1). Purification by flash chromatography (SiO$_2$, 5% methanol in dichloromethane) afforded the saturated compound 25b as a cream solid (131 mg, 82%, dr 1.1:1); m.p. 106-108° C.; (Found: C, 48.80; H, 6.39; N; 6.30. $C_{17}H_{27}N_2O_8P$ requires C, 48.80; H, 6.50; N, 6.70%); $v_{max}/cm^{-1}$ (KBr) 3174 (NH), 3057 (CH), 2996 (CH), 1755 (C=O), 1702, 1682, 1460, 1273, 1260 (P=O), 1106 (C—N), 1019 (C—O); $\delta_H$ (600 MHz, CDCl$_3$): 1.28-1.38 (9H, m), 1.53-1.65 (1H, m), 1.78-1.89 (2H, m), 2.06 (0.5H, br dd, J~6.6, 7.8), 2.13 (0.5H, br dd, J~6.6, 6.6, 2.20-2.29 (1H, m), 2.33-2.42 (1H, m), 4.15-4.36 (7H, m), 4.35 (0.5H, d, $J_{PH}$=19.2), 4.39 (0.5H, d, $J_{PH}$=19.8), 5.22-5.31 (1H, m), 5.74 (0.5H, d, J=7.8), 5.79 (0.5H, d, J=7.8), 7.95 (0.5H, d, J=8.4), 8.06 (0.5H, d, J=8.4), 8.39 (1H, br s); $\delta_C$ (75.5 MHz, CDCl$_3$): 14.1, 16.39 (br d, $J_{PC}$~5.9), 16.44 (br d, $J_{PC}$~5.6), 30.3, 30.4, 30.6, 31.6, 38.5, 39.0, 53.3, 53.4, 62.0, 62.1, 63.5 (2 d, $J_{PC}$~6.6, 6.6), 63.7 (d, $J_{PC}$=6.6), 64.0 (d, $J_{PC}$=6.6), 73.8 (d, $J_{PC}$=159.8), 74.5 (d, $J_{PC}$=158.9), 81.7 (d, $J_{PC}$=11.5), 82.6 (d, $J_{PC}$=9.1), 102.9, 103.1, 142.7, 142.8, 151.4, 151.5, 163.4 167.2 (br d, $J_{PC}$~1.7), 167.5 (br d, $J_{PC}$~2.3); $\delta_P$ (161.9 MHz, CDCl$_3$): 14.4, 14.6; HRMS (ES+): Exact mass calculated for $C_{17}H_{28}N_2O_8P$ [M+H]$^+$ 419.1583. Found: 419.1586. m/z (ES+) 837.4 [dimer, 40%], 437.2 [(M+Na)$^+$, 15%] 419.2 [(M+H)$^+$, 100%)], 325.1 (10%).

cis-1-{4-[(methoxycarbonyl)dimethylphosphonomethoxy]cyclopentan-1-yl}uracil 26b

This compound was prepared using the procedure described for 25a from the alkene 24b (dr 1.2:1) (75 mg, 0.19 mmol) and 5% palladium on carbon (50 mg) in methanol (10 mL). The $^1$H NMR spectrum of the crude product indicated that the alkane 26b was the main component (~90%, dr 1.2:1). Purification by flash chromatography (SiO$_2$, 5% methanol in dichloromethane) yielded the saturated product 26b as a white hygroscopic gum (69 mg, 86%, 1.1:1); $v_{max}/cm^{-1}$ (film) 3425 (NH), 3198, 2959, 2921 (CH), 1744 (C=O), 1688, 1255 (P=O), 1111 (C—N), 1034 (C—O); $\delta_H$ (600 MHz, CDCl$_3$): 1.57-1.67 (1H, m), 1.78-1.90 (2H, m), 2.04-2.14 [1H, 2 dd, J~6.6, 6.6, 6.6, 6.6), 2.19-2.29 (1H, m), 2.34-2.43 (1H, m), 3.83-3.89 (9H, m), 4.17-4.22 (1H, m), 4.39 (0.55H, d, $J_{PH}$=19.2), 4.44 (0.45H, d, $J_{PH}$=19.8), 5.21-5.30 (1H, m, 5.75 (0.45H, br d, J~7.8)], 5.80 (0.55H, br d, J~7.8), 7.89 (0.45H, br d, J~8.4), 7.98 (0.55H, br d, J~7.8), 8.87 (1H, br s); $\delta_C$ (75.5 MHz, CDCl$_3$): 30.2, 30.6, 31.6, 38.3, 38.9, 53.01, 53.02, 53.4, 53.5, 53.9 (d, $J_{PC}$~6.6), 54.0 (d, $J_{PC}$=6.8), 54.1 (d, $J_{PC}$=6.6), 54.4 (d, $J_{PC}$=6.6), 73.4 ($J_{PC}$=160.8), 74.1 (d, $J_{PC}$=160.0), 82.0 (d, $J_{PC}$=11.2, 82.7 (d, $J_{PC}$=9.3), 102.9, 103.1, 142.4, 142.5, 151.38, 151.41, 163.3, 167.6 (br d, $J_{PC}$~2.0), 167.9 (br d, $J_{PC}$~2.6); $\delta_P$ (121.5 MHz, CDCl$_3$): 16.8, 17.0; HRMS (ES+): Exact mass calculated for $C_{14}H_{22}N_2O_8P$ [M+H]$^+$ 376.1114. Found: 376.1114. m/z (ES+) 753.2 [dimer, 30%], 394.1 [20%] 377.1 [(M+H)$^+$, 100%]. This compound could be stored at room temperature for extended periods with no noticeable decomposition. A sample that was approximately 2 years old was 95% pure by $^1$H NMR analysis.

(−)-(1S,4R)-1-{4-[(methoxycarbonyl)dimethyl-phosphonornethoxy]cyclopentan-1-yl}uracil (−)-(1S,4R)-26b This was prepared following the procedure described for 25a, from the alkene (+)-(1R,4S)-24b (98% e.e., dr 1.1:1) (231 mg, 0.62 mmol) and 5% palladium on carbon (181 mg) in methanol (35 mL). The $^1$H NMR spectrum of the crude material indicated that the alkane (−)-(1S,4R)-26b was the main component (~95%, dr 1.1:1). Purification by flash chromatography (SiO$_2$, 5% methanol in dichloromethane) afforded the saturated compound (−)-(1S,4R)-26b as a cream gum (209 mg, 90%, 98% e.e., dr 1.1:1) [α]$_D^{20}$− 4.55 (c 0.62, dichloromethane); HPLC Conditions: CHIRALCEL® OJ-H column 30:70 IPA:hexane, flow 0.7 mL/min. Retention times: 42.2 min, 47.5 min, 60.6 min, 68.5 min.

(+)-(1R,4S)-1-{4-[(Methoxycarbonyl)dimethyl-phosphonomethoxy]cyclopentan-1-yl}uracil (+)-(1R,4S)-26b This was prepared according to the procedure described for 23a, from the alkene (−)-(1S,4R)-24b (30% e.e., dr 1.1:1) (351 mg, 0.94 mmol) and 5% palladium on carbon (120 mg) in methanol (30 mL). The $^1$H NMR spectrum of the crude material indicated that the alkane (+)-(1R,4S)-26b was the major component (95%, 1.1:1). Purification by flash chromatography (SiO$_2$, 5% methanol in dichloromethane) afforded the saturated compound (+)-(1R,4S)-26b as a white hygroscopic gum (331 mg, 94%, 30% e.e., dr 1.1:1); [α]$_D^{20}$ +1.46 (c 1.13, dichloromethane); HPLC conditions: CHIRALCEL® OJ-H column 30:70 IPA:hexane, flow 0.7 mL/min. Retention times: 42.2 min, 47.5 min, 60.6 min, 68.5 min.

cis-1-{4-[(Ethoxycarbonyl)diethylphosphonomethoxy]cyclopentan-1-yl}cytosine 25c

This was prepared following the procedure described for 23a, from the alkene 23c (dr 1.2:1) (156 mg, 0.26 mmol) and 5% palladium on carbon (68 mg) in absolute ethanol (15 mL). The $^1$H NMR spectrum of the crude product showed the main component was the desired alkane 25c (~75%, dr 1.2:1) Purification by flash chromatography afforded the saturated product 25c as a hygroscopic white solid (128 mg, 82%, dr 1.1:1); $u_{max}/cm^{-1}$ (KBr): 3334 (NH), 3114 (CH), 2984 (CH), 1747 (C=O), 1655, 1618 (C=C), 1525, 1481 (CH), 1368, 1282, 1258 (P=O), 1107, 1027 (C—O); $\delta_H$ (400 MHz, CDCl$_3$): 1.29-1.39 (9H, m), 1.56-1.70 (1H, m), 1.71-1.87 (2H, m), 1.99-2.11 (1H, m), 2.18-2.29 (1H, m), 2.34-2.46 (1H, m), 4.13-4.35 (7H, m), 4.34 (0.5H, d, $J_{PH}$=19.2), 4.39 (0.5H, d, $J_{PH}$=19.2), 5.00-7.01 (2H, br s), 5.33-5.46 (1H, m), 5.82 (0.5H, d, J=7.2), 5.86 (0.5H, d, J=7.6), 7.92 (0.5H, d, J=7.6), 8.03 (0.5H, d, J=7.6); $\delta_C$ (75.5 MHz, CDCl$_3$): 14.1, 16.4 (d, $J_{PC}$~5.9), 30.6, 30.8, 30.9, 31.7, 38.6, 39.1, 54.0, 54.1, 61.99, 62.04, 63.5 (2 d, $J_{PC}$~6.3, 6.5), 63.7 (d, $J_{PC}$=6.6), 64.0 (d, $J_{PC}$=6.6), 74.1 (d, $J_{PC}$=159.8), 74.6 (d, $J_{PC}$=158.9), 82.0 (d, $J_{PC}$=11.7), 82.8 (d, $J_{PC}$=9.8), 94.9, 95.2, 143.6, 143.8, 156.91, 156.94, 165.1, 167.4 (br d, $J_{PC}$~1.9), 167.6, [C, br d, $J_{PC}$~2.3); $\delta_P$ (125.5 MHz, CDCl$_3$) 14.5, 14.6; HRMS (ES+) Exact mass calculated for $C_{17}H_{29}N_3O_7P$ [M+H]$^+$, 418.1743. Found 418.1728; m/z (ES+) [M+H]$^+$ 835.3 [dimer, 100%], 440.1 [(M+Na)$^+$, 15%], 418.1 [(M+H)$^+$, 85%].

cis-1-{4-[(Methoxycarbonyl)dimethylphosphonomethoxy]cyclopentan-1-yl}cytosine 26c This was prepared following the procedure described for 25a, from the alkene 24c (dr 1.1:1) (97 mg, 0.26 mmol) and 5% palladium on carbon (60 mg) in methanol (10 mL).

$^1$H NMR analysis of the crude material showed the major component was the desired alkane 26c (~80%, dr 1.1:1). Purification by flash chromatography (SiO$_2$, 5% methanol in dichloromethane) afforded the saturated product 26c as a white hygroscopic gum (78 mg, 80%, dr 1.1:1); $v_{max}/cm^{-1}$ (film) 3421 (NH), 3198 (CH), 2958 (CH), 1744 (C=O), 1718, 1651, 1531, 1491 (CH), 1260, 1233 (P=O), 1109 (C—N), 1050 (C—O), 1030; $\delta_H$ (300 MHz, CDCl$_3$): 1.58-

1.90 (3H, m), 1.97-2.12 (1H, m), 2.15-2.30 (1H, m), 2.34-2.48 (1H, m), 3.81-3.90 (9H, m), 4.12-4.20 (1H, m), 4.40 (0.5H, d, $J_{PH}$=19.2), 4.44 (0.5H, d, $J_{PH}$=19.8), 5.27-5.44 (1H, m), 5.50-7.31 (2H, br s), 5.90 (0.5H, d, J=7.5), 5.93 (0.5H, d, J=7.5), 7.86 (0.5H, d, J=7.5), 7.94 (0.5H, d, J=7.5); $\delta_C$ (75.5 MHz, CDCl$_3$): 30.6, 30.7, 31.7, 38.5, 39.0, 53.01, 53.04, 53.9-54.3 (m), 73.5 (d, $J_{PC}$=160.7), 74.1 (d, $J_{PC}$=160.0), 82.3 (d, $J_{PC}$=11.2, 82.9 (d, $J_{PC}$=9.5), 95.2, 95.4, 143.4, 143.6, 156.9, 164.9, 167.8 (d, $J_{PC}$=2.3), 168.0 (d, $J_{PC}$=2.7); $\delta_P$ (121.5 MHz, CDCl$_3$): 16.9, 17.0, HRMS (ES+): Exact mass calculated for C$_{14}$H$_{23}$N$_3$O$_7$P [M+H]$^+$ 376.1274. Found 376.1263. m/z (ES+) 751.3 [dimer, 100%], 398.1 [(M+Na)$^+$, 20%] 374.1 [(M+H)$^+$, 50%]. This phosphononucleoside 26c decomposes readily in solvents such as dichloromethane, deuterated chloroform and methanol. Significant decomposition was seen in a sample of 26c in deuterated chloroform after 16 hours at room temperature.

(−)-(1S,4R)-1-{4-[(Methoxycarbonyl)dimethyl-phosphonomethoxy]cyclopentan-1-yl}cytosine (−)-(1S,4R)-26c This compound was prepared, following the procedure described for 25a, from the alkene (+)-(1R,4S)-24c (98% e.e., dr 1.1:1) (167 mg, 0.447 mmol) and 10% palladium on carbon (83 mg) in methanol (25 mL). The $^1$H NMR spectrum of the crude residue indicated the main component was the alkane (−)-(1S,4R)-26c (~70%, dr 1.1:1). Purification by flash chromatography (SiO$_2$, 5% methanol in dichloromethane) afforded the saturated product (−)-(1S,4R)-26c as a colourless hygroscopic gum (98 mg, 58%, 98% e.e., dr 1.2:1). Unable to record optical rotation due to the labile nature of (−)-(1S,4R)-26c in solution. The enantiopurity of (−)-(1S,4R)-26c was not determined directly, but assigned on the basis of the enantiopurity of the acetoxy alcohol (+)-(1R,4S)-16.

(+)-(1R,4S)-1-{4-[(Methoxycarbonyl)dimethyl-phosphonomethoxy]cyclopentan-1-yl}cytosine(+)-(1R,4S)-26c This was prepared following the procedure described for 25a, from the alkene (−)-(1R,4S)-24c (dr 1.2:1) (70% e.e., 171 mg, 0.46 mmol) and 10% palladium on carbon (86 mg) in methanol (35 mL). $^1$H NMR analysis of the crude material indicated the main component was (+)-(1R,4S)-26c (~75%, dr 1.2:1). Purification by flash chromatography (SiO$_2$, 5% methanol in dichloromethane) afforded the saturated product (+)-(1R,4S)-26c as a colourless gum (106 mg, 62%, 70% e.e., dr 1.2:1). Unable to record optical rotation due to the labile nature of (+)-(1R,4S)-26c in solution. The enantiopurity of (+)-(1R,4S)-26c was not determined directly, but assigned on the basis of the enantiopurity of the acetoxy alcohol (−)-(1S,4R)-16.

cis-9-{4-[(Ethoxycarbonyl)diethylphospho-nomethoxy]cyclopentan-1-yl}adenine 25d

This was prepared following the procedure described for 25a, from the alkene N-9-23d (dr 1.2:1) (135 mg, 0.31 mmol) and 5% palladium on carbon (65 mg) in absolute ethanol (10 mL). The crude $^1$H NMR consisted mainly of the desired alkane 25d (~85%, dr 1.2:1) and an unknown impurity (~15%, m at 3.64-3.76 ppm) The material was purified by flash chromatography (SiO$_2$, 5% methanol in dichloromethane) to yield the saturated compound 25d as a white solid (105 mg, 77%, dr 1:1). m.p. 145-147° C., v$_{max}$/cm$^{-1}$ (KBr) 3405, 3194 (NH), 3108 (CH), 2954 (CH), 1739 (C=O), 1649, 1600, 1579, 1508, 1417, 1338, 1234 (P=O), 1108 (C—N), 1069, 1050 (C—O); $\delta_H$ (600 MHz, CDCl$_3$): 1.30-1.40 (9H, m) 1.77-1.89 (1H, m), 2.11-2.23 (3H, m), 2.36-2.45 (1H, m), 2.50-2.60 (1H, m), 4.19-4.36 (7H, m), 4.40 (0.5H, d, $J_{PH}$=18.6), 4.45 (0.5H, d, $J_{PH}$=19.8), 5.14-5.24 (1H, m), 6.32 (1H, br s), 6.37 (1H, br s), 8.34 (1H, s), 8.40 (0.5H, s), 8.54 (0.5H, s); $\delta_C$ (150.9 MHz, CDCl$_3$): 14.1, 16.4-16.5 (m), 30.8, 31.8, 32.1, 32.3, 39.9, 40.4, 52.4, 62.0, 63.6, 63.8 (d, $J_{PC}$=6.5), 64.0 (d, $J_{PC}$=6.6), 74.0 (d, $J_{PC}$=159.2), 74.5 (d, $J_{PC}$=158.5), 81.8 (d, $J_{PC}$=11.8), 82.6 (d, $J_{PC}$=9.8), 119.38, 119.41, 140.0, 140.2, 150.0, 150.01, 152.7, 155.70, 155.72, 167.4, 167.6 $\delta_P$ (162.0 MHz, CDCl$_3$): 14.3, 14.4; HRMS (ES+) Exact mass calculated for C$_{18}$H$_{29}$N$_5$O$_6$P [M+H]$^+$ 442.1855. Found: 442.1841. m/z (ES+) [M+H]$^+$ 442.2 [(M+H)$^+$, 100%], 443.2 [30%], 464.1 [(M+Na)$^+$, 10%].

cis-9-{4-[(Methoxycarbonyl)dimethyl phosphonomethoxy]cyclopentan-1-yl}adenine 26d This compound was prepared using the procedure described for 25a from the alkene N-9-24d (dr 1:1) (210 mg, 0.53 mmol) and 5% palladium on carbon (75 mg) in methanol (15 mL). The $^1$H NMR of the crude material showed that the alkane 25d was the major component (95%, dr 1:1). Purification by flash chromatography (SiO$_2$, 5% methanol in dichloromethane) yielded the saturated product 25d as a white hygroscopic gum (169 mg, 80%, dr 1:1); v$_{max}$/cm$^{-1}$ (film) 3362, 3280 (NH), 3108, 2953, 2922 (CH), 1738 (C=O), 1672, 1601 (C=C), 1230 (P=O), 1108 (C—N), 1073, 1048 (C-0); $\delta_H$ (300 MHz, CDCl$_3$): 1.78-1.94 (1H, m), 2.06-2.27 (3H, m), 2.33-2.48 (1H, m), 2.49-2.64 (1H, m), 3.82-3.92 (9H, m), 4.26-4.35 (1H, m), 4.40 (0.5H, d, $J_{PH}$=19.2), 4.49 (0.5H, d, $J_{PH}$=19.8), 5.11-5.24 (1H, m), 6.02 (1H, br s), 6.05 (1H, br s), 8.35 (1.5H, s), 8.46 (0.5H, s); $\delta_C$ (75.5 MHz, CDCl$_3$): 30.7, 31.8, 32.0, 32.1, 39.7, 40.3, 52.4, 52.5, 53.0, 54.1 (d, $J_{PC}$=6.6), 54.3 (d, $J_{PC}$=6.6), 54.5 (d, $J_{PC}$=6.6), 73.8 (d, $J_{PC}$=160.4), 74.5 (d, $J_{PC}$=159.7), 82.0, 82.8, 119.3, 139.8, 139.9, 149.9, 152.8, 155.76, 155.78, 167.7 (d, $J_{PC}$=2.0), 168.0 (d, $J_{PC}$=2.3); $\delta_P$ (121.5 MHz, CDCl$_3$): 16.6, 16.8; HRMS (ES+): Exact mass calculated for C$_{15}$H$_{23}$N$_5$O$_6$P [M+H]$^+$ 400.1386. Found: 400.1379. m/z (ES+) 422.1 [(M+Na)$^+$, 10%] 401.1 [20%] 400.1 [(M+H)$^+$, 100%] 220.1 [5%], 150.0 [10%].

(−)-(1S,4R)-9-{4-[(Methoxycarbonyl)dimethyl phosphonomethoxy]cyclopentan-1-yl}adenine (−)-(1S,4R)-26d This was prepared according to the procedure described for 25a, from the alkene, (+)-(1R,4S)-24d (98% e.e., dr 1:1) (158 mg, 0.40 mmol) and 5% palladium on carbon (75 mg) in methanol (25 mL). The crude $^1$H NMR spectrum indicated that the desired alkane (−)-(1S,4R)-26d was the main component (~80%, dr 1:1). Purification by flash chromatography (SiO$_2$, 5% methanol in dichloromethane) afforded the saturated product (−)-(1S,4R)-26d as a pale yellow hygroscopic gum 118 mg, 74%, 98% e.e., dr 1:1); [c]$_D^{20}$ −14.33 (c 0.15, dichloromethane). The enantiopurity of (−)-(1S,4R)-26d was not determined directly, but assigned on the basis of the enantiopurity of the acetoxy alcohol (+)-(1R,4S)-16.

(+)-(1R,4S)-9-{4-[(Ethoxycarbonyl)diethylphospho-nomethoxy]cyclopentan-1-yl}adenine (+)-(1R,4S)-26d This was prepared following the procedure described for 25a, from the alkene (−)-(1S,4R)-24d (70% e.e., dr 1.2:1)

(253 mg, 0.64 mmol) and 10% palladium on carbon (100 mg) in methanol (20 mL). The reaction mixture was shaken under hydrogen at 40 psi at room temperature for 20 h. $^1$H NMR analysis of the crude material indicated that the alkane (+)-(1R,4S)-26d was the major component (~90%, dr 1.2:1). Purification by flash chromatography (SiO$_2$, 5% methanol in dichloromethane) afforded the saturated product (+)-(1R,4S)-26d as a pale yellow hygroscopic gum (189 mg, 74%, 70% e.e, dr 1.1:1); [c]$_D^{20}$ +10.00 (c 0.2, dichloromethane). Note: Impurity seen at 2.4 ppm (~0.6H) in the $^1$H NMR spectrum. The enantiopurity of (+)-(1R,4S)-26d was not determined directly, but assigned on the basis of the enantiopurity of the acetoxy alcohol (−)-(1S,4R)-16.

cis-2-Amino-7-{4-[(methoxycarbonyl)dimethylphosphonornethoxy]cyclopentan-1-yl}-6-chloropurine 26e This was prepared following the procedure described for 25a, from the alkene N-7-24e (dr 1.2:1) (161 mg, 0.28 mmol) and 10% palladium on carbon (54 mg) in methanol (10 mL). Purification by flash chromatography (SiO$_2$, 5% methanol in dichloromethane) yielded the saturated compound N-7-26e as a cream solid (21 mg, 17%, dr 1:1); $\delta_H$ (300 MHz, CDCl$_3$): 1.80-2.61 (6H, m), 3.81-3.90 (9H, m), 4.26-4.38 (1H, m), 4.40 (0.5H, d, $J_{PC}$=19.2), 4.45 (0.5H, d, $J_{PC}$=20.1), 5.13 (1H, br s), 5.14 (1H, br s), 5.31-5.44 (1H, m), 8.57 (0.5H, br s), 8.64 (0.5H, br s). Signals for the alkene N-7-24e were seen at 5.78-5.89 (0.1H, m), 6.20-6.27 (0.1H, m), 6.44-6.50 (0.1H, m), 8.19 (0.04H, s) and 8.20 (0.06H, s). The product underwent significant decomposition within 4 days in solution and no further analysis could be obtained. The presence of some unsaturated compound N-7-24e appears to cause decomposition with all the derivatives at this point in the synthesis.

Deprotection Reactions
General Procedure for the Purification of Phosphonic Acids Via Charcoal Chromatography.

The charcoal column was prepared using activated carbon G-60 made from a sintered glass funnel packed with activated charcoal, placed on a Büchner funnel and connected to a vacuum source. A thin layer of Celite® (~2 mm) was first put on the sintered glass funnel and then the charcoal (mass of ~10-20 times the sample requiring purification) was packed on top of the Celite®. Vacuum was used to elute the column. Before use, the charcoal pad was aqueous ammonia (20%, ~4 times the height of the charcoal pad), water (~6 times the height of the charcoal pad) and finally methanol (~4 times the height of the charcoal pad). The fully deprotected compounds 11a-d are not stable in acidic solutions thus, in each case the material isolated from the base catalysed deprotection was dissolved in the minimum amount of water and the solution was adjusted to pH 1-2.5 immediately prior to adsorption onto the charcoal column. Following adsorption of the phosphonic acid, the charcoal pad was then washed with water to remove inorganic impurities (150 mL for 100 mg of sample), followed by elution with 20% aqueous ammonia to release the pure phosphononucleoside as its ammonium salt. The fractions were spotted on a TLC plate and the UV active fractions were combined and concentrated in vacuo. The partially deprotected compound 298a was eluted with 10:10:3 ethanol/water/ammonia.

cis-1-{4-[Methoxycarbonyl(phosphono)methoxy] cyclopentan-1-yl}thymine 28a

Bromotrimethylsilane (0.23 mL, 265 mg, 1.73 mmol) was added via syringe to a stirring solution of 26a (dr 1.2:1) (135 mg, 0.35 mmol) in dichloromethane (20 mL) under a nitrogen atmosphere. The reaction mixture was stirred for 6 h overnight prior to the addition of water (1 mL). Stirring was continued for 30 min and the reaction mixture was then concentrated in vacuo at 30° C. to give a pale orange gum (121 mg, 96%). The acidic residue was purified by a charcoal column to afford 28a as the ammonium salt (86 mg, 45%, 1:1); $\delta_H$ (300 MHz, D$_2$O): 1.51-2.04 (5H, m), 1.787 (1.5H, s), 1.790 (1.5H, s), 2.26-2.36 (1H, m), 3.66 (1.5H, s), 3.67 (1.5H, s), 3.99-4.10 (1H, m), 4.24 (0.5H, d, $J_{PH}$=18.6), 4.27 (0.5H, d, $J_{PH}$=18.9), 4.78-4.92 (1H, m), 7.73 (0.5H, br q, J=0.9), 7.82 (0.5H, br q, J=0.9); by (121 MHz, D$_2$O): 9.1, 9.5.

cis-1-{4-[Carboxy(phosphono)methoxy]cyclopentan-1-yl}thymine 11a

Bromotrimethylsilane (260 mg, 0.22 mL, 1.7 mmol) was added via syringe to a stirring solution of 26a (dr 1.2:1) (133 mg, 0.34 mmol) in dichloromethane (20 mL) at 0° C. under a nitrogen atmosphere. The reaction mixture was then allowed to warm slowly to room temperature and stirred overnight. The dark orange solution was treated with water (1 mL) and the reaction mixture was stirred for 30 min to give a milky solution. Sodium hydroxide (1M, 3.5 mL, ~3.5 mmol, 10 eq.) was added and the reaction mixture was stirred overnight at room temperature before concentration in vacuo to give a white solid. The $^1$H NMR spectrum of the crude material showed the product 11a was the major component (~95%, dr 1:1). The acidic residue was purified by charcoal chromatography and the fractions containing the phosphonate were lyophilised to afford the fully deprotected phosphonate 11a as the ammonium salt (56 mg, 45%, 1:1); m.p. 228-230° C.; $v_{max}$/cm$^{-1}$ (KBr) 3152 (NH), 3025 (CH), 1691 (C=O), 1405, 1273 (P=O), 1058; $\delta_H$ (600 MHz, D$_2$O): 1.53-1.62 (0.5H, m), 1.62-1.75 (2.5H, m), 1.76 (3H, s), 1.80-1.98 (2H, m), 2.24-2.31 (1H, m), 3.92 (0.5H, d, PCH, $J_{PC}$=18.6), 3.95-4.02 (1.5H, m), 4.73-4.84 (1H, m), 7.70 (0.5H, s), 7.72 (0.5H, s); $\delta_C$ (150.9 MHz, D$_2$O): 11.4, 11.5, 29.1, 29.2, 29.5, 30.6, 36.6, 37.5, 54.6, 54.8, 77.5 (d, $J_{PC}$=143.5), 78.2 (d, $J_{PC}$=143.4), 79.9 (d, $J_{PC}$=11.2), 80.6 (d, $J_{PC}$=10.9), 111.3, 111.4, 140.3, 140.5, 152.57, 152.59, 166.6, 176.3, 176.5; $\delta_P$ (121.5 MHz, CDCl$_3$): 12.4, 12.6; HRMS (ES+): Exact mass calculated for C$_{12}$H$_{18}$N$_2$O$_8$F [M+H]$^+$, 349.0801. Found 349.0804. m/z (ES+) 719.1 (30%), 445.0 (5%), 349.0 [(M+H)$^+$, 10%], 371.0 [(M+Na)$^+$, 20%], 99.9 (30%), 58.9 (100%).

(+)-(1S,4R)-1-{4-[Carboxy(phosphono)methoxy]cyclopentan-1-yl}thymine (+)-(1S,4R)-11a This was prepared as above starting from bromotrimethylsilane (371 mg, 0.32 mL, 2.42 mmol), (−)-(1S,4R)-26a (98% e.e., dr 1:1.2) (187 mg, 0.48 mmol) in dichloromethane (20 mL). The mixture was stirred overnight prior to the addition of water (0.3 mL). Stirring was continued for 30 min and aqueous sodium hydroxide (1M, 5 mL, ~5.0 mmol, 10 eq.) was then added. The mixture was stirred overnight at 50° C. before concentration in vacuo. $^1$H NMR analysis indicated that the main component of the crude material was the desired deprotected compound (~95%, dr 1:1.2). The crude material was purified by charcoal chromatography and lyophilised to afford the fully deprotected phosphonate (+)-(1S,4R)-11 as its ammonium salt (81 mg, 46%, 98% e.e., dr 1:1); m.p. 225-227° C.; $v_{max}$/cm$^{-1}$ (KBr) 3204 (NH), 3025 (CH), 1691 (C=O), 1588 (C=C), 1433 (CH), 1273 (P=O), 1157 (C—N), 1057 (C—O); $\delta_H$ (300 MHz, D$_2$O):

1.65-2.17 (5H, m), 1.93 (3H, s), 2.36-2.50 (1H, m), 4.04-4.21 (2H, m), 4.87-5.05 (1H, m), 7.89 (1H, br s). The enantiopurity of (+)-(1'S, 4'R)-11a was not determined directly, but assigned on the basis of the enantiopurites of the acetoxy alcohol (+)-(1R,4S)-16 and of the saturated product (−)-(1S,4R)-26a.

(−)-(1R,4S)-1-{4-[Carboxy(phosphono)methoxy] cyclopentan-1-yl}thymine(−)-(1R,4S)-11a This was prepared as above form bromotrimethylsilane (231 mg, 0.2 mL, 1.51 mmol), (+)-(1R,4S)-26 (70% e.e., dr 1:1) (118 mg, 0.30 mmol) in dichloromethane (20 mL) followed by water (0.2 mL) then aqueous sodium hydroxide (1M, 3 mL, ~3 mmol, 10 eq). $^1$H NMR analysis of the crude residue indicated that the main component was the desired deprotected compound (−)-(1R,4S)-11a (~95%, dr 1:1). The crude residue was purified by charcoal column chromatography and lyophilised to afford the fully deprotected phosphonate (−)-(1R,4S)-11a as the ammonium salt (63 mg, 57%, 70% e.e., dr 1:1.1); m.p. 229-230° C. The enantiopurity of (−)-(1R,4S)-11a was not determined directly, but assigned on the basis of the enantiopurites of the acetoxy alcohol (−)-(1S,4R)-16 and of the saturated product (+)-(1R,4S)-26a.

(1S,4R)-1-{4-[Methoxycarbonyl(phosphono) methoxy]cyclopentan-1-yl}uracil (1S,4R)-28b This was prepared from bromotrimethylsilane (302 mg, 0.26 mL, 1.97 mmol), (−)-(1S,4R)-26b (98% e.e., dr 1.2:1) (147 mg, 0.39 mmol) in dichloromethane (20 mL). After stirring overnight, the dark orange solution was then treated with water (0.2 mL) and the resulting milky solution was stirred for 10 min before concentration in vacuo to give (1S,4R)-28b (131 mg, 96% yield, 98% e.e.).

cis-1-{4-[Carboxy(phosphono)methoxy]cyclopentan-1-yl}uracil 11 b

This was prepared from bromotrimethylsilane (209 mg, 0.18 mL, 1.37 mmol), 26b (dr 1.5:1) (103 mg, 0.27 mmol) in dichloromethane (20 mL) which had been equilibrated at 0° C., under a nitrogen atmosphere. The reaction mixture was allowed to warm slowly to room temperature and stirred for 15 h. The solution was treated with water (0.1 mL) and stirred for 10 min. Aqueous sodium hydroxide (1M, 5 mL, ~5.0 mmol, 18 eq.) was then added the mixture was stirred at 50° C. overnight before concentration in vacuo. $^1$H NMR analysis of the crude residue indicated that the main component was the desired compound 11b (~95%, dr 1.5:1). The crude residue was purified by charcoal. The fractions containing the pure phosphonate were lyophilised to afford the fully deprotected phosphonate 11 b as the ammonium salt (55 mg, 58%, dr 1.1:1); $v_{max}/cm^{-1}$ (KBr) 3201 (OH), 3052 (CH), 1686 (C=O), 1273 (P=O), 1152 (C—O), 1062 (C—N); $\delta_H$ (600 MHz, D$_2$O): 1.51-1.60 (0.5H, m), 1.60-177 (2.5H, m), 1.82-1.93 (1H, m), 1.94-2.02 (1H, m), 2.21-2.31 (1H, m), 3.90 (0.5H, d, $J_{PC}$=18.6), 3.91-4.03 (1.5H, m), 4.80-4.88 (1H, m), 5.74 (0.5H, br d, $J_{PC}$~7.8), 5.75 (0.5H, br d, $J_{PC}$~7.2), 7.99 (1H, br d, J~7.8); $\delta_C$ (150.9 MHz, D$_2$O): 29.5, 29.7, 31.1, 36.5, 37.7, 54.9, 55.1, 77.5 (br d, $J_{PC}$~144.0)*, 78.1 (br d, $J_{PC}$~143.5)*, 80.0 (d, $J_{PC}$=11.3, 80.7 (d, $J_{PC}$=11.5), 102.1, 102.2, 145.35, 145.38, 152.6, 152.7, 166.5, 176.4, 176.6; $\delta_P$ (161.9 MHz, CDCl$_3$): 12.17, 12.23; HRMS (ES+): Exact mass calculated for C$_{11}$H$_{16}$N$_2$O$_8$P [M+H]$^+$ 335.0644. Found: 335.0628. m/z (ES+) 667.2 (dimer, 50%), 333.0 [(M+H)$^+$, 100%].

*PCH signals were not seen in the regular $^{13}$C NMR spectrum however, these peaks were visible in the DEPT spectra. The coupling constants for PCH were taken from the DEPT 90 spectrum.

(+)-(1S,4R)-1-{4-[Carboxy(phosphono)methoxy] cyclopentan-1-yl}uracil(+)-(1S,4R)-11b Aqueous sodium hydroxide (1M, 5 mL, ~5 mmol, 18 eq) was added to a stirring solution of (+)-(1S,4R)-28b* (98% e.e., dr 1:1) (131 mg, 0.38 mmol). The reaction mixture was stirred at 50° C. overnight before concentration in vacuo. $^1$H NMR analysis indicated of the crude residue indicated that the desired compound (+)-(1S,4R)-11b was the main component (~98%, dr 1:1). The crude residue was purified by charcoal chromatography and lyophilised to afford the fully deprotected phosphonate (+)-(1S,4R)-11b as its ammonium salt (63 mg, 48%, 98% e.e., 1:1); $[\alpha]_D^{20}$ +8.30 (c 0.24, water).

*Sample used directly from experiment above without purification.

The enantiopurity of (+)-(1S,4R)-11b was not determined directly, but assigned on the basis of the enantiopurites of the acetoxy alcohol (+)-(1R,4S)-16, the phosphonucleoside(+)-(1R,4S)-24b and of the saturated product (−)-(1S,4R)-26b.

(−)-(1R,4S)-1-{4-[Carboxy(phosphono)methoxy] cyclopentan-1-yl}uracil (−)-(1R,4S)-11b This was prepared using bromotrimethylsilane (348 mg, 0.30 mL, 2.27 mmol), (+)-(1R,4S)-26b (30% e.e., dr 1.1:1) (183 mg, 0.49 mmol) in dichloromethane (20 mL) after 18 h, the solution was treated with water (0.2 mL) for 10 min and the mixture was then concentrated in vacuo. The orange residue treated with aqueous sodium hydroxide (1M, 4.9 mL, ~4.90 mmol, 10 eq.) at 50° C. overnight. $^1$H NMR analysis of the crude residue indicated that the phosphonic acid (−)-(1R,4S)-11 b was present as the main component (~95%, dr 1:1). The crude material was purified by charcoal chromatography and lyophilised to afford the fully deprotected phosphonate (−)-(1R,4S)-11b as its ammonium salt (81 mg, 45%, 30% e.e., dr 1.1:1); $[\alpha]_D^{20}$ −1.23 (c 0.29, water). The enantiopurity of (−)-(1R,4S)-11b was not determined directly, but assigned on the basis of the enantiopurites of the acetoxy alcohol (−)-(1S,4R)-16, the phosphononucleoside (−)-(1S,4R)-24b and of the saturated product (+)-(1R,4S)-26b.

cis-1-{4-[Methoxycarbonyl(phosphono)methoxy] cyclopentan-1-yl}cytosine 28c

This was prepared from bromotrimethylsilane (0.23 mL, 1.70 mmol, 7 eq), 26c (dr 1.2:1) (95 mg, 0.25 mmol) in dichloromethane (10 mL). The mixture was heated under reflux for 8 h before treatment with water (0.1 mL). Stirring was continued for 10 min then the solution was concentrated in vacuo to give 28c (88 mg, 100%, dr 1:1); $\delta_H$ (300 MHz, D$_2$O): 1.49-1.80 (3H, m), 1.80-1.97 (1H, m), 2.03-2.14 (1H, m), 2.19-2.31 (1H, m), 3.65 (2.6H, s), 4.00-4.12 (1H, m), 4.33 (0.5H, d, $J_{PH}$=19.2), 4.37 (0.5H, d, $J_{PH}$=19.5), 4.83-5.02 (1H, m), 6.06 (0.5H, d, J=7.8), 6.13 (0.5H, d, J=7.8), 8.11 (0.5H, d, J=7.8), 8.16 (0.5H, d, J=8.1). Additional peak seen in spectrum at 8.06 ppm (d, $J_{PC}$=8.1) due to partial hydrolysis of the carboxyl ester (10%). This explains the low integration on the carboxylic acid methyl ester signal at 3.65 ppm.

cis-1-{4-[Carboxy(phosphono)methoxy]cyclopentan-1-yl}cytosine 11c

Aqueous sodium hydroxide (1M, 2.5 mL, ~2.5 mmol, 10 eq) was added to a stirring solution of 28c* (88 mg, 0.25 mmol, dr 1:1) in water (10 mL) and the reaction mixture was stirred for 28 h at 40° C. before concentration in vacuo. $^1$H NMR analysis of the crude residue indicated that the main component was the fully deprotected compound 11c (~90%, dr 1:1). The crude material was purified by charcoal chromatography and lyophilised to afford the fully deprotected phosphonate 11c (58 mg, 66%, dr 1:1); m.p.>250° C.; $u_{max}$/cm$^{-1}$ (KBr): 3432 (br, NH), 2966 (CH), 1723 (C=O), 1650, 1595 (C=C), 1490, 1399, 1286 (P=O), 1172 (C—N), 1087 (C—O); $\delta_H$ (600 MHz, D$_2$O): 1.52-1.60 (0.5H, m), 1.60-1.72 (2.5H, m), 1.81-1.92 (1H, m), 1.93-2.01 (1H, m), 2.19-2.31 (1H, m), 3.88 (0.5H, d, $J_{PH}$=18.0), 3.91-3.95 (0.5H, m), 3.92 (0.5H, d, $J_{PH}$=18.6), 3.96-4.00 (0.5H, m), 4.82-4.90 (1H, m), 5.915 (0.5H, d, J=7.2), 5.923 (0.5H, d, J=7.8), 7.96 (0.5H, d, J=7.2), 7.97 (0.5H, d, J=7.2; $E_{PC}$ (150 MHz, D$_2$O): 29.4, 30.0, 30.3, 31.1, 36.6, 37.9, 55.3, 55.6, 77.7 (d, $J_{PC}$=142.1), 78.4 (d, $J_{PC}$=141.4, 79.8 (d, $J_{PC}$=11.5), 80.5 (d, $J_{PC}$=11.8), 96.30, 96.34, 144.7, 144.8, 158.42, 158.45, 165.35, 165.37, 176.8, 177.1; $\delta_P$ (121.5 MHz, D$_2$O): 11.3, 11.5; HRMS (ES+): Exact mass calculated for C$_{11}$H$_{17}$N$_3$O$_7$P [M+H]$^+$ 334.0804. Found: 334.0802. m/z (ES−), 523.0 (20%), 332.0 [(M−H)$^-$, 100%], 80.8 (30%).

*Sample of 28c used directly from experiment above without purification.

(+)-(1S,4R)-1-{4-[Carboxy(phosphono)methoxy]cyclopentan-1-yl}cytosine (+)-(1S,4R)-11c Prepared from bromotrimethylsilane (0.18 mL, 1.4 mmol, 5 eq), (−)-(1S,4R)-26c (98% e.e., dr 1.2:1) (98 mg, 0.26 mmol) in dichloromethane (15 mL), followed by aqueous sodium hydroxide (1M, 2.6 mL, ~2.6 mmol, 10 eq). at 50° C. for 18 h before concentration in vacuo. $^1$H NMR analysis of the crude residue indicated that the main component was the fully deprotected compound (+)-(1S,4R)-11c (~90%, dr 1.1:1). The crude material was purified by charcoal chromatography and lyophilised to give the product as a fine cream solid (+)-(1S,4R)-11c (51 mg, 56% yield, 98% e.e., dr 1.1:1); m.p.>250° C.;

(−)-(1R,4S)-1-{4-[Carboxy(phosphono)methoxy]cyclopentan-1-yl}cytosine (−)-(1R,4S)-11c Prepared using bromotrimethylsilane (0.12 mL, 0.9 mmol, 5 eq), (+)-(1R,4S)-26c (70% e.e., dr 1.2:1) (67 mg, 0.18 mmol) in dichloromethane (15 mL), followed by sodium hydroxide (1M, 1.8 mL, ~1.8 mmol, 10 eq) at 50° C. for 18 h prior to concentration in vacuo. $^1$H NMR analysis of the crude residue indicated that the main component was the fully deprotected compound (−)-(1R,4S)-11c (~70%, dr 1.1:1). The crude material was purified by charcoal chromatography and lyophilised to afford the fully deprotected phosphonate (−)-(1R,4S)-11c as a fine cream solid (26 mg, 41%, 70% e.e., dr 1.1:1); m.p.>250° C. The enantiopurity of (−)-(1R,4S)-11c was not determined directly, but assigned on the basis of the enantiopurites of the acetoxy alcohol (−)-(1S,4R)-16.

cis-9-{4-[Methoxycarbonyl(phosphono)methoxy]cyclopentan-1-yl}adenine 28d

Prepared using bromotrimethylsilane (0.08 mL, 0.60 mmol) and 26d (dr 1.1:1) (45 mg, 0.11 mmol) in dichloromethane (15 mL) under reflux for 9 h, followed by water (0.1 mL). Stirring was continued for 10 min before the reaction mixture was concentrated in vacuo at room temperature to give compound 28d (38 mg, 93%, dr 1:1). $\delta_H$ (300 MHz, D$_2$O): 1.77-2.26 (4H, m), 2.20-2.37 (1H, m), 2.41-2.55 (1H, m), 3.67 (1.5H, s), 3.70 (1.5H, s), 4.16-4.27 (1H, m), 4.37 (0.5H, d, $J_{PC}$=18.9), 4.42 (0.5H, d, $J_{PC}$=19.2), 4.94-5.08 (1H, m), 8.32 (1H, s), 8.63 (0.5H, s), 8.71 (0.4H, s).

cis-9-{4-[Carboxy(phosphono)methoxy]cyclopentan-1-yl}adenine 11d

This was prepared from bromotrimethylsilane (240 mg, 0.21 mL, 1.57 mmol), 26d (dr 1.1:1) (125 mg, 0.31 mmol) and dichloromethane (15 mL), under reflux for 7 h. Followed by water (0.1 mL) for 10 min then and aqueous sodium hydroxide (1M, 3.1 mL, 3.10 mmol, 10 eq.) at 50° C. overnight. The reaction mixture was concentrated in vacuo and purified by charcoal chromatography as and lyophilized to afford the fully deprotected phosphonate 11d as its ammonium salt (86 mg, 71%, dr 1.2:1); m.p. 236-240° C.; $v_{max}$/cm$^{-1}$ (KBr) 3342 (NH), 3198, 2961 (CH), 1603 (C=O), 1396, 1176 (C—N), 1071 (C—O); $\delta_H$ (600 MHz, D$_2$O): 1.86-2.23 (5H, m), 2.55-2.64 (1H, m), 3.91 (0.55H, d, $J_{PC}$=16.8), 3.96 (0.45H, d, $J_{PC}$=16.8), 4.09-4.17 (1H, m), 4.75-4.83 (1H, m [partially obscured by water]), 8.11 (0.45H, s), 8.12 (0.55H, s), 8.45 (0.45H, s), 8.50 (0.55H, s); 6c (150 MHz, D$_2$O): 29.3, 30.5, 30.6, 30.7, 37.5, 38.6, 53.6, 53.8, 77.4 (d, $J_{PC}$=145.9), 78.1 (d, $J_{PC}$=148.8), 79.9 (d, $J_{PC}$=10.3), 80.5 (d, $J_{PC}$=10.7), 117.8, 117.9, 141.11, 141.14, 148.2, 151.2, 154.5, 154.6, 176.6, 176.8; $\delta_P$ (121.5 MHz, D$_2$O): 11.7, 11.8; HRMS (ES+): Exact mass calculated for C$_{12}$H$_{17}$N$_5$O$_6$P [M+H]$^+$ 358.0916. Found: 358.0898. m/z (ES−), 370.1 (20%), 356.1 [(M−H)$^-$, 40%], 90.9 (50%), 77.8 (80%), 44.9 (100%). A sample of 11d checked after 1 year showed ~10% degradation.

(+)-(1S,4R)-9-{4-[Carboxy(phosphono)methoxy]cyclopentan-1-yl}adenine (+)-(1S,4R)-11d Prepared from bromotrimethylsilane (218 mg, 0.19 mL, 1.43 mmol) and (−)-(1S,4R)-26d (98% e.e., dr 1:1) (114 mg, 0.29 mmol) in dichloromethane (15 mL), followed by water (0.1 mL) and aqueous sodium hydroxide (1M, 2.9 mL, ~2.90 mmol, 10 eq.) at 50° C. before concentration in vacuo. $^1$H NMR analysis of the crude residue indicated that the desired compound (+)-(1S,4R)-11d was the major component (~85%, dr 1:1). The crude material was purified by charcoal chromatography and lyophilised to afford the fully deprotected phosphonate (+)-(1S,4R)-11d as the ammonium salt (88 mg, 78%, 98% e.e., dr 1.1:1); m.p. 234-239° C.; $[\alpha]_D^{20}$ +13.50 (c 0.2, dichloromethane) The enantiopurity of (+)-(1S,4R)-11d was not determined directly, but assigned on the basis of the enantiopurites of the acetoxy alcohol (+)-(1R,4S)-16.

(−)-(1R,4S)-9-{4-[Carboxy(phosphono)methoxy]cyclopentan-1-yl}adenine (−)-(1R,4S)-11d Prepared from bromotrimethylsilane (239 mg, 0.21 mL, 1.55 mmol) and (−)-(1R,4S)-26d (70% e.e, dr 1.1:1) (122 mg, 0.31 mmol) in dichloromethane (15 mL) under reflux for 9 h, followed by water (0.1 mL) then aqueous sodium hydroxide (1M, 3.0 mL, ~3.0 mmol, 10 eq.) overnight at 50° C. $^1$H NMR analysis of the crude residue indicated that the desired phosphonate (−)-(1R,4S)-11d was the major product (~90%, dr 1.1:1). The crude material was purified by charcoal chromatography and lyophilised to afford the fully deprotected phosphonate (−)-(1R,4S)-11d as the ammonium salt (59 mg, 59%, 70% e.e., dr 1.1:1); m.p. 237-241° C.; $[\alpha]_D^{20}$ −6.70 (c 1.00, dichloromethane). The enantiopurity of (−)-(1R,4S)-11d was not determined directly, but assigned on the basis of the enantiopurites of the acetoxy alcohol (−)-(1S,4R)-16.

Phosphorylation Reactions[42,59]

cis-1-{4-[Methoxycarbonyl(phosphono)methoxy]cyclopentan-1-yl}thymine monophosphate 13

This monophosphorylation of 28a was carried out following the procedures described by Hoard et al.[59] and Debarge et al.[42] Bromotrimethylsilane (0.24 mL, 278 mg, 1.82 mmol) was added via syringe to a stirring solution of 26a (dr 1.1:1) (141 mg, 0.35 mmol) in dichloromethane (20 mL) under a nitrogen atmosphere. The reaction mixture was stirred for 6 h overnight prior to the addition of water (1 mL). Stirring was continued for 30 min and then the reaction mixture was concentrated in vacuo at 30° C. The resulting residue was dissolved in methanol (10 mL) and the solution was treated with tributylamine (0.26 mL, 1.08 mmol). The solution was stirred for 30 min before concentration in vacuo at 30° C. and the residue was dried on the vacuum pump overnight. The resulting residue was dissolved in N,N-dimethylformamide (15 mL) and 1,1-carbonyldiimidazole (235 mg, 1.44 mmol) was added. The mixture was stirred overnight before treatment with methanol (0.2 mL) and stirring was continued for 30 min. Tributylammonium phosphate (1M solution in anhydrous DMF) (2.2 mL, 2.2 mmol) was added and stirring was continued overnight. The reaction was terminated by the addition of water (20 mL) and the solution was then directly applied to a column of DEAE sephadex A-25 (2 g) that had been equilibrated in 50 mM ammonium bicarbonate. The column was then eluted with 250 mL of 50 mM ammonium bicarbonate and then the desired product eluted with 100 mL of 100 mM ammonium bicarbonate. The fractions were combined and concentrated in vacuo to give the desired monophosphorylated compound 13a as a fine white solid (81 mg, 52%, 1.2:1) $\delta_H$ (300 MHz, D$_2$O): 1.60-2.13 (5H, m), 1.87 (3H, s), 2.30-2.45 (1H, m), 3.745 (1.35H, s), 3.751 (1.65H, s), 4.08-4.17 (0.45H, m), 4.17-4.26 (0.55H, m), 4.51 (0.28H, d, $J_{PH}$=19.2), 4.60 (0.23H, d, $J_{PH}$=19.2), 4.84-4.98 (1H, m), 7.79 (0.45H, s), 7.91 (0.55H, s) (Slow deuterium/hydrogen exchange of the PCH proton seen in the $^1$H NMR spectrum with the PCH proton integrating for 0.5 protons); $\delta_C$ (125.8 MHz, D$_2$O): 11.6, 29.2, 29.3, 30.1, 30.3, 37.3, 37.6, 53.0, 54.7, 54.8, 75.7 (br d, $J_{PC}$~151.0), 76.2 (br d, $J_{PC}$~154.0), 81.5 (d, $J_{PC}$=9.8), 82.1 (d, $J_{PC}$=8.7), 111.4, 111.5, 140.6, 140.7, 152.7, 166.7, 172.2, 172.4; $\delta_P$ (121.5 MHz, D$_2$O): 0.6 (m), −10.1 (m); HRMS (ES+): Exact mass calculated for C$_{13}$H$_{21}$N$_2$O$_{11}$P$_2$ [M+H]$^+$, 443.0629. Found 443.0621. m/z (ES+) 884.8 (dimer, 60%), 443.0 [(M+H)$^+$, 100%], %), 363.1 (phosphonate, 25%), 345.1 (40%), 59.1 (30%).

cis-1-{4-[Carboxy(phosphono)methoxy]cyclopentan-1-yl}thymine monophosphate 12a

Following the procedure described by Debarge et al.[42] for similar compounds, sodium hydroxide (1M, 0.5 mL, 0.5 mmol) was added to a solution of 13a* (45 mg, 0.1 mmol) in water (5 mL) and the mixture was stirred overnight at room temperature before concentration in vacuo to give the product 12a (48 mg, dr 1:1) as a white solid; $\delta_H$ (300 MHz, D$_2$O): 1.68-2.14 (5H, m), 1.91 (3H, s), 2.36-2.55 (1H, m, 4.10-4.25 (1H, m), 4.17 (0.5H, d, $J_{PH}$=18.9), 4.22 (0.5H, d, $J_{PH}$=18.9), 4.80-4.98 (1H, m), 7.68 (0.5H, s), 7.70 (0.5H, s); $\delta_C$ (75.5 MHz, D$_2$O): 12.6, 28.9, 29.0, 29.7, 30.0, 36.9, 37.3, 54.4, 54.5, 80.0 (d, $J_{PC}$=11.7), 80.2 (d, $J_{PC}$=11.2), 111.4, 111.5, 139.0, 159.7, 175.0, 176.9; by (121.5 MHz, D$_2$O): 4.5, 4.2, −5.0 (d, J=2.9), −5.2 (d, J=2.7);

*Sample used directly from experiment described above.

cis-1-{4-[Methoxycarbonyl(phosphono)methoxy]cyclopentan-1-yl}thymine diphosphate 15a The diphosphorylation of 28a was carried out following the procedures described by Hoard et al.[59] and Debarge et al.[12] Bromotrimethylsilane (0.17 mL, 197 mg, 1.29 mmol) was added via syringe to a stirring solution of 24a (dr 1:1) (101 mg, 0.25 mmol) in dichloromethane (30 mL) under a nitrogen atmosphere. The reaction mixture was stirred for 7 h prior to the addition of water (1 mL). Stirring was continued for 30 min and then the reaction mixture was concentrated in vacuo at 30° C. The resulting residue was dissolved in methanol (10 mL) and the solution was treated with tributylamine (0.7 mL, 0.29 mmol). The solution was stirred for 30 min before concentration in vacuo at 30° C. and the residue was dried on the vacuum pump overnight. The resulting residue was dissolved in N,N-dimethylformamide (15 mL) and 1,1-carbonyldiimidazole (258 mg, 1.59 mmol) was added. The mixture was stirred for 5 h before treatment with methanol (0.2 mL, 4.18 mmol) and stirring was continued for 30 min. Tributylammonium pyrophosphate (820 mg, 1.49 mmol) was added and stirring was continued overnight. The reaction was terminated by the addition of water (15 mL) and the solution was then directly applied to a column of DEAE sephadex A-25 (2 g) that had been equilibrated in 50 mM ammonium bicarbonate. The column was then eluted with 250 mL of 50 mM ammonium bicarbonate and then the desired product eluted with 100 mL of 100 mM ammonium bicarbonate. The fractions were combined and concentrated in vacuo to give the desired diphosphorylated compound 15a as a fine white solid (28 mg, 22%, dr 1:1.2); $\delta_H$ (500 MHz, D$_2$O): 1.71-2.17 (5H, m), 1.93 (3H, s), 2.38-2.51 (1H, m), 3.82 (1.65H, s), 3.83 (1.35H, s), 4.17-4.25 (0.55H, m), 4.25-4.32 (0.45H, m), 4.56 (0.45H, d, $J_{PH}$=20.0), 4.62 (0.55H, d, $J_{PH}$=20.0), 4.91-5.01 (1H, m), 7.84 (0.55H, s), 7.96 (0.45H, s); $\delta_C$ (125.8 MHz, D$_2$O): 11.6, 29.1, 29.2, 30.1, 30.3, 37.4, 37.6, 53.1, 54.7, 54.8, 81.6 (d, $J_{PC}$=10.1), 82.2 (d, $J_{PC}$=8.8), 111.4, 111.5, 140.5, 140.7, 152.7, 166.7, 172.0 [C, CO$_2$CH$_3$, one diastereomer], 172.2 [C, CO$_2$CH$_3$, one diastereomer]; $\delta_P$ (121.5 MHz, D$_2$O): 0.27*, −9.0, −21.5, −22.6; HRMS (ES+): Exact mass calculated for C$_{13}$H$_{22}$N$_2$O$_{14}$P$_3$ [M+H]$^+$, 523.0284. Found 523.0305. m/z (ES+) 544.8 [(M+Na)$^+$, 30%], 522.9 [(M+H)$^+$, 20%], 464.9 [monophosphate+Na)$^+$, 30%], 442.9 (monophosphate, 20%), 363.1 (phosphonate, 30%), 110.1 (30%), 69.1 (50%), 64.0 (100%).

*Peak at 0.27 due to inorganic phosphate or due to slow hydrolysis to the monophosphate 13a.

Unsaturated and Oxygenated Derivatives

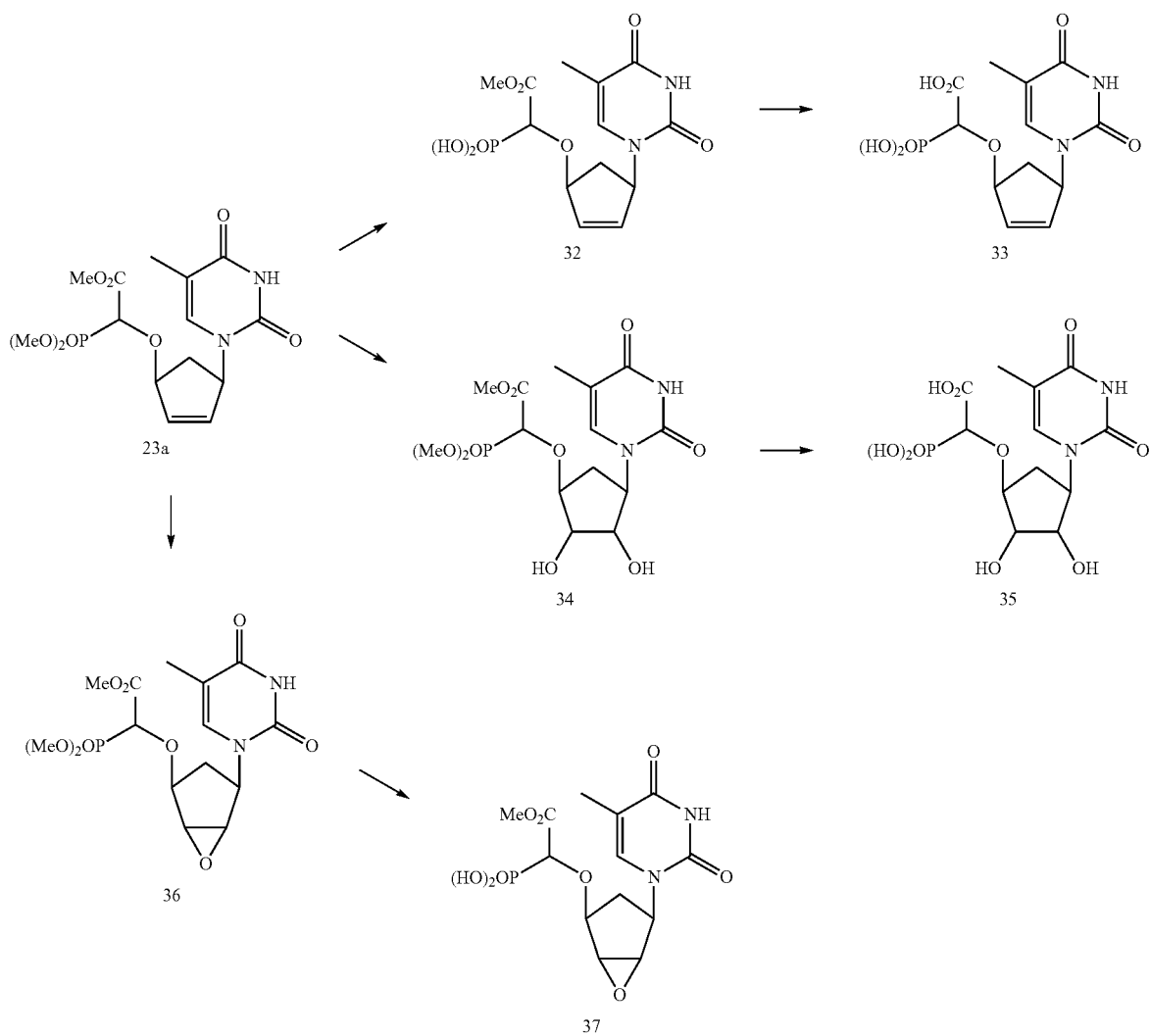

cis-1-{4'-[(Methoxycarbonyl)phosphonomethoxy]cyclopent-2'-en-1'-yl}thymine 32 cis-1-{4'-[Dimethyl(methoxycarbonyl)phosphonomethoxy]cyclopent-2'-en-1'-yl}thymine 23a (0.23 g, 0.6 mmol) was placed in a 10 mL microwave tube together with acetonitrile (3 mL), 2,6-lutidine (284 µL, 0.26 g, 2.4 mmol) and TMSBr (325 µL, 0.38 g, 2.4 mmol) and the mixture was irradiated at 50° C. for 10 minutes. Thereafter, the reaction was quenched by the addition of MeOH—H$_2$O (95:5) and the mixture concentrated under reduced pressure. After acidification, the residue was purified by charcoal chromatography to provide an amber glass (0.21 g) which was crystallised from methanol/ether to afford the desired product as a cream solid (0.17 g, 78%). δ$_H$ (400 MHz, CDCl$_3$)

cis-1-{4'-[(Carboxyl)phosphonomethoxy]cyclopent-2'-en-1'-yl}thymine 33

Lithium hydroxide (63 mg, 2.6 mmol) was added to a solution of cis-1-{4'-[(methoxycarbonyl)phosphonomethoxy]cyclopent-2'-en-1'-yl}thymine (113 mg, 0.3 mmol) in water (2.5 mL) and the solution stirred at 60° C. for 4.25 h. After concentration under reduced pressure the residue was acidified and purified by charcoal chromatography to afford the desired product as a white solid (84 mg, 78%). δ$_H$ (400 MHz, CDCl$_3$)

cis-1-{4'-[Dimethyl(methoxycarbonyl)phosphonomethoxy]-2',3'-dihydroxycyclopentan-1'-yl}thymine 34 cis-1-{4'-[Dimethyl(methoxycarbonyl)phosphonomethoxy]cyclopent-2'-en-1'-yl}thymine (45 mg, 0.12 mmol) was suspended in THF (3 mL) and 4% aq osmium tetroxide (810 µL, 810 mg, 0.13 mmol) was added. The resulting solution was stirred for 24 hours then quenched with 5% Na$_2$S$_2$O$_5$, concentrated under reduced pressure and purified by flash chromatography (10% MeOH/CH$_2$Cl$_2$) to afford the desired product as a white solid (26 mg, 53%). δ$_H$ (400 MHz, CDCl$_3$)

cis-1-{4'-[(Carboxyl)phosphonomethoxy]-2',3'-dihydroxycyclopentan-1'-yl}thymine 35

A 10 mL microwave tube was charged with cis-1-{4'-[dimethyl(methoxycarbonyl)phosphonomethoxy]-2',3'-dihydroxycyclopentan-1'-yl}thymine (23 mg, 0.05 mmol), TMSBr (28 μL, 32 mg, 2.3 mmol) and acetonitrile (2 mL) and the mixture was irradiated at 50° C. for 10 minutes. Thereafter, the reaction was quenched with MeOH—H$_2$O (95:5) and the mixture concentrated under reduced pressure. The residue was dissolved in water (2 mL), lithium hydroxide (7 mg, 3 mmol) was added and the solution was stirred at 60° C. for 3.5 hours. After concentration under reduced pressure and acidification, the residue was purified by charcoal chromatography to afford the desired product as a white solid (mg, %). $\delta_H$ (400 MHz, CDCl$_3$)

cis-1-{4'-[Dimethyl(methoxycarbonyl)phosphonomethoxy]-2',3'-epoxycyclopent-2'-en-1'-yl}thymine 36 cis-1-{4'-[Dimethyl(methoxycarbonyl)phosphonomethoxy]cyclopent-2'-en-1'-yl}thymine (39 mg, 0.1 mmol) was dissolved in methanol (3 mL) then benzonitrile (258 μL, 258 mg, 2.5 mmol) and potassium carbonate (14 mg, 0.1 mmol) were added followed by 30% aq hydrogen peroxide (256 μL, 285 mg, 0.1 mmol), dropwise over 10 minutes. Thereafter, the reaction mixture was stirred for 3 hours, quenched with water and extracted with dichloromethane (3×30 mL). The combined organic extracts were dried over MgSO4 and concentrated and the residue was purified by flash chromatography (5% MeOH/CH$_2$Cl$_2$) to afford the desired epoxide as a white solid (10 mg, 25%). $\delta_H$ (400 MHz, CDCl$_3$)

cis-1-{4'-[(Methoxycarbonyl)phosphonomethoxy]-2',3'-epoxycyclopent-2'-en-1'-yl}thymine 37 cis-1-{4'-[Dimethyl(methoxycarbonyl)phosphonomethoxy]-2',3'-epoxycyclopent-2'-en-1'-yl}thymine (6 mg, 0.015 mmol) was placed in a 10 mL microwave tube together with acetonitrile (1 mL), 2,6-lutidine (7 μL, 6 mg, 0.06 mmol) and TMSBr (8 μL, 9 mg, 0.06 mmol) and the mixture was irradiated at 50° C. for 10 minutes. Thereafter, the reaction was quenched by the addition of CH$_3$OH—H$_2$O (95:5) and the mixture concentrated under reduced pressure. The residue was purified by charcoal chromatography to provide the desired compound (4 mg, 69%); $\delta_H$ (400.1 MHz, D$_2$O) 1.37-1.50 (1H, m), 1.82-1.92 (3H, m), 2.24-2.45 (1H, m), 3.72-3.88 (5H, m), 4.16-4.30 (1H, m), 4.38-4.51 (1H, m), 4.81-4.96 (1H, m), 7.69-7.74 (1H, m); m/z (ES−) 375.2 [M−H]; HRMS (ES+) Exact mass calculated for C$_{13}$H$_{18}$N$_2$O$_9$P [M+H]$^+$ 377.0750; found 377.0741.

Fluorouracil Derivatives

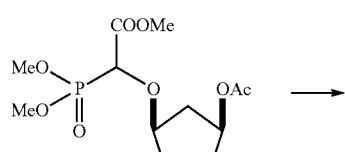

20

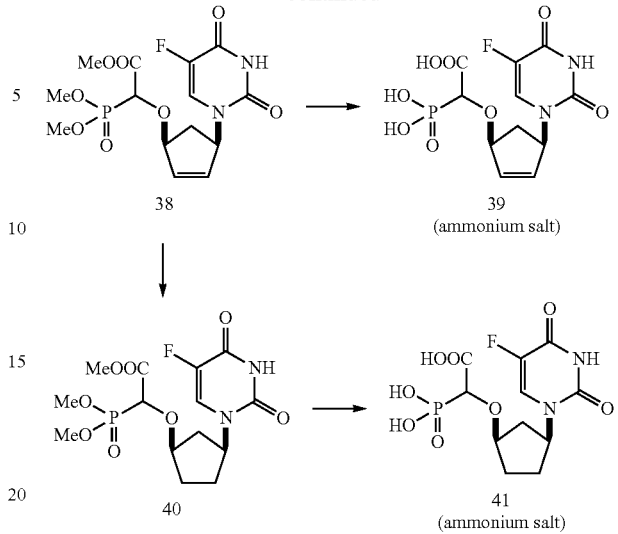

methyl 2-(dimethoxyphosphoryl)-2-((4-(5-fluoro-2, 4-dioxo-3,4-dihydropyrimidin-1(2H)-yl)cyclopent-2-en-1-yl)oxy)acetate 38

Aqueous sodium carbonate (2M, 0.35 mL, 0.7 mmol) was added to a suspension of 5-fluorouracil (113 mg, 0.87 mmol) in acetonitrile (10 mL). The suspension was stirred for 10 min under a nitrogen atmosphere prior to the addition of the allylic acetate 20 (186 mg, 0.58 mmol) in acetonitrile (5 mL). Nitrogen was bubbled through the reaction mixture for 15 min and tetrakis(triphenylphosphine)palladium (0) (54 mg, 0,046 mmol) was added. The reaction mixture was stirred at 60° C. for 2 h 30 under a nitrogen atmosphere. The mixture was allowed to cool to room temperature prior to the addition of dichloromethane (20 mL). The resulting precipitate was removed via filtration and the solution was concentrated in vacuo. Purification via flash chromatography (SiO$_2$, 3% methanol in dichloromethane) afforded the pure product as a beige solid (94 mg, 0.24 mmol, 41%, 1:1, d.r.). Rf (DCM/MeOH 92/8): 0.61; m.p. 1410° C.; μmax/cm$^{-1}$ (film): 3486, 3171 (NH), 3066 (CH), 2961 (CH), 1750, 1713 (C=O), 1665, 1467, 1438, 1389, 1260 (P=O), 1104 (C=N), 1033 (C—O); $\delta_H$ (300 MHz, CDCl$_3$): 1.80-1.87 (1H, m), 2.67-2.80 (1H, m), 3.81-3.87 (9H, m), 4.51 (0.5H, d, J=20.0), 4.53 (0.5H, d, J=19.3), 4.58-4.60 (0.5H, m), 4.66-4.67 (0.5H, m), 5.65-5.71 (1H, m)], 5.94-6.00 (1H, m), 6.30-6.37 (1H, m), 7.64 (0.5H, d, J=6.8z), 7.66 (0.5H, d, J=6.6 Hz), 9.93 [1H, br s]; $\delta_C$ (75.5 MHz, CDCl$_3$): 36.6, 36.9, 53.2, 54.18, 54.26, 54.31, 54.35, 58.69, 58.74, 74.8 (d, J=159.7), 84.3 (d, J=9.6), 84.6 (d, J=11.5), 125.9 (d, J=33.5), 126.0 (d, J=33.4), 134.4, 134.7, 136.2, 136.7, 140.9 (d, J=237.7), 149.8, 157.1 [d, J=26.5), 167.6 (d, J=2.5), 167.8 (d, J=2.4 Hz); $\delta_P$ (121.5 MHz, CDCl$_3$): 16.26, 16.45; $\delta_F$ (282.4 MHz, CDCl$_3$): −164.23, −164.16; HRMS (ES+): Exact mass calculated for C$_{14}$H$_{19}$FN$_2$O$_8$P [M+H]$^+$ 393.0863. Found: 393.0858. MS (ES$^-$): [M−H]$^-$ 391.2 (46%), 244.3 (60%), 129.3 (92%), 45.2 (100%).

2-((4-(5-fluoro-2,4-dioxo-3,4-dihydropyrimidin-1 (2H)-yl)cyclopent-2-en-1-yl)oxy)-2-phosphonoacetic acid 39

Bromotrimethylsilane (147 mg, 124 μL, 0.960 mmol) and 2,6-lutidine (103 mg, 112 μL, 0.960 mmol) were added via syringe to a solution of phosphonate ester 38 (94 mg, 0.240 mmol) in acetonitrile (3 mL). The solution was heated at 50° C. for 10 minutes under microwave irradiation. Water (300 µL) and methanol (300 µL) were added and the mixture was stirred 20 minutes at room temperature. The reaction mixture was then concentrated in vacuo and the residue was dissolved in a solution of lithium hydroxide (57 mg, 2.40 mmol) in water (5 mL). The mixture was heated for 1 h at 50° C. before concentration in vacuo. The crude material was purified by charcoal chromatography and the fraction containing the phosphonate were concentrated to afford the fully deprotected phosphonate 39 as its ammonium salt (71 mg, 0.193 mmol, 81%, 1:1 d.r.). $\delta_H$ (300 MHz, D$_2$O): 1.74-1.82 (1H, m), 2.87-2.97 (1H, m), 4.14 (0.50H, d, J=18.5), 4.17 (0.5H, d, J=17.9), 4.66-4.78 (1H, m), 5.49-5.55 (1H, m), 5.96-6.00 (1H, m), 6.40 (0.5H, d, J=5.6), 6.46 (0.5H, d, J=5.5), 7.98 (0.5H, d, J=6.5), 7.99 (0.5H, d, J=6.4); $\delta_C$ (75.5 MHz, D$_2$O): 36.2, 36.5, 59.76, 59.85, 78.6 (d, J=133.6), 83.2 (d, J=13.2), 128.1 (d, J=33.5), 128.2 (d, J=33.4), 132.0, 132.1, 137.3, 137.8, 140.9 (d, J=232.2), 150.9, 159.8 (d, J=25.4), 176.9; $\delta_P$ (121.5 MHz, D$_2$O): 12.08, 12.31; $\delta_F$ (282.4 MHz, D$_2$O): −166.20, −166.16; HRMS (ES+): Exact mass calculated for C$_{11}$H$_{13}$FN$_2$O$_8$P [M+H]$^+$ 351.0394. Found: 351.0407.

methyl 2-(dimethoxyphosphoryl)-2-((3-(5-fluoro-2,4-dioxo-3,4-dihydropyrimidin-1(2H)-yl)cyclopentyl)oxy)acetate 40

Palladium (5% on carbon, 30 mg) was added to a solution of compound 38 (61 mg, 0.155 mmol) in methanol (5 mL). The mixture was stirred for 16 h under hydrogen atmosphere and filtrated over Celite®. Celite® was washed with methanol (3×5 mL) and the filtrate was concentrated in vacuo. Purification by flash chromatography (SiO$_2$, 3% methanol in dichloromethane) yielded the saturated compound as a white gum (59 mg, 0.150 mmol, 97%, 1:1 d.r.). Rf (DCM/MeOH 92/8): 0.57; $v_{max}$/cm$^{-1}$ (film): 3490, 3174 (NH), 3067, 2961, 2857, 2825 (CH), 1749, 1700 (C=O), 1469, 1438, 1394, 1359, 1319 (C—H), 1265, 1109, 1032 (C—O, C—N, P—O); $\delta_H$ (300 MHz, CDCl$_3$): 1.47-2.42 (6H, m), 3.82-3.87 (9H, m), 4.15-4.17 (0.5H, m), 4.21-4.23 (0.5H, m), 4.39 (0.5H, d, J=19.0), 4.45 (0.5H, d, J=20.3), 5.24-5.33 (1H, m), 8.06 (0.5H, d, J=6.7), 8.18 (0.5H, d, J=6.7), 9.34 (1H, m); $\delta_C$ (75.5 MHz, CDCl$_3$): 30.1, 30.2, 30.5, 31.4, 38.7, 39.0, 53.1, 53.4, 53.9, 54.0, 54.2, 54.3, 73.1 (d, J=160.5), 74.1 (d, J=159.3), 81.9 (d, J=11.4), 83.0 (d, J=8.6), 126.8 (d, J=34.3), 140.9 (d, J=236.2), 141.0 (d, J=236.1), 150.1, 156.9 (d, J=26.6), 167.5 (d, J=2.0), 167.9 (d, JPC=2.9); $\delta_P$ (121.5 MHz, CDCl$_3$): 16.64, 16.92; $\delta_F$ (282.4 MHz, CDCl$_3$): −164.08, −164.06; HRMS (ES$^+$): Exact mass calculated for C$_{14}$H$_{21}$FN$_2$O$_8$P [M+H]$^+$ 395.1020. Found: 395.1013. MS (ES$^-$): [M−H]$^-$ 394.3 (92%), 379.2 (100%).

2-((3-(5-fluoro-2,4-dioxo-3,4-dihydropyrimidin-1(2H)-yl)cyclopentyl)oxy)-2-phosphonoacetic acid 41

Bromotrimethylsilane (79 mg, 67 µL, 0.517 mmol) was added via syringe to a solution of phosphonate ester 40 (51 mg, 0.129 mmol) in acetonitrile (3 mL). The solution was heated at 50° C. for 10 minutes under microwave irradiation. Water (100 µL) and methanol (100 µL) were added and the mixture was stirred 20 minutes at room temperature. The reaction mixture was then concentrated in vacuo and the residue was dissolved in a solution of lithium hydroxide (31 mg, 1.29 mmol) in water (3 mL). The mixture was heated for 2 h at 50° C. before concentration in vacuo. The crude material was purified by charcoal chromatography and the fraction containing the phosphonate were concentrated to afford the fully deprotected phosphonate 41 containing ≈ 40% of D-exchange product as its ammonium salt (25 mg, 0.068 mmol, 52%, 1:1 d.r.). m.p.: 243° C.; $\delta_H$ (300 MHz, D$_2$O): 1.69-2.17 (5H, m), 2.40-2.51 (1H, m), 3.99-4.14 (2H, m), 4.93-5.01 (1H, m), 8.33 (0.3H, d, J=8.4 Hz, possible D-exchange), 8.35 (0.3H, d, J=8.8 Hz, possible D-exchange); $\delta_P$ (121.5 MHz, D$_2$O): 12.09, 12.32; $\delta_F$ (282.4 MHz, D$_2$O): −165.89, −165.86, −165.60 (possible D-exchange compound), −165.57 (possible D-exchange compound); HRMS (ES$^+$): Exact mass calculated for C$_{11}$H$_{15}$FN$_2$O$_8$P [M+H]$^+$ 353.0550. Found: 353.0535. Exact mass calculated for C$_{11}$H$_{14}$DFN$_2$O$_8$P [M+H]$^+$ 354.0613. Found: 354.0597.

Prodrug Compounds:

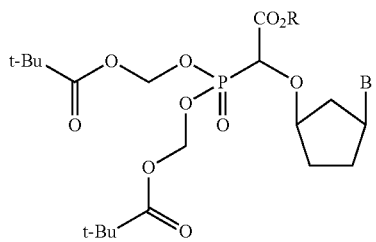

42 R = Me B = T
43 R = POM B = T
44 R = H B = T
45 R = Me B = FU

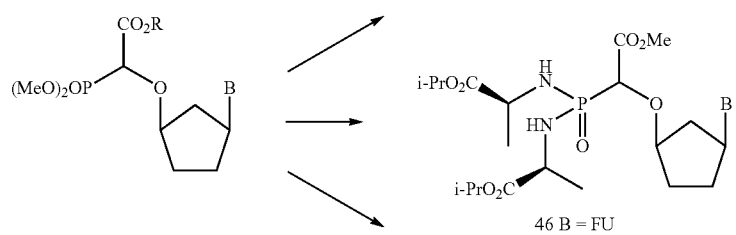

46 B = FU

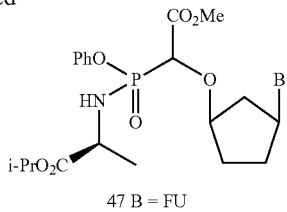

47 B = FU

(((2-methoxy-1-((3-(5-methyl-2,4-dioxo-3,4-dihydropyrimidin-1(2H)-yl)cyclopentyl)oxy)-2-oxoethyl)phosphoryl)bis(oxy))bis(methylene)bis(2,2-dimethylpropanoate) 42

A 10 mL microwave tube was charged with cis-1-{4'-[dimethyl(methoxycarbonyl)phosphonomethoxy]cyclopentan-1'-yl}thymine (0.23 g, 0.6 mmol), TMSBr (306 µL, 0.35 g, 2.3 mmol) and acetonitrile (3 mL) and the mixture was irradiated at 50° C. for 10 minutes. Thereafter, the reaction was quenched with MeOH—H$_2$O (95:5) and the mixture concentrated under reduced pressure. The resultant amber oil was dissolved in THF (15 mL), Hunig's base (556 µL, 0.42 g, 3.2 mmol) was added followed by POM iodide (0.45 g, 1.85 mmol) and the reaction mixture was stirred overnight. After removal of suspended solids by filtration and concentration of the filtrate under reduced pressure, the residue was purified by flash chromatography (5% MeOH/CH$_2$Cl$_2$) to afford the desired product as an oil (0.32 g, 94%). $\delta_H$ (600 MHz, CDCl$_3$): 1.22-1.23 (18H, m), 1.57-1.62 (1H, m), 1.77-1.88 (3H, m), 1.98-1.99 (3H, s), 2.16-2.20 (1H, m), 2.36-2.41 (1H, m), 3.82 (3H, s), 4.20-4.22 (0.5H, m), 4.26-4.28 (0.5H, m), 4.44-4.46 (0.5H, d, $J_{PH}$=18), 4.48-4.50 (0.5H, d, $J_{PH}$=18.6 Hz), 5.22-5.24 (1H, m), 5.65-5.78 (4H, m), 7.64 (0.5H, br), 7.74 (0.5H, br), 7.80 (1H, br s); $\delta_C$ (150.9 MHz, CDCl$_3$): 12.30, 26.81-26.92, 29.70, 29.98, 30.03, 30.76, 31.17, 38.74, 38.31, 38.44, 53.07, 53.11, 53.21, 73.24 [d, $J_{PC}$=164), 74.33 [d, $J_{PC}$=163), 82.08, 82.12-82.81, 111.71, 111.78, 138.02 138.22, 150.15, 151.19, 166.58, 166.62, 166.58, 166.62, 166.8, 166.99, 176.70, 176.88; $\delta_P$ (121.5 MHz, CDCl$_3$): 13.79, 13.87; HRMS (ES+): Exact mass calculated for C$_{25}$H$_{40}$N$_2$O$_{12}$P [M+H]$^+$ 591.2319. Found: 591.2319.

(((1-((3-(5-methyl-2,4-dioxo-3,4-di hydropyrimidin-1(2H)-yl)cyclopentyl)oxy)-2-oxo-2-((pivaloyloxy)methoxy)ethyl)phosphoryl)bis(oxy))bis(methylene)bis(2,2-dimethylpropanoate) 43

Bromotrimethylsilane (100 µL, 0.78 mmol) was added via syringe to a solution of the trimethyl phosphonate ester, methyl 2-(dimethoxyphosphoryl)-2-(((1R,3S)-3-(5-methyl-2,4-dioxo-3,4-dihydropyrimidin-1(2H)-yl)cyclopentyl)oxy)acetate (58 mg, 0.149 mmol) in acetonitrile (2 mL). The solution was heated at 50° C. for 10 min under microwave irradiation at 50 W. Upon cooling, water (50 µL) and methanol (950 µL) were added and the mixture was stirred for 30 minutes at room temperature. The reaction mixture was concentrated in vacuo and the residue was dissolved in dry acetonitrile (5 mL). A solution of DIPEA (110 µL, 1.15 mmol) in acetonitrile (1 mL) and a solution of POM-iodide (120 mg, 0.50 mmol) in acetonitrile (1 mL) were added and the mixture stirred overnight at room temperature. The reaction mixture was concentrated in vacuo and purified by flash chromatography (SiO$_2$, 5% methanol in dichloromethane) to give the tris-pivaloyloxymethyl prodrug as a yellow gum (14 mg, 14%). $\delta_H$ (300 MHz, CDCl$_3$): 1.21-1.23 (27H, m), 1.76-2.40 (6H, m), 1.98-1.99 (3H, s), 4.17-4.26 (1H, m), 4.42-4.54 (1H, m), 5.17-5.26 (1H, m), 5.63-5.88 (6H, m), 7.57-7.62 (1H, m), 8.26 (1H, br s); HRMS (ES+): Exact mass calculated for C$_{30}$H$_{47}$N$_2$NaO$_{14}$P [M+Na]$^+$713.2663. Found: 713.2652.

(((1-((3-(5-fluoro-2,4-dioxo-3,4-dihydropyrimidin-1(2H)-yl)cyclopentyl)oxy)-2-methoxy-2-oxoethyl)phosphoryl)bis(oxy))bis(methylene)bis(2,2-dimethylpropanoate) 45

Bromotrimethylsilane (126 mg, 106 µL, 0.820 mmol) was added via syringe to a solution of phosphonate ester 40 (81 mg, 0.205 mmol) in acetonitrile (3 mL). The solution was heated at 50° C. for 10 minutes under microwave irradiation. Water (200 µL) and methanol (200 µL) were added and the mixture was stirred 20 minutes at room temperature. The reaction mixture was then concentrated in vacuo and the residue was dissolved in dry acetonitrile (13 mL). A solution of DIPEA (146 mg, 196 µL, 1.127 mmol) in acetonitrile (2.6 mL) and a solution of POM-iodide (154 mg, 0.636 mmol) in acetonitrile (2.6 mL) were added and the mixture was stirred overnight at room temperature. The reaction mixture was then concentrated in vacuo. Purification by flash chromatography (SiO$_2$, 2% methanol in dichloromethane) yielded the bis-POM prodrug as a colorless gum 45 (38 mg, 0.064 mmol, 31%, 1:1 d.r.). $v_{max}$/cm$^{-1}$ (film): 3500, 3185 (NH), 3071, 2978, 2876, (CH), 1757, 1701 (C═O), 1482, 1464, 1436, 1438, 1397, 1367 (C—H), 1267, 1230, 1137, 1057, 1024, 1004, (P—O, C—O); Rf (DCM/MeOH 92/8): 0.59; 6H (300 MHz, CDCl$_3$): 1.22-1.23 (18H, m), 1.49-2.43 (6H, m), 3.81 (3H, s), 4.19-4.22 (0.5H, m), 4.29-4.31 (0.5H, m), 4.46 (0.5H, d, J=19.2), 4.49 (0.5H, d, J=20.6), 5.22-5.32 (1H, m), 5.62-5.81 (4H, m), 8.05 (0.5H, d, J=6.6) 8.18 (0.5H, d, J=6.6), 9.21 (1H, m); $\delta_C$ (75.5 MHz, CDCl$_3$): 26.9, 30.1, 30.8, 31.0, 31.2, 38.7, 38.86, 38.90, 53.21, 53.23, 54.14, 54.21, 73.6 (d, J=164.8), 74.1 (d, J=162.9), 82.3, 82.4, 82.5, 82.6, 82.9 (d, J=7.6), 126.9 (d, J=37.9), 141.0 (d, J=231.1), 150.1, 156.9 (d, J=26.6), 166.8 (d, J=2.4), 167.0 (d, J=3.1), 176.8, 177.0; $\delta_P$ (121.5 MHz, CDCl$_3$): 13.60, 13.80; $\delta_F$ (282.4 MHz, CDCl$_3$): −163.88, −163.72; HRMS (ES$^+$): Exact mass calculated for C$_{24}$H$_{37}$FN$_2$O$_{12}$P [M+H]$^+$ 595.2068. Found: 595.2068.

Diisopropyl 2,2'-(((1-(((1R,3S)-3-(5-fluoro-2,4-dioxo-3,4-dihydropyrimidin-1(2H)-yl)cyclopentyl)oxy)-2-methoxy-2-oxoethyl)phosphoryl)bis(azanediyl))dipropanoate 46

Bromotrimethylsilane (70 µL, 0.50 mmol) was added via syringe to a solution of phosphonate ester, methyl 2-(dimethoxyphosphoryl)-2-(((1R,3S)-3-(5-fluoro-2,4-dioxo-3,4-dihydropyrimidin-1(2H)-yl)cyclopentyl)oxy)acetate (50 mg, 0.126 mmol) in acetonitrile (2 mL). The solution was heated at 50° C. for 10 minutes under microwave irradiation at 50 W. The solution was cooled to room temperature and concentrated to dryness in vacuo and the residue dissolved in pyridine (1 mL). Triethylamine (0.25 ml, 1.79 mmol) and L-alanine isopropyl ester hydrochloride (84 mg, 0.5 mmol) were added and the mixture heated to 60° C. until a clear solution was obtained (typically 5 min). A freshly prepared solution of aldrithiol-2 (166 mg, 0.756 mmol) and triphenylphosphine (198 mg, 0.756 mmol) in pyridine (1 mL) was added to the above reaction mixture. The reaction was stirred at 60° C. overnight, cooled to room temperature and concentrated under vacuum. The residue was dissolved in ethyl acetate (25 mL) and washed with saturated sodium bicarbonate solution (4×25 mL), dried (MgSO$_4$), filtered and concentrated in vacuo. Purification of the residue by flash chromatography (SiO$_2$, 5% methanol in dichloromethane) afforded the bisamidate prodrug as a clear gum (11 mg, 15%). $\delta_H$ (600 MHz, CDCl$_3$): 1.12-1.42 (12H, m), 1.56-2.48 (6H, m), 3.48-3.61 (2H, m), 3.82-3.84 (3H, m), 3.99-4.08 (2H, m), 4.18-4.19 (0.4H, m), 4.33-4.36 (0.6H, m), 4.39-4.52 (1H, m), 4.96-5.03 (2H, m), 5.22-5.23 (1H, br), 8.09-8.12 (0.4H, m), 8.24-8.29 (0.6H, m), 8.83 (1H, br s); $\delta_P$ (121.5 MHz, CDCl3): 16.37; HRMS (ES+): Exact mass calculated for C$_{24}$H$_{39}$FN$_4$O$_{10}$P [M+H]$^+$ 593.2388. Found: 593.2404.

Isopropyl 2-(((1-(((1R,3S)-3-(5-fluoro-2,4-dioxo-3, 4-dihydropyrimidin-1(2H)-yl)cyclopentyl)oxy)-2-methoxy-2-oxoethyl)(phenoxy)phosphoryl)amino) propanoate 47

Bromotrimethylsilane (60 µL, 0.43 mmol) was added via syringe to a solution of phosphonate ester, methyl 2-(dimethoxyphosphoryl)-2-(((1R,3S)-3-(5-fluoro-2,4-dioxo-3,4-dihydropyrimidin-1(2H)-yl)cyclopentyl)oxy)acetate (45 mg, 0.113 mmol) in acetonitrile (2 mL). The solution was heated at 50° C. for 10 minutes under microwave irradiation at 50 W. The solution was cooled to room temperature and concentrated to dryness in vacuo and the residue dissolved in pyridine (1 mL). Triethylamine (0.20 ml, 1.43 mmol) and L-alanine isopropyl ester hydrochloride (34 mg, 0.20 mmol) and phenol (47 mg, 0.50 mmol) were added and the mixture heated to 60° C. until a clear solution was obtained (typically 5 min). A freshly prepared solution of Aldrithiol-2 (130 mg, 0.590 mmol) and triphenylphosphine (150 mg, 0.573 mmol) in pyridine (1 mL) was added to the above reaction mixture. The reaction was stirred at 60° C. overnight, cooled to room temperature and concentrated under vacuum. The residue was dissolved in ethyl acetate (25 mL) and washed with saturated sodium bicarbonate solution (4×25 mL), dried (MgSO$_4$), filtered and concentrated in vacuo. Purification of the residue by flash chromatography (SiO$_2$, 5% methanol in dichloromethane) afforded the phenoxyamidate prodrug as a brown gum (15 mg, 24%). $\delta_H$ (300 MHz, CDCl$_3$): 1.17-2.42 (6H, m), 1.17-1.20 (6H, m), 1.33-1.40 (3H, m), 3.81-3.90 (3H, m), 4.09-4.18 (1H, m), 4.25-4.33 (1H, m), 4.46-4.58 (1H, m), 4.90-5.02 (1H, m), 5.17-5.28 (1H, m), 7.16-7.35 (5H, m), 8.05-8.15 (1H, m); $\delta_P$ (121.5 MHz, CDCl$_3$): 14.95, 15.21, 15.64; HRMS (ES+): Exact mass calculated for C$_{24}$H$_{32}$N$_3$FO$_9$P [M+H]$^+$ 556.1860. Found: 556.1864.

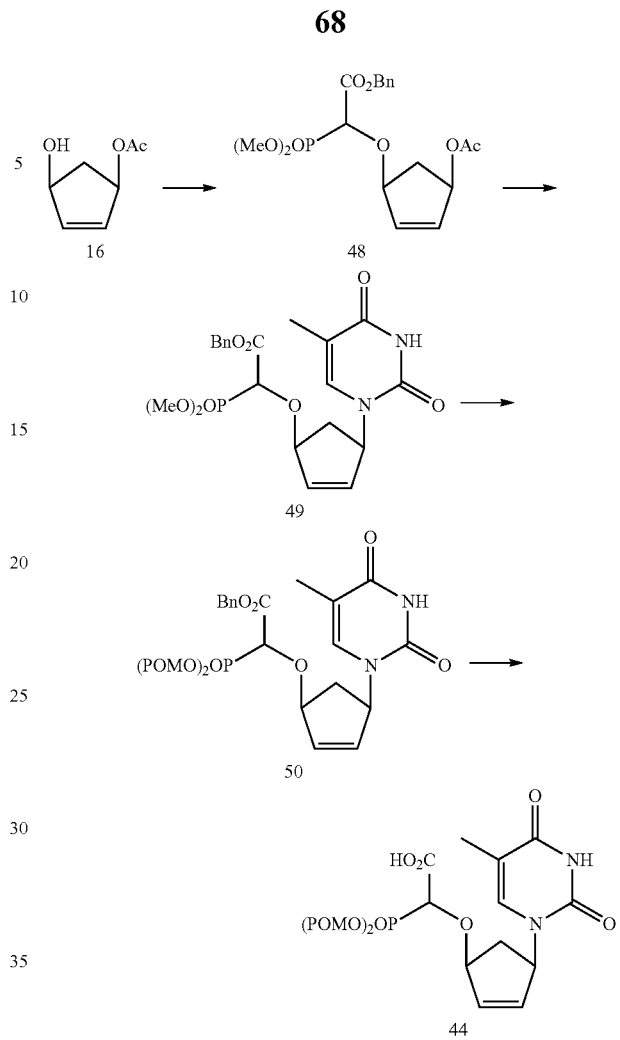

Benzyl(dimethylphosphono)diazoacetate

A solution of benzyl(dimethylphosphono)acetate (2.01 g, 7.78 mmol) and dodecylbenzenesulfonyl azide (2.73 g, 7.78 mmol) in acetonitrile (25 mL) was treated with triethylamine (1.1 mL, 0.79 g, 7.78 mmol) and stirred at room temperature overnight and then at 40° C. for 2 h. Silica gel (ca. 10 g) was added and the volatiles were removed under reduced pressure. The residue was purified by flash chromatography (60% EtOAc/hexanes) to afford the desired product as a yellow oil (1.3 g, 59%). $\delta_H$ (400 MHz, CDCl$_3$) 3.81 (6H, d, J=11.8), 5.25 (2H, s), 7.32-7.40 (5H, m).

Benzyl 2-(((1S,4R)-4-acetoxycyclopent-2-en-1-yl) oxy)-2-(dimethoxyphosphoryl)acetate 48

A mixture of 4-hydroxycyclopent-2-en-1-yl acetate (0.49 g, 3.45 mmol) and benzyl(dimethoxyphosphono)diazoacetate (1.08 g, 3.77 mmol) was dissolved in benzene (20 mL) and purged under nitrogen. Molecular sieves (4 Å) were added and the mixture stirred for 2 min. Rhodium acetate (15 mg) was added and the reaction heated to reflux for 24 h. The reaction mixture was cooled to room temperature, filtered and the solvent removed to afford a green residue which was purified by chromatography (SiO$_2$, 20% ethyl acetate/hexane) to give the desired product 48 as a clear oil (0.21 g, 15%). $\delta_H$ (300 MHz, CDCl$_3$): 1.68-1.88 (1H, m), 2.00 (3H, s), 2.67-2.78 (1H, m), 3.72-3.84 (6H, m), 4.40-4.83 (2H, m, overlapping signals), 5.19-5.34 (2H, m), 5.43-5.49 (1H, m), 6.02-6.11 (2H, m), 7.31-7.39 (5H, m).

Benzyl 2-(dimethoxyphosphoryl)-2-(((1S,4R)-4-(5-methyl-2,4-dioxo-3,4-dihydropyrimidin-1(2H)-yl) cyclopent-2-en-1-yl)oxy)acetate 49

Thymine (100 mg, 0.79 mmol) was added to a degassed solution of benzyl 2-((4-acetoxycyclopent-2-en-1-yl)oxy)-2-(dimethoxyphosphorypacetate 48 (200 mg, 0.52 mmol) and 2M Na2CO3 solution (0.28 mL, 0.57 mmol) in acetonitrile (3 mL). The suspension was degassed for a further 5 min and Pd(PPh$_3$)$_4$ (60 mg, 5 mol %) was added. The resulting suspension was heated at 50° C. under microwave irradiation at 50 W for 2 h. The reaction mixture was cooled to room temperature, gravity filtered and concentrated under vacuum to give a purple residue which was purified by chromatography to afford the title compound 49 as a brown oil (50 mg, 21%). $\delta_H$ (300 MHz, CDCl$_3$): 1.72-1.77 (1H, m), 1.92 (3H, s), 2.68-2.83 (1H, m), 3.71-3.81 (6H, m), 4.46-4.66 (2H, m, overlapping signals), 5.12-5.34 (2H, m), 5.60-5.69 (1H, m), 5.88-5.96 (1H, m), 6.20-6.31 (1H, m), 7.33-7.42 (6H, m, overlapping signals), 8.24 (1H, bs).

(((2-(Benzyloxy)-1-(((1S,4R)-4-(5-methyl-2,4-dioxo-3,4-dihydropyrimidin-1(2H)-yl)cyclopent-2-en-1-yl)oxy)-2-oxoethyl)phosphoryl)bis(oxy))bis(methylene)bis(2,2-di methyl propanoate) 50

Bromotrimethylsilane (56 µL, 0.44 mmol) and lutidine (50 µL, 0.44 mmol) were sequentially added via syringe to a solution of benzyl-2-(dimethoxyphosphoryl)-2-((4-(5-methyl-2,4-dioxo-3,4-dihydropyrimidin-1(2H)-yl)cyclopent-2-en-1-yl)oxy)acetate 49 (50 mg, 0.11 mmol) in acetonitrile (2 mL). The solution was heated at 50° C. for 10 min under microwave irradiation at 50 W. Upon cooling, water (50 µL) and methanol (950 µL) were added and the mixture was stirred for 10 minutes at room temperature. The reaction mixture was concentrated in vacuo and the residue was dissolved in dry THF (5 mL). A solution of DIPEA (100 µL, 1.05 mmol) in THF (1 mL) and a solution of POM-iodide (145 mg, 0.60 mmol) in THF (1 mL) were added and the mixture stirred overnight at room temperature. The reaction mixture was concentrated in vacuo and purified by flash chromatography (SiO$_2$, 5% methanol in dichloromethane) to give the bis-pivaloyloxymethyl product as a yellow gum containing some impurities. This gum was further purified by dissolving in dichloromethane (2 mL) and washing with 1M HCl solution (2×5 mL), and brine (2×5 mL). The organic layer was dried (MgSO4), filtered and concentrated to give the desired product 50 as a yellow gum (10 mg, 14%). $\delta_H$ (300 MHz, CDCl$_3$): 1.21-1.29 (18H, s), 1.72-1.77 (1H, m), 1.90 (3H, s), 2.69-2.83 (1H, m), 4.50-4.71 (2H, m, overlapping signals), 5.17-5.32 (1H, m), 5.54-5.74 (5H, m, overlapping signals), 5.89-5.94 (1H, m), 6.18-6.32 (1H, m), 7.33-7.40 (5H, m), 7.65-7.72 (1H, m); $\delta_P$ (121.5 MHz, CDCl$_3$): 13.13, 13.35.

2-(bis((Pivaloyloxy)methoxy)phosphoryl)-2-(((1R, 3S)-3-(5-methyl-2,4-dioxo-3,4-dihydropyrimidin-1 (2H)-yl)cyclopentyl)oxy)acetic acid 44

(((2-(Benzyloxy)-1-((4-(5-methyl-2,4-dioxo-3,4-dihydropyrimidin-1(2H)-yl)cyclopent-2-en-1-yl)oxy)-2-oxoethyl) phosphoryl)bis(oxy))bis(methylene)bis(2,2-dimethylpropanoate) 50 (10 mg, 0.015 mmol) was dissolved in methanol (5 mL) and flushed with nitrogen. Palladium on carbon 5% (10 mg) was added and the suspension stirred under a hydrogen filled balloon at room temperature for 24 h. Analysis of the crude mixture by NMR indicated the presence of both product and starting material. A second portion of palladium on carbon 5% (20 mg) was added and the suspension stirred under a hydrogen filled balloon at room temperature for a further 24 h. The reaction mixture was filtered through a pad of Celite®, and concentrated to give the product 44 as a colorless gum (5 mg, 58%). $\delta_H$ (300 MHz, CDCl$_3$): 1.22-1.23 (18H, s), 1.52-1.62 (3H, m), 1.82 (3H, m), 2.12-2.38 (3H, m), 4.25-4.31 (1H, m), 4.44-4.53 (1H, m), 5.22-5.24 (1H, m), 5.52-5.77 (4H, m), 7.67 (0.5H, s), 7.87 (0.5H, s), 9.03 (1H, bs). $\delta_P$ (121.5 MHz, CDCl3): 14.34, 14.43; m/z (ES+): C$_{24}$H$_{38}$N$_2$O$_{12}$P [M+H]$^+$ 577; HRMS exact mass calculated for C$_{24}$H$_{38}$N$_2$O$_{12}$P, 577.2162; found 577.2164.

Six-Membered Ring Derivative

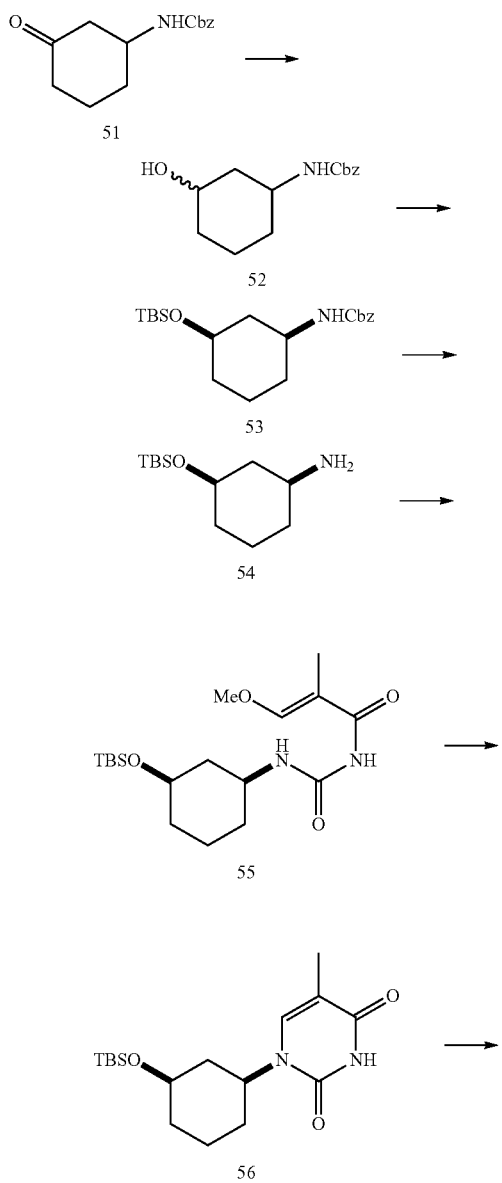

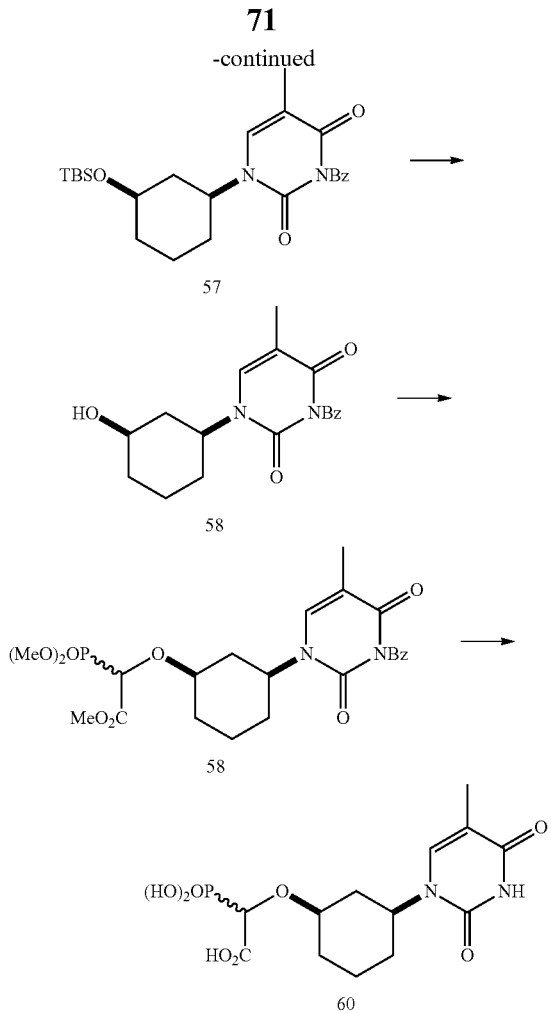

Benzyl(3-hydroxycyclohexyl)carbamate cis/trans mixture 52

A solution of benzyl(3-oxocyclohexyl)carbamate 51[60] (5.0 g, 20.2 mmol) in methanol (50 mL) was cooled in ice and treated with NaBH$_4$ (0.31 g, 8.1 mmol) in one portion. After stirring for 15 min the solution was evaporated under reduced pressure and then further evaporated from two more portions of methanol (25 mL each). The residue was partitioned with CH$_2$Cl$_2$ (50 mL) and 2 M HCl (50 mL), the phases were separated and the aqueous phase was extracted with CH$_2$Cl$_2$ (25 mL). The combined organic phases were washed with brine (50 mL), dried over MgSO$_4$ and concentrated to a slightly yellow solid (4.5 g, 90%), which was used in the next step without further purification. The $^1$H NMR spectrum was satisfactory for a ~7:3 mixture of cis and trans isomers. $\delta_H$ (400 MHz, CDCl$_3$) 1.2-2.2 (8H, m), 3.54-3.67 (0.7H, m), 3.70-3.79 (0.7H, m), 3.89-4.00 (0.3H, m), 4.01-4.06 (0.3H, m), 4.62-4.78 (0.3H, br s), 5.08, 5.10 (2.7H, two overlapping br s), 7.27-7.40 (5H, m).

cis-Benzyl(3-((tert-butyldimethylsilyl)oxy)cyclohexyl)carbamate 53

Solid TBSCl (2.66 g, 17.6 mmol) was added to a stirring mixture of benzyl(3-hydroxycyclohexyl)carbamate (4.0 g, 16 mmol) and imidazole (1.63 g, 24 mmol) in DMF (16 mL). After 3 h the mixture was partitioned with 2 M HCl (100 mL) and Et$_2$O (100 mL). The layers were separated and the aqueous phase was extracted with Et$_2$O (2×50 mL). The combined organic extracts were concentrated and purified by flash chromatography to afford the desired cis diastereomer 53 (2.99 g, 73% based on 7:3 dr in starting material). $\delta_H$ (400 mHz, CDCl$_3$) 0.06 (6H, s), 0.89 (9 h, s), 1.28-1.51 (4H, m), 1.60-1.71 (2H, m), 1.75-1.85 (1H, m), 1.86-1.93 (1H, m), 3.70-3.80 (1H, m), 3.83-3.92 (1H, m), 5.08 (2H, distorted ABq), 5.70 (1H, br s), 7.27-7.37 (5H, m); $\delta_C$ (150 mHz, CDCl$_3$) -5.0, -4.8, 18.0, 25.8, 31.4, 34.0, 39.4 br, 47.4, 66.2, 68.9, 127.8, 127.85, 155.5, 128.4, 136.9; m/z (ES+) 364.3 [M+H$^+$; HRMS (ES+) exact mass calculated for C$_{20}$H$_{34}$NO$_3$Si [M+H]$^+$, 364.2308; found 364.2301. The stereochemistry was confirmed by conversion of a sample to the known cis-benzyl(3-hydroxycyclohexyl)carbamate by TBAF deprotection: $\delta_H$ (400 MHz, CDCl$_3$) 1.10-1.39 (4H, m), 1.67-1.89 (3H, m), 2.20-2.29 (1H, m), 3.53-3.89 (1H, m), 3.69-3.81 (1H, m), 5.09 (3H, br s), 7.27-7.40 (5H, m).[61]

3-((tert-Butyldimethylsilyl)oxy)cyclohexylamine 54

A mixture of cis-benzyl(3-((tert-butyldimethylsilyl)oxy)cyclohexyl)carbamate (1.0 g, 2.75 mmol) and 5% Pd/C (0.2 g) in methanol (40 mL) was stirred under a balloon of hydrogen for 6 h. The catalyst was removed by filtration over Celite and the resulting solution was concentrated to afford the amine 54 as a colourless oil (0.63 g, ~quantitative) which was carried forward without further purification. $\delta_H$ (400 MHz, CDCl$_3$) 0.06 (6H, s), 0.88 (9H, s), 0.96-1.11 (1H, m), 1.12-1.30 (3H, m), 1.69-1.83 (3H, m), 1.97-2.06 (1H, m), 2.21 (2H, br) 2.67-2.78 (1H, m) 3.65-3.66 (1H, m); $\delta_C$ (150 mHz, CDCl$_3$) -4.7, 18.2, 21.5, 25.9, 35.0, 35.5, 45.5 br, 49.1, 70.1.

(E)-N-((3-((tert-Butyldimethylsilyl)oxy)cyclohexyl)carbamoyl)-3-methoxy-2-methylacrylamide 55

Oxalyl chloride (0.51 mL, 0.76 g, 6 mmol) was added dropwise to a stirring solution of (E)-3-methoxy-2-methylacrylic acid (0.64 g, 5.5 mmol) in CH$_2$Cl$_2$ (10 mL). After 1 h the volatiles were removed under reduced pressure and the residue was dissolved in benzene (10 mL) and added to a stirring suspension of silver cyanate (1.65 g, 11 mmol) in benzene (5 mL) and the resulting mixture was heated under reflux for 1 h and then allowed to cool to room temp and settle. The supernatant solution (ca. 11 mL) was withdrawn by syringe added dropwise to a stirred, ice-cooled solution of 3-((tert-butyldimethylsilyl)oxy)cyclohexylamine 54 (0.61 g, 2.65 mmol) in THF (10 mL) and the mixture was stirred overnight. The solvents were removed and the residue was purified by flash chromatography (40% EtOAc/hexanes) to afford the desired product 55 as a colourless solid (0.46 g, 47%). $\delta_H$ (400 MHz, CDCl$_3$) 0.05 (3H, s), 0.06 (3H, s), 0.87 (9H, s), 1.06-1.33 (4H, m), 1.74-1.85 (2H, m), 1.76 (3H, d, J=1.2), 1.89-1.97 (1H, m), 2.11-2.18 (1H, m), 3.58-3.69 (1H, m), 3.69-3.79 (1H, m), 3.85 (3H, s), 7.29 (1H, q, J=1.2), 7.46 (1H, br s), 8.59 (1H, d, J=7.9); $\delta_C$ (75 MHz, CDCl$_3$) -4.7, -4.6, 8.8, 18.1, 23.0, 25.8, 32.2, 35.1, 42.4, 47.4, 61.4, 69.8, 107.3, 153.4, 158.3, 169.3; m/z (ES+) 371.4 [M+H]$^+$; HRMS (ES+) exact mass calculated for C$_{18}$H$_{35}$N$_2$O$_4$Si [M+H]+ 371.2366. found 371.2358.

1-(3-((tert-Butyldimethylsilyl)oxy)cyclohexyl)-5-methylpyrimidine-2,4(1H,3H)-dione 56

A mixture of (E)-N-((3-((tert-butyldimethylsilyl)oxy)cyclohexyl)carbamoyl)-3-methoxy-2-methylacrylamide 55

(0.45 g, 1.21 mmol), ethanol (2.5 mL), and conc. aqueous ammonia (2.5 mL) was placed in a sealed tube and heated in a pre-equilibrated bath at 100° C. for 24 h. The volatiles were removed under reduced pressure to afford the desired product 56 as a bone-white solid (0.41 g, ~quantitative) which was sufficiently pure to use directly in the next step. $\delta_H$ (400 MHz, CDCl$_3$) 0.06 (3H, s), 0.07 (3H, s), 0.88 (9H, s), 1.17-1.54 (4H, m), 1.80-1.97 (3H, m), 1.93 (3H, d, J=1.1) 2.01-2.10 (1H, m), 3.70 (1H, apparent tt, J=10.5, 4.3), 4.48 (1H, apparent tt, J=12.4, 3.7), 7.04 (1H, unresolved q, J=~1), 8.34 (1H, br s); $\delta_C$ (150 MHz, CDCl$_3$) −4.7, 12.6, 18.1, 21.9, 25.8, 30.8, 35.0, 41.2, 52.0, 69.9, 110.8, 136.3, 150.8, 163.5; m/z (ES−) 337.4 [M−H]$^-$.

3-Benzoyl-1-(3-((tert-butyldimethylsilyl)oxy)cyclohexyl)-5-methylpyrimidine-2,4(1H,3H)-dione 57

A solution of 1-(3-((tert-butyldimethylsilypoxy)cyclohexyl)-5-methylpyrimidine-2,4(1H,3H)-dione 56 (200 mg, 0.59 mmol), Hunig's base (206 µL, 153 mg), and DMAP (14 mg, 0.118 mmol) in CH$_2$Cl$_2$ (5 mL) was treated with benzoyl chloride (102 µL, 124 mg, 0.88 mmol) and irradiated in a microwave reactor (200 W, 75° C.) for 30 min and then stirred for 30 mins with an equal volume of saturated NaHCO$_3$. The mixture was partitioned with CH$_2$Cl$_2$ (25 mL) and sat. NaHCO$_3$ (25 mL), separated and the aqueous phase was extracted with two further portions of CH$_2$Cl$_2$ (20 mL each). The combined organic extracts were dried with MgSO$_4$ and concentrated, and the residue was purified by flash chromatography (20% EtOAc/Hexane) to afford the desired product 57 as a colourless solid (0.22 g, 80%). $\delta_H$ (400 MHz, CDCl$_3$) 0.06 (6H, two overlapping s), 0.88 (9H, s), 1.17-1.41 (3H, m), 1.49-1.59 (1H, m), 1.79-1.98 (3H, m), 1.97 (3H, d, J=1.1), 2.07-2.14 (1H, m), 3.69 (1H, apparent tt, J=10.4, 4.4), 4.49 (1H, apparent tt, J=12.6, 3.6), 7.14 (1H, unresolved q, J=~1.1), 7.46-7.52 (2H, m), 7.61-7.66 (1H, m), 7.90-7.94 (2H, m); $\delta_C$ (150 MHz, CDCl$_3$) 4.7, −4.6, −12.7, 18.1, 21.8, 25.8, 30.9, 35.0, 41.1, 52.4, 69.8, 110.9, 129.1, 130.4, 131.7, 134.9, 136.0, 149.9, 162.6, 169.2 m/z (ES+) 443.3 [M+H]$^+$; HRMS (ES+) exact mass calculated for C$_{24}$H$_{35}$N$_2$O$_4$Si [M+H]$^+$ 443.2366; found 443.2353.

3-Benzoyl-1-(3-hydroxycyclohexyl)-5-methylpyrimidine-2,4(1H,3H)-dione 58

A solution of TBAF (1 M in THF, 0.5 mL, 0.5 mmol) was added to a stirring solution of the TBS derivative 57 (200 mg) in THF (10 mL). After stirring overnight the solvent was removed under reduced pressure and the residue was partitioned with CH$_2$Cl$_2$ (25 nL) and 2 M HCl (25 mL). The layers were separated and the aqueous phase was extracted twice with CH$_2$Cl$_2$ (15 mL each). The combined organic extracts were washed with brine (25 mL), dried over MgSO$_4$ and concentrated. The residue was purified by flash chromatography (80% EtOAc/Hexane) to afford the desired product 58 as a white foam (117 mg, 79%). $\delta_H$ (400 MHz, CDCl$_3$) 1.20-1.29 (1H, m), 1.32-1.46 (2H, m), 1.46-1.56 (1H, m), 1.70 (1H, br s), 1.87-1.94 (2H, m), 1.97 (3H, d, J=1.1), 2.01-2.08 (1H, m), 2.20-2.27 (1H, m), 3.76 (1H, apparent tt, J=10.7, 4.3), 4.46 (1H, apparent tt, J=12.2, 3.4), 7.16 (1H, unresolved q, J=~1), 7.46-7.52 (2H, m), 7.61-7.67 (1H, m), 7.88-7.94 (2H, m); $\delta_C$ (75 MHz, CDCl$_3$) 12.6, 21.9, 30.6, 34.3, 40.6, 52.7, 69.1, 111.0, 129.2, 130.4, 131.7, 135.0, 136.2, 149.8, 162.6, 169.2; m/z (ES+) 329.3 [M+H]+; HRMS (ES+) exact mass calculated for C18H21N2O4 [M+H]+ 329.1501; found 329.1489.

Methyl 2-((3-(3-benzoyl-5-methyl-2,4-dioxo-3,4-dihydropyrimidin-1(2H)-yl)cyclohexyl)oxy)-2-(dimethoxyphosphoryl)acetate 59

A solution of 3-benzoyl-1-(3-hydroxycyclohexyl)-5-methylpyrimidine-2,4(1H,3H)-dione 58 (117 mg, 0.356 mmol) and trimethyl diazophonoacetate 18 (82 mg, 0.39 mmol) in benzene (5 mL) was purged with nitrogen for 10 min and then stirred with activated 4 Å molecular sieve (ca. ½ tsp) for 1 h. Rhodium acetate (2 mg, 4.2 µmol) was added and the mixture was placed in a pre-equilibrated bath at 90° C. for 18 h. The solvent was removed under reduced pressure and the residue was purified by flash chromatography (EtOAc) to afford 85 mg of product which contained inseparable water insertion product (ca 15%). $\delta_H$ (400 MHz, CDCl$_3$) 1.24-1.52 (3H, m), 1.55-1.70 (1H, m), 1.86-1.96 (2H, m), 1.97 (3H, s), 2.10-2.19 (1H, m), 2.29-2.38 (1H, m), 3.46-3.56 (1H, m), 3.82-3.91 (9H, m), 4.40-4.50 (1H, m), 4.47 (0.5H, d, J=19.9), 4.49 (0.5H, d, J=19.8), 7.12-7.15 (1H, m), 7.47-7.54 (2H, m), 7.62-7.68 (1H, m), 7.89-7.94 (2H, m). The presence of water insertion product was indicated by a characteristic dd ($\delta_H$ 4.61, J=16.0, 6.8)

2-((3-(5-methyl-2,4-dioxo-3,4-dihydropyrimidin-1(2H)-yl)cyclohexyl)oxy)-2-phosphonoacetic acid 60

Methyl 2-((3-(3-benzoyl-5-methyl-2,4-dioxo-3,4-dihydropyrimidin-1(2H)-yl)cyclohexyl)oxy)-2-(dimethoxyphosphoryl)acetate 59 (80 mg, ~80% pure, ca. 0.15 mmol) was dissolved in CH$_2$Cl$_2$ (3 mL) and treated with TMSBr (79 µL, 92 mg, 0.6 mmol). The mixture was irradiated in a microwave reactor (50 W, 50° C.) for 20 min then concentrated under reduced pressure. The residue was taken in aq. NaOH (1 M, 3 mL) and stirred at room temperature for 22 h. The mixture was acidified by dropwise addition of conc. HCl, concentrated under reduced pressure, and the residue was purified by charcoal chromatography to afford a white solid (42 mg-75% as ammonium salt) which was pure by $^1$H NMR. $\delta_H$ (400 MHz, D$_2$O) 1.06-1.31 (2H, m), 1.33-1.45 (1H, m), 1.45-1.57 (1H, m) 1.73-1.83 (1H, m), 1.77 (3H, s), 1.92-2.06 (1H, m), 2.26-2.20 (1H, m), 3.36-4.37 (1H, m), 4.01, (0.5H, d, J=18.8), 4.03 (0.5H, d, J=18.8), 4.18-4.29 (1H, m), 7.50 (1H, two overlapping s); $\delta_C$ (150 MHz, D$_2$O) 11.4, 21.3, 21.4, 29.9, 30.2, 30.9, 36.1, 36.7, 53.2, 78.5, 110.9, 128.3, 128.8, 139.5, 139.6, 152.2, 166.5, 177.0.

The following compounds may be prepared according the same methodology following the protocols described in the examples section above:

2-(2-(5-methyl-2,4-dioxo-3,4-dihydropyrimidin-1(2H)-yl)cyclopropoxy)-2-phosphonoacetic acid;

2-(2-(2,4-dioxo-3,4-dihydropyrimidin-1(2H)-yl)cyclopropoxy)-2-phosphonoacetic acid;

2-(2-(4-amino-2-oxopyrimidin-1(2H)-yl)cyclopropoxy)-2-phosphonoacetic acid;

2-(2-(5-fluoro-2,4-dioxo-3,4-dihydropyrimidin-1(2H)-yl)cyclopropoxy)-2-phosphonoacetic acid;

2-(2-(6-amino-9H-purin-9-yl)cyclopropoxy)-2-phosphonoacetic acid;

2-(3-(5-methyl-2,4-dioxo-3,4-dihydropyrimidin-1(2H)-yl)cyclobutoxy)-2-phosphonoacetic acid;

2-(3-(2,4-dioxo-3,4-dihydropyrimidin-1(2H)-yl)cyclobutoxy)-2-phosphonoacetic acid;

2-(2-(4-amino-2-oxopyrimidin-1(2H)-yl)cyclobutoxy)-2-phosphonoacetic acid;

2-(3-(5-fluoro-2,4-dioxo-3,4-dihydropyrimidin-1(2H)-yl)cyclobutoxy)-2-phosphonoacetic acid;

2-(3-(6-amino-9H-purin-9-yl)cyclobutoxy)-2-phosphonoacetic acid;

and other related nucleobase derivatives"

HIV-1 RT Assays in the Presence of Artificial Template/Primer

To prepare the template/primers for the RT experiments, 0.15 mM poly(U), poly(A), and poly(I) were mixed with an equal volume of 0.0375 mM oligo(dA), oligo(dT), and oligo(dC), respectively. The final concentrations of the templates in the RT reaction mixture were 0.015 mM. The reaction mixture (50 µl) contained 50 mM Tris.HCl (pH 7.8), 5 mM dithiothreitol, 300 mM glutathione, 500 µM EDTA, 150 mM KCl, 5 mM $MgCl_2$, 1.25 µg of bovine serum albumin, an appropriate concentration of labeled (tritiated) substrate dTTP, dCTP, or dATP (2 µCi/assay), a fixed concentration of the template/primer poly(A).oligo(dT) (0.015 mM), poly(I).oligo(dC) (0.015 mM), and poly(U).oligo(dA) (0.015 mM), 0.06% Triton X-100, 10 µl of inhibitor solution (containing various concentrations of the compounds), and 1 µl of the RT preparation. The reaction mixtures were incubated at 37° C. for 30 min, at which time 100 µl of yeast RNA (1 mg/ml) and 1 ml of $Na_4P_2O_7$ (0.02 M) in trichloroacetic acid (5% v/v) were added. The solutions were kept on ice for 30 min, after which the acid-insoluble material was washed and analyzed for radioactivity.

For the experiments in which the 50% inhibitory concentration ($IC_{50}$) of the test compounds was determined, fixed concentrations of 1.25 µM [$^3$H]dTTP, 1.75 µM [$^3$H]dATP, or 2.5 µM [$^3$H]dCTP were used.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

REFERENCE

[1] Gallo, R. C.; Montagnier, L. *New England Journal of Medicine* 2003, 349, 2283.
[2] WHO UNAIDS Global Facts & Figures; CDC Worldwide Hepatitis Statistics
[3] Broder, S. *Antiviral Research* 2010, 85, 1.
[4] Vandamme, A.-M.; Van, L. K.; De Clercq, E. *Drugs* 1999, 57, 337.
[5] De Clercq, E. *Nat. Rev. Drug Discovery* 2007, 6, 1001
[6] De Clercq, E. *Current Opinion in Pharmacology* 2010, 10, 507.
[7] *Combination Therapy of AIDS*; Birkhauser Basel, 2004.
[8] De Clercq, E. *Int. J. Antimicrob. Agents* 2009, 33, 307.
[9] Cihlar, T.; Ray, A. S. *Antiviral Research* 2010, 85, 39.
[10] Warnke, D.; Barreto, J.; Temesgen, Z. *J. Clin. Pharmacol.* 2007, 47, 1570.
[11] Balzarini, *J. Pharm. World Sci.* 1994, 16, 113.
[12] Kulik, K.; Radzikowska, E.; Kaczmarek, R.; Baraniak, J.; Stec, W. J.; De, C. E.; Balzarini, J.; Pannecouque, C. *Antiviral Chem. Chemother.* 2011, 21, 143.
[13] Goldring, A. O.; Gilbert, I. H.; Mahmood, N.; Balzarini, J. *Bioorganic &; Medicinal Chemistry Letters* 1996, 6, 2411.
[14] D. Cahard, C. McGuigan, J. Balzarini. *Mini Rev. Med. Chem.* 2004, 4, 371-381.
[15] C. Meier, J. Balzarini. *Antiviral Res.* 2006, 71, 282-292.
[16] N. Valiaeva, J. R. Beadle, K. A. Aldern, J. Trahan, K. Y. Hostetler. *Antiviral Res.* 2006, 72, 10-19
[17] A. S. Ray, K. Y. Hostetler. *Antiviral Res.* 2011, 92, 277-291.
[18] Coe, D. *J. Chem. Soc. Perkin Trans.* 1 1992, 2695.
[19] De Clercq, E.; Holy, A.; Rosenberg, I.; Sakuma, T.; Balzarini, J.; Maudgal, P. C. *Nature (London)* 1986, 323, 464.
[20] Hwang, J.-T.; Choi, J.-R. *Drugs Future* 2004, 29, 163.
[21] Casu, F.; Chiacchio, M. A.; Romeo, R.; Gumina, G. *Curr. Org. Chem.* 2007, 11, 999.
[22] Jeong, L. S.; Lee, J. A. *Antiviral Chem. Chemother.* 2004, 15, 235.
[23] Rodriguez, J. B.; Comin, M. J. *Mini Reviews in Medicinal Chemistry* 2003, 3, 95.
[24] Borchardt, R. T.; Keller, B. T.; Patel-Thombre, U. *J. Biol. Chem.* 1984, 259, 4353.
[25] Tardibono Jr, L. P.; Miller, M. J.; Balzarini, J. *Tetrahedron* 2011, 67, 825.
[26] Marce, P.; Diaz, Y.; Matheu, M. I.; Castillon, S. *Org. Lett.* 2008, 10, 4735.
[27] Kim, C. U.; Luh, B. Y.; Martin, J. C. *Bioorg. Med. Chem. Lett.* 1992, 2, 307.
[28] Boojamra, C. G.; Parrish, J. P.; Sperandio, D.; Gao, Y.; Petrakovsky, O. V.; Lee, S. K.; Markevitch, D. Y.; Vela, J. E.; Laflamme, G.; Chen, J. M.; Ray, A. S.; Barron, A. C.; Sparacino, M. L.; Desai, M. C.; Kim, C. U.; Cihlar, T.; Mackman, R. L. *Bioorganic & Medicinal Chemistry* 2009, 17, 1739.
[29] Mao, J. C.; Otis, E. R.; von, E. A. M.; Herrin, T. R.; Fairgrieve, J. S.; Shipkowitz, N. L.; Duff, R. G. *Antimicrob Agents Chemother* 1985, 27, 197.
[30] McKenna, C. E.; Ye, T. G.; Levy, J. N.; Pham, P.; Wen, T.; Bongartz, J. P.; Starnes, M. C.; Cheng, Y. C. *Phosphorus, Sulfur, and Silicon and the Related Elements* 1990, 49-50, 183.
[31] Wnuk, S. F.; Robins, M. J. *Journal of the American Chemical Society* 1996, 118, 2519.
[32] Králiková, Š.; Buděšinský, M.; Masojídková, M.; Rosenberg, I. *Tetrahedron Letters* 2000, 41, 955.
[33] Romanenko, V. D.; Kukhar, V. P. *Chemical Reviews* 2006, 106, 3868.
[34] Chen, W.; Flavin, M. T.; Filler, R.; Xu, Z.-Q. *Tetrahedron Lett.* 1996, 37, 8975.
[35] Chen, W.; Flavin, M. T.; Filler, R.; Xu, Z.-Q. *J. Chem. Soc., Perkin Trans.* 1 1998, 3979.
[36] Chen, X.; Wiemer, A. J.; Hohl, R. J.; Wiemer, D. F. *J Org Chem* 2002, 67, 9331.
[37] Weaver, R.; Gilbert, I. H. *Tetrahedron* 1997, 53, 5537.
[38] Weaver, R.; Gilbert, I. H.; Mahmood, N.; Balzarini, J. *Bioorganic & Medicinal Chemistry Letters* 1996, 6, 2405.
[39] Boudreau, M. A.; Vederas, J. C. *Org. Biomol. Chem.* 2007, 5, 627.
[40] Kaiser, M. M.; Jansa, P.; Dracísnky, M.; Janeba, Z. *Tetrahedron* 2012, 68, 4003.
[41] Charvet A-S.; Camplo, M. F., P.; Graciet, J-P.; Mourier, N.; Chermann, J-C.; Kraus, J-L. *J. Med. Chem.* 1994, 37, 2216.
[42] Debarge, S.; Balzarini, J.; Maguire, A. R. The *Journal of Organic Chemistry* 2010, 76, 105.
[43] Hladezuk, I.; Chastagner, V.; Collins, S. G.; Plunkett, S. J.; Ford, A.; Debarge, S.; Maguire. A. R. *Tetrahedron* 2012, 68, 1894.

[44] Rosenblum, L. L.; Patton, G.; Grigg, A. R.; Frater, A. J.; Cain, D.; Erlwein, O.; Hill, C. L.; Clarke, J. R.; McClure, M. O. *Antiviral Chem. Chemother.* 2001, 12, 91.

[45] J Med Chem, 2007, 50, 1840-9 and Mini-Rev. Med. Chem. 2004, 4, 371-8.

[46] Mini Rev Med Chem 2004, 4, 409-419.

[47] Antimicrob Agents Chemother. 1993, 37, 2247-2250.

[48] Mini Rev Med Chem 2004, 4, 395-408.

[49] Antiviral Chem and Chemother. 1997, 8, 557.

[50] Angew. Chem. Int. Ed. Engl. 1996, 35, 70-72; Mini Rev Med Chem 2002, 2, 219-234; Eur J Org Chem 2006, 1001-1102; J Med Chem 2005, 48, 8079-86.

[51] J Med Chem 1999, 42, 1604-1614; J Med Chem, 1998, 4, 1417-1427; Eur J Org Chem, 2006, 197-206.

[52] Hostetler K Y, Antiviral research 2009, 82, A84-98; Ray and Hostetler, Antiviral research 011, 92, 277-291.

[53] Coe, D. M.; Hilbert, H.; Noble, S. A.; Peel, M. R.; Roberts, S. M.; Storer, R. *Journal of the Chemical Society, Chemical Communications* 1991, 312.

[54] Trost, B. M.; Kuo, G. H.; Benneche, T. *J. Am. Chem. Soc.* 1988, 110, 621.

[55] Merlo, V.; Roberts, S. M.; Storer, R.; Bethell, R. C. *Journal of the Chemical Society, Perkin Transactions 1* 1994, 1477.

[56] Amblard, F.; Nolan, S. P.; Agrofoglio, L. A. *Tetrahedron* 2005, 61, 7067.

[57] McKenna, C. E.; Scmidhauser, J. *J. Chem. Soc., Chem Commun.* 1979, 739.

[58] Tietze, L. F.; Stadler, C.; Bohnke, N.; Brasche, G.; Grube, A. Synlett 2007, 485.

[59] Hoard, D. E.; Ott, D. G. *J. Am. Chem. Soc.* 1965, 87, 1785.

[60] Srivashava, N.; Banik, B. K. *J. Org. Chem.* 2002, 68, 2109-2114.

[61] Levy, L. M.; de Gonzalo, G.; Gotor, V. *Tetrahedron: Asymmetry* 2004, 15, 2051-2056.

The invention claimed is:

1. A compound of formula (I), or a pharmaceutically acceptable salt or prodrug thereof,

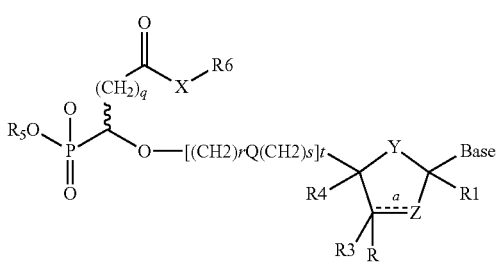

(I)

wherein:
X is selected from O and $NR_9$;
Y is $C=CH_2$ or $(CR_8R_{8'})_n$, where n is 1 or 2;
Z is a direct bond, or $(CR_2R_{2'})_p$, where p is 1, 2, 3 or 4;
Q is selected from O, S, $CH_2$, $CH=CH$ and $C≡C$;
r is 0, 1, 2 or 3;
s is 0, 1, 2 or 3;
t is 0 or 1;
q is 0, 1, 2, 3, 4 or 5;
when p is 1, 2, 3 or 4, 'a' is a single bond, or a double bond (in which case one of $R_2$ and $R_{2'}$ is absent, and one of $R_3$ and $R_{3'}$ is absent);
$R_1$, $R_2$, $R_{2'}$, $R_3$, $R_{3'}$, $R_4$, $R_8$ and $R_{8'}$ are each independently selected from H, $OR_{10}$, halogen, CN, $NR_{11}R_{12}$, $N_3$, $SR_{13}$, $C_{1-6}$-alkyl, $C_{2-6}$-alkenyl, $C_{2-6}$-alkynyl and aryl, or one of $R_2$ and $R_{2'}$ together with one of $R_3$ and $R_{3'}$ form an epoxide;
$R_5$ is selected from H, $P(=O)(OH)_2$ and $P(=O)(OH)—O—P(=O)(OH)_2$;
$R_6$ is selected from H and $C_{1-6}$-alkyl;
$R_9$-$R_{13}$ are each independently selected from H and $C_{1-6}$-alkyl;
Base is a natural or non-natural nucleobase, and
wherein the prodrug is selected from a phosphoramidate derivative, a SATE (S-acyl-2-thioethyl) ester derivative, a pivaloyloxymethyl (POM) derivative, an isopropyloxymethylcarbonyl (POC) derivative, a cyclo-saligenyl (cycloSal) derivative and an alkyloxyalkyl derivative.

2. A compound of formula (Ia), or a pharmaceutically acceptable salt or prodrug thereof,

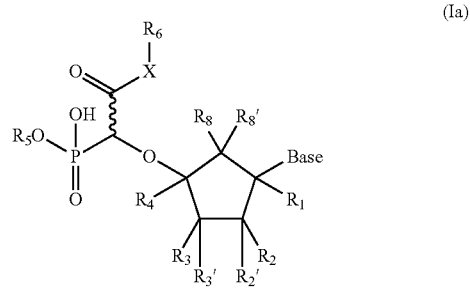

(Ia)

wherein:
X is selected from O and $NR_9$;
$R_1$, $R_2$, $R_{2'}$, $R_3$, $R_{3'}$, $R_4$, $R_8$ and $R_{8'}$ are each independently selected from H, $OR_{10}$, halogen, CN, $NR_{11}R_{12}$, $N_3$, $SR_{13}$, $C_{1-6}$-alkyl, $C_{2-6}$-alkenyl, $C_{2-6}$-alkynyl and aryl, or one of $R_2$ and $R_{2'}$ together with one of $R_3$ and $R_{3'}$ form an epoxide;
$R_5$ is selected from H, $P(=O)(OH)_2$ and $P(=O)(OH)—O—P(=O)(OH)_2$;
$R_6$ is selected from H and $C_{1-6}$-alkyl;
$R_9$-$R_{13}$ are each independently selected from H and $C_{1-6}$-alkyl;
Base is a natural or non-natural nucleobase, and
wherein the prodrug is selected from a phosphoramidate derivative, a SATE (S-acyl-2-thioethyl) ester derivative, a pivaloyloxymethyl (POM) derivative, an isopropyloxymethylcarbonyl (POC) derivative, a cyclo-saligenyl (cycloSal) derivative and an alkyloxyalkyl derivative.

3. A compound according to claim 1 wherein the Base is a purine or pyrimidine nucleobase.

4. A compound according to claim 1 wherein the Base is a nucleobase selected from adenine (A), cytosine (C), 5-methylcytosine (MeC), isocytosine, pseudoisocytosine, guanine (G), thymine (T), uracil (U), 5-bromouracil, 5-fluorouracil, 5-propynyluracil, 5-propynyl-6-fluorouracil, 5-methylthiazole-uracil, 6-aminopurine, 2-aminopurine, inosine, 2,6-diaminopurine, 7-propynyl-7-deazaadenine, 7-propynyl-7-deazaguanine, 5-thiazolyluracil, 2-thiothymine, 5-propynyl-cytosine, 5-thiazolylcytosine, phenoxazine, G-clamp, $N^2$-aminopropylguanine, 2-chloro-6-aminopurine, 4-thiothymine, 5-(2-halovinyl)uracil and N-4-substituted cytosine.

5. A compound according to claim 1 wherein X is O and $R_6$ is H or $C_{1-6}$-alkyl.

6. A compound according to claim 1 wherein $R_5$ is H.

7. A compound according to claim 1 wherein $R_8$ and $R_{8'}$ are both H.

8. A compound according to claim 1 wherein $R_1$, $R_2$, $R_{2'}$, $R_3$, $R_{3'}$, $R_4$, $R_5$ and $R_{5'}$ are all H.

9. A compound of formula (Id), or a pharmaceutically acceptable salt or prodrug thereof:

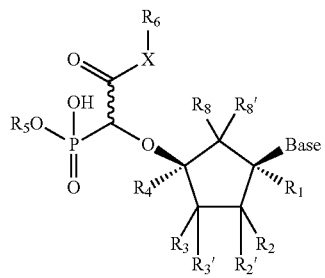

(Id)

wherein:

X is selected from O and $NR_9$;

$R_1$, $R_2$, $R_{2'}$, $R_3$, $R_{3'}$, $R_4$, $R_8$ and $R_{8'}$ are each independently selected from H, $OR_{10}$, halogen, CN, $NR_{11}R_{12}$, $N_3$, $SR_{13}$, $C_{1-6}$-alkyl, $C_{2-6}$-alkenyl, $C_{2-6}$-alkynyl and aryl, or one of $R_2$ and $R_{2'}$ together with one of $R_3$ and $R_{3'}$ form of an epoxide;

$R_5$ is selected from H, $P(=O)(OH)_2$ and $P(=O)(OH)—O—P(=O)(OH)_2$;

$R_6$ is selected from H and $C_{1-6}$-alkyl;

$R_9$-$R_{13}$ are each independently selected from H and $C_{1-6}$-alkyl;

Base is a natural or non-natural nucleobase, and wherein the prodrug is selected from a phosphoramidate derivative, a SATE (S-acyl-2-thioethyl) ester derivative, a pivaloyloxymethyl (POM) derivative, an isopropyloxymethylcarbonyl (POC) derivative, a cyclo-saligenyl (cycloSal) derivative and an alkyloxyalkyl derivative.

10. A compound of formula (Ie), or a pharmaceutically acceptable salt or prodrug thereof:

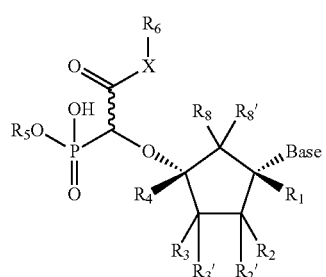

(Ie)

wherein:

X is selected from O and $NR_9$;

$R_1$, $R_2$, $R_{2'}$, $R_3$, $R_{3'}$, $R_4$, $R_8$ and $R_{8'}$ are each independently selected from H, $OR_{10}$, halogen, CN, $NR_{11}R_{12}$, $N_3$, $SR_{13}$, $C_{1-6}$-alkyl, $C_{2-6}$-alkenyl, $C_{2-6}$-alkynyl and aryl, or one of $R_2$ and $R_{2'}$ together with one of $R_3$ and $R_{3'}$ form of an epoxide;

$R_5$ is selected from H, $P(=O)(OH)_2$ and $P(=O)(OH)—O—P(=O)(OH)_2$;

$R_6$ is selected from H and $C_{1-6}$-alkyl;

$R_9$-$R_{13}$ are each independently selected from H and $C_{1-6}$-alkyl;

Base is a natural or non-natural nucleobase, and wherein the prodrug is selected from a phosphoramidate derivative, a SATE (S-acyl-2-thioethyl) ester derivative, a pivaloyloxymethyl (POM) derivative, an isopropyloxymethylcarbonyl (POC) derivative, a cyclo-saligenyl (cycloSal) derivative and an alkyloxyalkyl derivative.

11. A compound according to claim 1 which is a racemic mixture of a compound of formula (I).

12. A compound selected from the following:

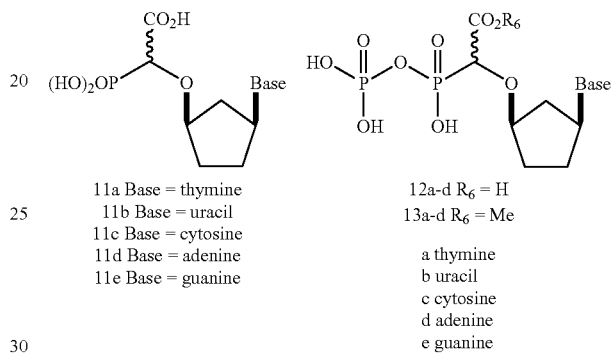

11a Base = thymine
11b Base = uracil
11c Base = cytosine
11d Base = adenine
11e Base = guanine 12a-d $R_6$ = H
13a-d $R_6$ = Me a thymine
b uracil
c cytosine
d adenine
e guanine or a pharmaceutically acceptable salt or prodrug thereof wherein:

$R_6$ is selected from H and $C_{1-6}$-alkyl; and

Base is a natural or non-natural nucleobase, and wherein the prodrug is selected from a phosphoramidate derivative, a SATE (S-acyl-2-thioethyl) ester derivative, a pivaloyloxymethyl (POM) derivative, an isopropyloxymethylcarbonyl (POC) derivative, a cyclo-saligenyl (cycloSal) derivative and an alkyloxyalkyl derivative.

13. A compound according to claim 1 which is selected from the following:

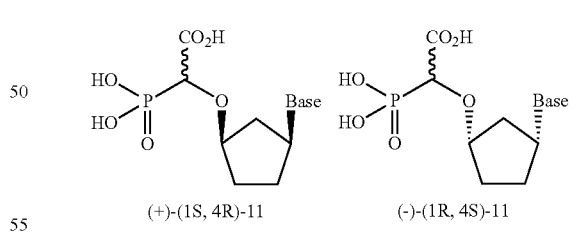

(+)-(1S, 4R)-11

(−)-(1R, 4S)-11 wherein the Base is selected from thymine, uracil, cytosine, adenine and guanine;

or a pharmaceutically acceptable salt or prodrug thereof, and wherein the prodrug is selected from a phosphoramidate derivative, a SATE (S-acyl-2-thioethyl) ester derivative, a pivaloyloxymethyl (POM) derivative, an isopropyloxymethylcarbonyl (POC) derivative, a cyclo-saligenyl (cycloSal) derivative and an alkyloxyalkyl derivative.

14. A pharmaceutical composition comprising a compound according to claim 1 or a pharmaceutically acceptable salt or prodrug thereof, admixed with a pharmaceutically acceptable diluent, excipient or carrier.

15. A method of applying the compound of formula (I) according to claim 1, or a pharmaceutically acceptable salt or prodrug thereof comprising administering the compound in medicine.

16. A method of treating a virus infection with the compound of formula (I) according to claim 1 or a pharmaceutically acceptable salt or prodrug thereof comprising administering to a subject having the virus infection, wherein the virus of the viral infection is selected from human cytomegalovirus (HCMV), herpes simplex virus type 1 (HSV-1) and type 2 (HSV-2), human immunodeficiency virus type 1 (HIV-1) and type 2 (HIV-2), varicella-zoster virus (VZV), and hepatitis B virus.

17. A method of preparing a medication for treating a viral disorder comprising combining the compound according to claim 1 or a pharmaceutically acceptable salt or prodrug thereof, with a pharmaceutically acceptable diluent, excipient or carrier.

18. The method of claim 15 wherein said compound is administered in combination with one or more other antiviral compounds.

19. A method of treating a virus infection, said method comprising administering to a mammal a therapeutically effective amount of a compound according to claim 1, or a pharmaceutically acceptable salt or prodrug thereof, the mammal subject having the virus infection, wherein the virus of the viral infection is selected from human cytomegalovirus (HCMV), herpes simplex virus type 1 (HSV-1) and type 2 (HSV-2), human immunodeficiency virus type 1 (HIV-1) and type 2 (HIV-2), varicella-zoster virus (VZV), and hepatitis B virus.

20. A method of identifying further candidate compounds capable of inhibiting HIV-RT comprising performing an assay with a compound according to claim 1, or a pharmaceutically acceptable salt or prodrug thereof.

21. The method of claim 20 wherein said assay is a competitive binding assay.

22. A combination comprising a compound of formula (I) according to claim 1, or a pharmaceutically acceptable salt or prodrug thereof, and a further active agent.

23. A process for preparing a compound of claim 1 having a formula (If) or (Ig), wherein $R_6$ is H or $C_{1-6}$-alkyl, and the Base is a natural or non-natural nucleobase, said process comprising the steps of:

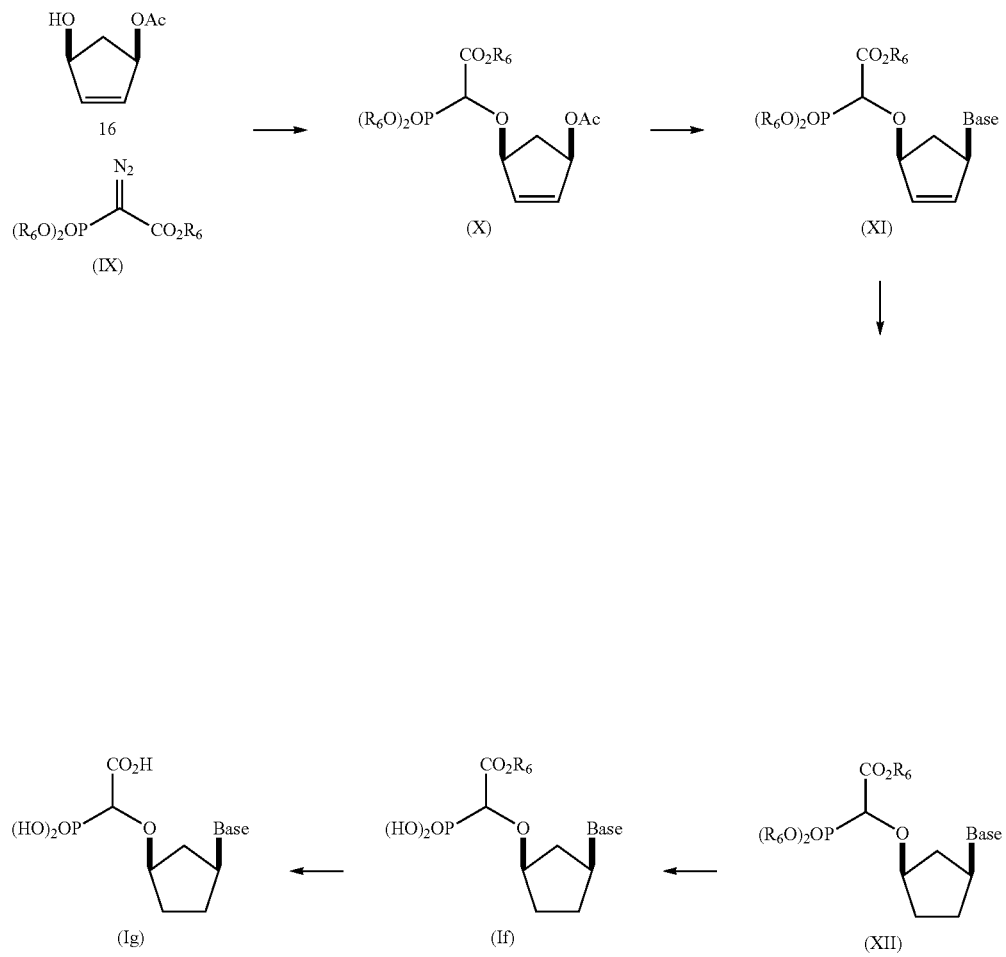

(i) reacting a compound of formula 16 with a compound of formula (IX) in the presence of a rhodium (II) acetate or copper (II) triflate catalyst to form a compound of formula (X);

(ii) reacting said compound of formula (X) with a Base in the presence of a palladium(0) catalyst in a suitable solvent to form a compound of formula (XI);

(iv) hydrogenating said compound of formula (XI) in the presence of palladium on charcoal to form a compound of formula (XII);

(v) treating said compound of formula (XII) with TMSBr in MeCN to form a compound of formula (If); and (vi) optionally hydrolysing said compound of formula (If) to form a compound of formula (Ig).

24. The compound according to claim 2 wherein the Base is a purine or pyrimidine nucleobase.

25. The compound according to claim 2 wherein the Base is a nucleobase selected from adenine (A), cytosine (C), 5-methylcytosine (MeC), isocytosine, pseudoisocytosine, guanine (G), thymine (T), uracil (U), 5-bromouracil, 5-fluorouracil, 5-propynyluracil, 5-propynyl-6-fluorouracil, 5-methylthiazole-uracil, 6-aminopurine, 2-aminopurine, inosine, 2,6-diaminopurine, 7-propynyl-7-deazaadenine, 7-propynyl-7-deazaguanine, 5-thiazolyluracil, 2-thiothymine, 5-propynyl-cytosine, 5-thiazolylcytosine, phenoxazine, G-clamp, $N^2$-aminopropylguanine, 2-chloro-6-aminopurine, 4-thiothymine, 5-(2-halovinyl)uracil and N-4-substituted cytosine.

26. The compound according to claim 9 wherein the Base is a purine or pyrimidine nucleobase.

27. The compound according to claim 9 wherein the Base is a nucleobase selected from adenine (A), cytosine (C), 5-methylcytosine (MeC), isocytosine, pseudoisocytosine, guanine (G), thymine (T), uracil (U), 5-bromouracil, 5-fluorouracil, 5-propynyluracil, 5-propynyl-6-fluorouracil, 5-methylthiazole-uracil, 6-aminopurine, 2-aminopurine, inosine, 2,6-diaminopurine, 7-propynyl-7-deazaadenine, 7-propynyl-7-deazaguanine, 5-thiazolyluracil, 2-thiothymine, 5-propynyl-cytosine, 5-thiazolylcytosine, phenoxazine, G-clamp, $N^2$-aminopropylguanine, 2-chloro-6-aminopurine, 4-thiothymine, 5-(2-halovinyl)uracil and N-4-substituted cytosine.

28. The compound according to claim 10 wherein the Base is a purine or pyrimidine nucleobase.

29. The compound according to claim 10 wherein the Base is a nucleobase selected from adenine (A), cytosine (C), 5-methylcytosine (MeC), isocytosine, pseudoisocytosine, guanine (G), thymine (T), uracil (U), 5-bromouracil, 5-fluorouracil, 5-propynyluracil, 5-propynyl-6-fluorouracil, 5-methylthiazole-uracil, 6-aminopurine, 2-aminopurine, inosine, 2,6-diaminopurine, 7-propynyl-7-deazaadenine, 7-propynyl-7-deazaguanine, 5-thiazolyluracil, 2-thiothymine, 5-propynyl-cytosine, 5-thiazolylcytosine, phenoxazine, G-clamp, $N^2$-aminopropylguanine, 2-chloro-6-aminopurine, 4-thiothymine, 5-(2-halovinyl)uracil and N-4-substituted cytosine.

30. The compound according to claim 12 wherein the Base is a purine or pyrimidine nucleobase.

31. The compound according to claim 12 wherein the Base is a nucleobase selected from adenine (A), cytosine (C), 5-methylcytosine (MeC), isocytosine, pseudoisocytosine, guanine (G), thymine (T), uracil (U), 5-bromouracil, 5-fluorouracil, 5-propynyluracil, 5-propynyl-6-fluorouracil, 5-methylthiazole-uracil, 6-aminopurine, 2-aminopurine, inosine, 2,6-diaminopurine, 7-propynyl-7-deazaadenine, 7-propynyl-7-deazaguanine, 5-thiazolyluracil, 2-thiothymine, 5-propynyl-cytosine, 5-thiazolylcytosine, phenoxazine, G-clamp, $N^2$-aminopropylguanine, 2-chloro-6-aminopurine, 4-thiothymine, 5-(2-halovinyl)uracil and N-4-substituted cytosine.

32. The method according to claim 15 wherein the Base is a purine or pyrimidine nucleobase.

33. The method according to claim 15 wherein the Base is a nucleobase selected from adenine (A), cytosine (C), 5-methylcytosine (MeC), isocytosine, pseudoisocytosine, guanine (G), thymine (T), uracil (U), 5-bromouracil, 5-fluorouracil, 5-propynyluracil, 5-propynyl-6-fluorouracil, 5-methylthiazole-uracil, 6-aminopurine, 2-aminopurine, inosine, 2,6-diaminopurine, 7-propynyl-7-deazaadenine, 7-propynyl-7-deazaguanine, 5-thiazolyluracil, 2-thiothymine, 5-propynyl-cytosine, 5-thiazolylcytosine, phenoxazine, G-clamp, $N^2$-aminopropylguanine, 2-chloro-6-aminopurine, 4-thiothymine, 5-(2-halovinyl)uracil and N-4-substituted cytosine.

* * * * *